US 6,969,583 B2
United States Patent
Delaney, IV et al.

(10) Patent No.: US 6,969,583 B2
(45) Date of Patent: Nov. 29, 2005

(54) METHOD FOR DETECTING VARIANT HBV

(75) Inventors: William Delaney, IV, San Mateo, CA (US); Stephen Alister Locarnini, St Kilda East (AU); Robert Yung Ming Chen, Flemmington (AU); Angeline Bartholomeusz, Carnegie (AU); Harriet Isom, Hummelstown, PA (US)

(73) Assignees: Melbourne Health, Parkville (AU); The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/781,891

(22) Filed: Feb. 2, 2001

(65) Prior Publication Data

US 2003/0096222 A1 May 22, 2003

Related U.S. Application Data

(60) Provisional application No. 60/179,948, filed on Feb. 3, 2000.

(51) Int. Cl.$^7$ .................. C12N 15/866; C12N 15/63; C12N 15/64; C12Q 1/68; C12Q 1/70
(52) U.S. Cl. ................ 435/5; 435/6; 435/7.1; 435/320.1; 435/235.1; 435/325; 435/366; 435/370; 435/7.4; 435/7.6; 435/69.1; 435/455; 435/456; 435/236; 536/23.1; 536/23.72; 530/350
(58) Field of Search .................. 435/320.1, 235.1, 435/5, 6, 7.1, 325, 366, 370, 7.4, 7.6, 69.1, 455, 456, 236; 536/23.1, 23.72; 530/350; 514/256, 266, 259, 247, 252; 544/333, 277

(56) References Cited

PUBLICATIONS

Oon et al., Antiviral Research, 1999, vol. 41, p. 113–118.*
Locarnini et al., Hepatology, 1998, vol. 27, No. 1, p. 294–297.*
Boyce et al., PNAS, 1996, vol. 93, pp. 2348–2352.*
Delaney IV, et al., (1999) "Use of the Hepatitis B Virus Recombinant Baculovirus–HepG2 System to Study the Effects of (–)–B–2', 3'– Dideoxy–3'– Thiacytidine on Replication of Hepatitis B Virus and Accumulation of Covalently Closed Circular DNA", *Antimicrobial Agents and Chemotherapy* 43(8) :2017–2026.
Harrison, et al., (1991) "Independent Emergence of a Vaccine–Induced Escape Mutant of Hepatitis B Virus", *Journal of Hepatology 13* (4), S105–S107.
Fujii, et al.,(1992) "Gly $^{145}$ To Arg Substitution in HBs Antigen of Immune Escape Mutant of Hepatitis B Virus", *Biochemical and Biophysical Research Communications*, *184* (3) :1152–1157.
Delaney IV, et al., (1998) "Hepatitis B Virus Replication in Human HepG2 Cells Mediated by Hepatitis B Virus Recombinant Baculocirus", *Journal of Hepatology 28* :1134–1146.
McMahon, et al. (1992) "Genetic Alterations in the Gene Encoding the Major HbsAg: DNA and Immunological Analysis of Recurrent HbsAg Derived from Monoclonal Antibody–Treated Liver Transplant Patients", *Journal of Hepatology 15* :757–766.
Okamoto, et al. (1992) "Mutations within the S Gene of Hepatitis B Virus Transmitted from Mothers to Babies Immunized with Hepatitis B Immune Globulin and Vaccine", *Pediatric Research 32(3)* :264–268.
Carman, et al., (1990) "Vaccine–Induced Escape Mutant of Hepatitis B Virus", *The Lancet 336*:325–329.
Carman, et al. (1992) "Genetic Variation in Hepatitis B Virus", *The American Gastroenterological Association 102* : 711–719.
Gerlich, et al. (1991) "Functions of Hepatitis B Virus Proteins and Virus Assembly", *Viral Hepatitis and Liver Disease*, F.B. Hollinger, et al. Eds., Williams–Wilkens, Baltimore, MD :121–134.
Tiollais, et al. (1985) "The Hepatitis B Virus", *Nature 317* : 489–495.
Stuyver, et al. (2000) "A New Genotype of Hepatitis B Virus: Complete Genome and Phylogenetic Relatedness", *Journal of General Virology 81* :67–74.
Ryder, et al. (1984) "Screening for Hepatitis B Virus Markers is not Justified in West African Transfusion Centres", *The Lancet* :449–452.
Norder, et al. (1993) "Genetic Relatedness of Hepatitis B Viral Strains of Diverse Geographical Origin and Natural Variations in the Primary Structure of the Surface Antigen", *Journal of General Virology 74* :1341–1348.
Beasley, et al. (1981) "Hepatocellular Carcinoma and Hepatitis B Virus", *The Lancet* :1129–1133.

* cited by examiner

*Primary Examiner*—David Guzo
(74) *Attorney, Agent, or Firm*—Scully, Scott, Murphy & Presser

(57) ABSTRACT

The present invention relates generally to an assay for detecting variant Hepatitis B viruses (HBVs) which exhibit altered sensitivity to agents. The variant HBVs are delivered to cells using a baculovirus vector. The altered sensitivity to an agent is in relation to the effects of the agent on one or more stages of infection, replication, assembly or release of virus or virus-like particles. The identification of variant HBVs with altered sensitivities to anti-HBV agents provides a means of monitoring cross resistance, or the development of new therapeutics effective against variant HBVs with altered sensitivities to other anti-HBV agents, as well as monitoring therapeutic protocols. The present invention further provides variant HBVs detected by the assay of the present invention and to components thereof as well as recombinant, chemical analogue, homologue and derivative forms of such components.

17 Claims, 47 Drawing Sheets

```
(421)        430           440           450
 422              438
SNDLSWLSLD  VSAAFYHIₚPL  HPAAMPHLLIV  GSSGLᴰₛRYVA
         Domain A
```

```
   HBsAg G112R              T123P            Y/F134S        D144E G145R
 460              470            480            490
    464 466             477            488            499
RLSSTₙSRₙNI*N  NYHQYHGR***DₙLH  DₙYₛCSRDQLYVS  LLₘLLYKQTYFGRw
```

```
  HBsAg            A157D       E164D       F170L
 500              510           520           530
        512        519      523/524/526/528/530
KLHLYₗSₐHPIIᵥ  LGFRKIₗPMGVG  GLSPFLLAQF  TSAICₗSₐVₘVₜRCR
         Domain B
```

```
                    W196L    W199S
 HBsAg       M195I/S196W M198I S204T        S210R
 540              550           560
     546         550  553      559         565
AFFₚHCLᵥAᵥFSₐY  MDDVLₘVLGAKRₛT  VGQEHLₛRESFLYFTₐSA
         Domain C
```

```
 570              580           590
         575
IᵥTCNₛFᵥLLSDLᵥGI  HLNPNQKTKRW  GYSLNFMGYIᵥI G
         Domain D         Domain E
```

| | $P_{108}$ | | $L_{110}$ | P R |
|---|---|---|---|---|
| *329616/HPBADRICG | A C T A C C A A G G T A T G T T G T C T C C T C T A C T T C C A A G |
| 221499/HPBADW3 | A C T A T C A A G G T A T G T T G C C C G T T T G T C C T C T A A T T C C A G G |
| 221500/HPBCG | A C T A C C A A G G T A T G T T G C C C G T T T G T C C T C T A C T T C C A G G |
| 62280/XXHEPAV | A C T A T C A A G G T A T G T T G C C C G T T T G T C C T C T A A T T C C A G G |
| 59439/HBVAYWE | A C T A T C A A G G T A T G T T G C C C G T T T G T C C T C T A A T T C C A G G |
| 59429/HBVAYWC | A C T A T C A A G G T A T G T T G C C C G T T T G T C C T C T A A T T C C A G G |
| 59418/HBVADW2 | A T T A T C A A G G T A T G T T G C C C G T T T G T C C T C T A A T T C C A G G |
| 59408/HBVADRM | A C T A C C A A G G T A T G T T G C C C G T T T G T C C T C T A C T T C C A G G |
| 59404/HBVADR4 | A C T A C C A A G G T A T G T T G C C C G T T T G T C C T C T A A T T C C A G G |
| 329640/HPBAYW | A C T A T C A A G G T A T G T T G C C C G T T T G T C C T C T A A T T C C A G G |
| 313780/HBVAYWMCG | A C T A T C A A G G T A T G T T G C C C G T T T G T C C T C T A A T T C C A G G |
| 229417/HPBADW1 | A C T A T C A A G G T A T G T T G C C C G T T T G T C C T C T A A T T C C A G G |

|   | $S_{193}$ | $V_{194}$ | $I_{195}$ | $W_{196}$ | $M_{197}$ | $M_{198}$ | $W_{199}$ | $Y_{220}$ | W | G | P | S | L |
|---|---|---|---|---|---|---|---|---|---|---|---|---|---|
| *329616/HPBADR1CG | TTCAG | T | TATA | TGGA | TGAT | GATG | TGGT | AT | TGGG | GGGC | CAAG | TCTG |
| 221499/HPBADW3 | TTCAG | T | TATA | TGGA | TGAT | GATG | TGGT | AT | TGGG | GGGC | CAAG | TCTG |
| 221500/HPBCG | TTCAG | T | TATA | TGGA | TGAT | GATG | TGGT | [T] | TGGG | GGGC | CAAG | TCTG |
| 62280/XXHEPAV | TTCAG | T | TATA | TGGA | TGAT | GATG | TGGT | AT | TGGG | GGGC | CAAG | TCTG |
| 59439/HBVAYWE | TTCAG | T | TATA | TGGA | TGAT | GATG | TGGT | AT | TGGG | GGGC | CAAG | TCTG |
| 59429/HBVAYWC | TTCAG | T | TATA | TGGA | TGAT | GATG | TGGT | AT | TGGG | GGGC | CAAG | TCTG |
| 59418/HBVADW2 | TTCAG | [C] | TATA | TGGA | TGAT | GATG | TGGT | AT | TGGG | GGGC | CAAG | TCTG |
| 59408/HBVADRM | TTCAG | T | TATA | TGGA | TGAT | GATG | TGGT | AT | TGGG | GGGC | CAAG | TCTG |
| 59404/HBVADR4 | TTCAG | T | TATA | TGGA | TGAT | GATG | TGGT | AT | TGGG | GGGC | CAAG | TCTG |
| 329640/HPBAYW | TTCAG | T | TATA | TGGA | TGAT | GATG | TGGT | AT | TGGG | GGGC | CAAG | TCTG |
| 313780/HBVAYWMCG | TTCAG | T | TATA | TGGA | TGAT | GATG | TGGT | AT | TGGG | GGGC | CAAG | TCTG |
| 229417/HPBADW1 | TTCAG | T | TATA | TGGA | TGAT | GATG | TGGT | AT | TGGG | GGGC | CAAG | TCTG |

Figure 3I

|  | Y | N | I | L | $S_{210}$ | P | F | L | P | L | L | P | I |
|---|---|---|---|---|---|---|---|---|---|---|---|---|---|
| *329616/HPBADR1CG | T A C A | A C | A T | C T T | C G A G T | C C C | T T T T | T A C | C T | C G C | T A | T T A C C | A A T T T |
| 221499/HPBADW3 | T A C A | A C | A T | C T T | C G A G T | C C C | T T T T | T A T | C T | C G C | T G T | T T A C C | A A T T T |
| 221500/HPBCG | T A C A | A C | A T | C T T | C G A G T | C C C | T T T T | T A C | C T | C G C | T G T | T T A C C | A A T T T |
| 62280/XXHEPAV | T A C A | A G | C A T | C T T | C G A G T | C C C | T T T T | T A C | C T | C G C | T G T | T T A C C | A A T T T |
| 59439/HBVAYWE | T A C A | A G | C A T | C T T | C G A G T | C C C | T T T T | T A C | C T | C G C | T G T | T T A C C | A A T T T |
| 59429/HBVAYWC | T A C A | A G | C A T | C G A G T | C C C | T T T T | T A C | C T | C G C | T G T | T T A C C | A A T T T |
| 59418/HBVADW2 | T A C A | A G | C A T | C T T | C G A G T | C C C | T T T T | T A T | C T | C G C | T G T | T T A C C | A A T T T |
| 59408/HBVADRM | T A C A | A C | A T | C T T | C G A G T | C C C | T T T T | T A C | C T | C G C | T A T | T T A C C | A A T T T |
| 59404/HBVADR4 | T A C A | A C | A T | C T T | C G A G T | C C C | T T T T | T A C | C T | C G C | T A T | T T A C C | A A T T T |
| 329640/HPBAYW | T A C A | A G | C A T | C T T | C G A G T | C C C | T T T T | T A C | C T | C G C | T G T | T T A C C | A A T T T |
| 313780

|   | F | $F_{220}$ | C | L | W | V | Y | $I_{226}$ | * |
|---|---|---|---|---|---|---|---|---|---|
| *329616/HPBADR1CG | T C T T | T G T C | T C T T | T G G G | T A T A | C A T T | T G A |
| 221499/HPBADW3    | T C T T | T G T C | T C T T | T G G G | T A T A | C A T T | T A A |
| 221500/HPBCG      | T C T T | T G T C | T C T T | T G G G | T A T A | C A T T | T G A |
| 62280/XXHEPAV     | T C T T | C G T C | T C T T | T G G G | T A T A | C A T T | T A A |
| 59439/HBVAYWE     | T C T T | T G T C | T C T T | T G G G | T A T A | C A T T | T A A |
| 59429/HBVAYWC     | T C T T | T G T C | T C T C | T G G G | T A T A | C A T T | T A A |
| 59418/HBVADW2     | T C T T | T G T C | T C T C | T G G G | T A T A | C A T T | T G A |
| 59408/HBVADRM     | T C T T | T G T C | T C T T | T G G G | T A T A | C A T T | T A A |
| 59404/HBVADR4     | T C T T | T G T C | T C T T | T G G G | T A T A | C A T T | T A A |
| 329640/HPBAYW     | T C T T | T G T C | T C T T | T G G G | C A T A | C A T T | T A A |
| 313780/HBVAYWMCG  | T C T T | T G T C | T C T T | T G G G | T A T A | C A T T | T A A |
| 229417/HPBADW1    | T C T T | T G T C | T C T T | T G G G | T A T A | C A T T | T A A |

Figure 3K pBBHBV1.5

```
Sequence Range: 1 to 4084

10         20         30         40         50
   GGACGACCCCTCGCGGGGCCGCTTGGGACTCTCTCGTCCCCTTCTCCGTC 60         70         80         90        100
   TGCCGTTCCAGCCGACCACGGGGCGCACCTCTCTTTACGCGGTCTCCCCG 110        120        130        140        150
   TCTGTGCCTTCTCATCTGCCGGTCCGTGTGCACTTCGCTTCACCTCTGCA 160        170        180        190        200
   CGTTGCATGGAGACCACCGTGAACGCCCATCAGATCCTGCCCAAGGTCTT 210        220        230        240        250
   ACATAAGAGGACTCTTGGACTCCCAGCAATGTCAACGACCGACCTTGAGG 260        270        280        290        300
   CCTACTTCAAAGACTGTGTGTTTAAGGACTGGGAGGAGCTGGGGGAGGAG 310        320        330        340        350
   ATTAGGTTAAAGGTCTTTGTATTAGGAGGCTGTAGGCATAAATTGGTCTG 360        370        380        390        400
   CGCACCAGCACCATGCAACTTTTTCACCTCTGCCTAATCATCTCTTGTAC 410        420        430        440        450
   ATGTCCCACTGTTCAAGCCTCCAAGCTGTGCCTTGGGTGGCTTTGGGGCA 460        470        480        490        500
   TGGACATTGACCCTTATAAAGAATTTGGAGCTACTGTGGAGTTACTCTCG 510        520        530        540        550
   TTTTTGCCTTCTGACTTCTTTCCTTCCGTCAGAGATCTCCTAGACACCGC 560        570        580        590        600
   CTCAGCTCTGTATCGAGAAGCCTTAGAGTCTCCTGAGCATTGCTCACCTC 610        620        630        640        650
   ACCATACTGCACTCAGGCAAGCCATTCTCTGCTGGGGGGAATTGATGACT 660        670        680        690        700
   CTAGCTACCTGGGTGGGTAATAATTTGGAAGATCCAGCATCCAGGGATCT
```

```
A------------------------------------A
       710       720       730       740       750
    AGTAGTCAATTATGTTAATACTAACATGGGTTTAAAGATCAGGCAACTAT 760       770       780       790       800
    TGTGGTTTCATATATCTTGCCTTACTTTTGGAAGAGAGACTGTACTTGAA 810       820       830       840       850
    TATTTGGTCTCTTTCGGAGTGTGGATTCGCACTCCTCCAGCCTATAGACC 860       870       880       890       900
    ACCAAATGCCCCTATCTTATCAACACTTCCGGAAACTACTGTTGTTAGAC 910       920       930       940       950
    GACGGGACCGAGGCAGGTCCCCTAGAAGAAGAACTCCCTCGCCTCGCAGA 960       970       980       990      1000
    CGCAGATCTCAATCGCCGCGTCGCAGAAGATCTCAATCTCGGGAATCTCA 1010      1020      1030      1040      1050
    ATGTTAGTATTCCTTGGACTCATAAGGTGGGAAACTTTACGGGGCTTTAT 1060      1070      1080      1090      1100
    TCCTCTACAGTACCTATCTTTAATCCTGAATGGCAAACTCCTTCCTTTCC 1110      1120      1130      1140      1150
    TAAGATTCATTTACAAGAGGACATTATTAATAGGTGTCAACAATTTGTGG 1160      1170      1180      1190      1200
    GCCCTCTCACTGTAAATGAAAGAGAAGATTGAAATTAATTATGCCTGCT 1210      1220      1230      1240      1250
    AGATTCTATCCTACCCACACTAAATATTTGCCCTTAGACAAAGGAATTAA 1260      1270      1280      1290      1300
    ACCTTATTATCCAGATCAGGTAGTTAATCATTACTTCCAAACCAGACATT 1310      1320      1330      1340      1350
    ATTTACATACTCTTTGGAAGGCTGGTATTCTATATAAGAGGGAAACCACA 1360      1370      1380      1390      1400
    CGTAGCGCATCATTTTGCGGGTCACCATATTCTTGGGAACAAGAGCTACA 1410      1420      1430      1440      1450
    GCATGGGAGGTTGGTCATCAAAACCTCGCAAAGGCATGGGGACGAATCTT
B------------------------------------B
```

Figure 5B

```
B-  -  -  -  -  -  -  -  -  -  -  -  -  -  -  -  -  -  -  -  -  -  - B
         1460      1470      1480      1490      1500
    TCTGTTCCCAACCCTCTGGGATTCTTTCCCGATCATCAGTTGGACCCTGC 1510      1520      1530      1540      1550
    ATTCGGAGCCAACTCAAACAATCCAGATTGGGACTTCAACCCCATCAAGG 1560      1570      1580      1590      1600
    ACCACTGGCCAGCAGCCAACCAGGTAGGAGTGGGAGCATTCGGGCCAGGG 1610      1620      1630      1640      1650
    CTCACCCCTCCACACGGCGGTATTTTGGGGTGGAGCCCTCAGGCTCAGGG 1660      1670      1680      1690      1700
    CATATTGACCACAGTGTCAACAATTCCTCCTCCTGCCTCCACCAATCGGC 1710      1720      1730      1740      1750
    AGTCAGGAAGGCAGCCTACTCCCATCTCTCCACCTCTAAGAGACAGTCAT 1760      1770      1780      1790      1800
    CCTCAGGCCATGCAGTGGAATTCCACTGCCTTCCACCAAGCTCTGCAGGA 1810      1820      1830      1840      1850
    TCCCAGAGTCAGGGGTCTGTATCTTCCTGCTGGTGGCTCCAGTTCAGGAA 1860      1870      1880      1890      1900
    CAGTAAACCCTGCTCCGAATATTGCCTCTCACATCTCGTCAATCTCCGCG 1910      1920      1930      1940      1950
    AGGACTGGGGACCCTGTGACGAACATGGAGAACATCACATCAGGATTCCT 1960      1970      1980      1990      2000
    AGGACCCCTGCTCGTGTTACAGGCGGGGTTTTTCTTGTTGACAAGAATCC 2010      2020      2030      2040      2050
    TCACAATACCGCAGAGTCTAGACTCGTGGTGGACTTCTCTCAATTTTCTA 2060      2070      2080      2090      2100
    GGGGGATCTCCCGTGTGTCTTGGCCAAAATTCGCAGTCCCCAACCTCCAA 2110      2120      2130      2140      2150
    TCACTCACCAACCTCCTGTCCTCCAATTTGTCCTGGTTATCGCTGGATGT 2160      2170      2180      2190      2200
    GTCTGCGGCGTTTTATCATATTCCTCTTCATCCTGCTGCTATGCCTCATC
C-  -  -  -  -  -  -  -  -  -  -  -  -  -  -  -  -  -  -  -  -  -  - C
```

```
      2210      2220      2230      2240      2250
TTCTTATTGGTTCTTCTGGATTATCAAGGTATGTTGCCCGTTTGTCCTCT 2260      2270      2280      2290      2300
AATTCCAGGATCAACAACAACCAGTACGGGACCATGCAAAACCTGCACGA 2310      2320      2330      2340      2350
CTCCTGCTCAAGGCAACTCTATGTTTCCCTCATGTTGCTGTACAAAACCT 2360      2370      2380      2390      2400
ACGGATGGAAATTGCACCTGTATTCCATCCCATCGTCCTGGGCTTTCGC 2410      2420      2430      2440      2450
AAAATACCTATGGGAGTGGGCCTCAGTCCGTTTCTCTTGGCTCAGTTTAC 2460      2470      2480      2490      2500
TAGTGCCATTTGTTCAGTGGTTCGTAGGGCTTTCCCCCACTGTTTGGCTT 2510      2520      2530      2540      2550
TCAGCTATATGGATGATGTGGTATTGGGGGCCAAGTCTGTACAGCATCGT 2560      2570      2580      2590      2600
GAGTCCCTTTATACCGCTGTTACCAATTTTCTTTTGTCTCTGGGTATACA 2610      2620      2630      2640      2650
TTTAAACCCTAACAAAACAAAAAGATGGGGTTATTCCCTAAACTTCATGG 2660      2670      2680      2690      2700
GCTACATAATTGGAAGTTGGGGAACTTTGCCACAGGATCATATTGTACAA 2710      2720      2730      2740      2750
AAGATCAAACACTGTTTTAGAAAACTTCCTGTTAACAGGCCTATTGATTG 2760      2770      2780      2790      2800
GAAAGTATGTCAAAGAATTGTGGGTCTTTTGGGCTTTGCTGCTCCATTTA 2810      2820      2830      2840      2850
CACAATGTGGATATCCTGCCTTAATGCCTTTGTATGCATGTATACAAGCT 2860      2870      2880      2890      2900
AAACAGGCTTTCACTTTCTCGCCAACTTACAAGGCCTTTCTAAGTAAACA 2910      2920      2930      2940      2950
GTACATGAACCTTTACCCCGTTGCTCGGCAACGGCCTGGTCTGTGCCAAG
```

```
       2960      2970      2980      2990      3000
     TGTTTGCTGACGCAACCCCCACTGGCTGGGGCTTGGCCATAGGCCATCAG 3010      3020      3030      3040      3050
     CGCATGCGTGGAACCTTTGTGGCTCCTCTGCCGATCCATACTGCGGAACT 3060      3070      3080      3090      3100
     CCTAGCCGCTTGTTTTGCTCGCAGCCGGTCTGGAGCAAAGCTCATCGGAA 3110      3120      3130      3140      3150
     CTGACAATTCTGTCGTCCTCTCGCGGAAATATACATCGTTTCCATGGCTG 3160      3170      3180      3190      3200
     CTAGGCTGTACTGCCAACTGGATCCTTCGCGGGACGTCCTTTGTTTACGT 3210      3220      3230      3240      3250
     CCCGTCGGCGCTGAATCCCGCGGACGACCCCTCGCGGGGCCGCTTGGGAC 3260      3270      3280      3290      3300
     TCTCTCGTCCCCTTCTCCGTCTGCCGTTCCAGCCGACCACGGGGCGCACC 3310      3320      3330      3340      3350
     TCTCTTTACGCGGTCTCCCCGTCTGTGCCTTCTCATCTGCCGGTCCGTGT 3360      3370      3380      3390      3400
     GCACTTCGCTTCACCTCTGCACGTTGCATGGAGACCACCGTGAACGCCCA 3410      3420      3430      3440      3450
     TCAGATCCTGCCCAAGGTCTTACATAAGAGGACTCTTGGACTCCCAGCAA 3460      3470      3480      3490      3500
     TGTCAACGACCGACCTTGAGGCCTACTTCAAAGACTGTGTGTTTAAGGAC 3510      3520      3530      3540      3550
     TGGGAGGAGCTGGGGGAGGAGATTAGGTTAAAGGTCTTTGTATTAGGAGG 3560      3570      3580      3590      3600
     CTGTAGGCATAAATTGGTCTGCGCACCAGCACCATGCAACTTTTTCACCT 3610      3620      3630      3640      3650
     CTGCCTAATCATCTCTTGTACATGTCCCACTGTTCAAGCCTCCAAGCTGT 3660      3670      3680      3690      3700
     GCCTTGGGTGGCTTTGGGGCATGGACATTGACCCTTATAAAGAATTTGGA
```

```
         3710       3720       3730       3740       3750
      GCTACTGTGGAGTTACTCTCGTTTTTGCCTTCTGACTTCTTTCCTTCCGT 3760       3770       3780       3790       3800
      CAGAGATCTCCTAGACACCGCCTCAGCTCTGTATCGAGAAGCCTTAGAGT 3810       3820       3830       3840       3850
      CTCCTGAGCATTGCTCACCTCACCATACTGCACTCAGGCAAGCCATTCTC 3860       3870       3880       3890       3900
      TGCTGGGGGGAATTGATGACTCTAGCTACCTGGGTGGGTAATAATTTGGA 3910       3920       3930       3940       3950
      AGATCCAGCATCCAGGGATCTAGTAGTCAATTATGTTAATACTAACATGG 3960       3970       3980       3990       4000
      GTTTAAAGATCAGGCAACTATTGTGGTTTCATATATCTTGCCTTACTTTT 4010       4020       4030       4040       4050
      GGAAGAGAGACTGTACTTGAATATTTGGTCTCTTTCGGAGTGTGGATTCG 4060       4070       4080
      CACTCCTCCAGCCTATAGACCACCAAATGCCCCT
```

Figure 5F

Rank 2 Eqn 8076 [LgstcDoseRsp_] y=a/(1+(x/b)^c)

Rank 2 Eqn 8076 [LgstcDoseRsp_] y=a/(1+(x/b)^c)

Rank 2 Eqn 8076 [LgstcDoseRsp_] y=a/(1+(x/b)^c)

Rank 2 Eqn 8076 [LgstcDoseRsp_] y=a/(1+(x/b)^c)

Rank 45 Eqn 19 y=a+binx/x^2

Rank 20 Eqn 10 y=a+b(lnx)^2

Cold dCTP Competition

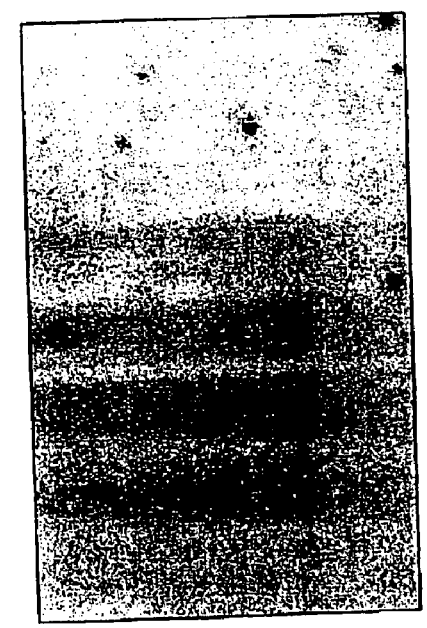
Figure 13A
Figure 13B

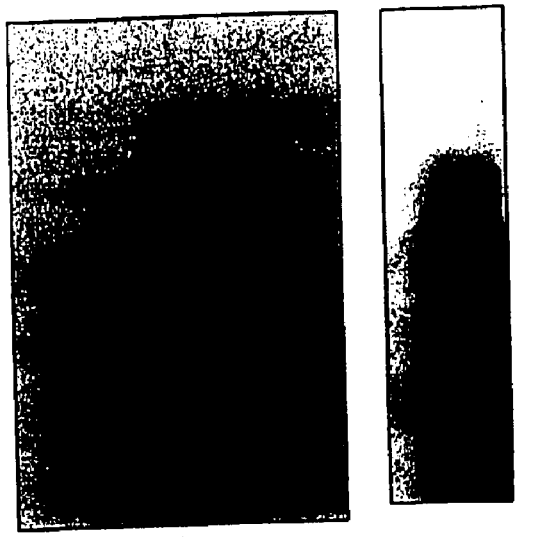
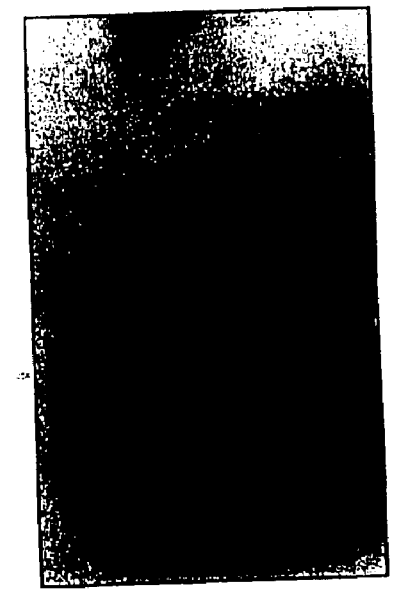
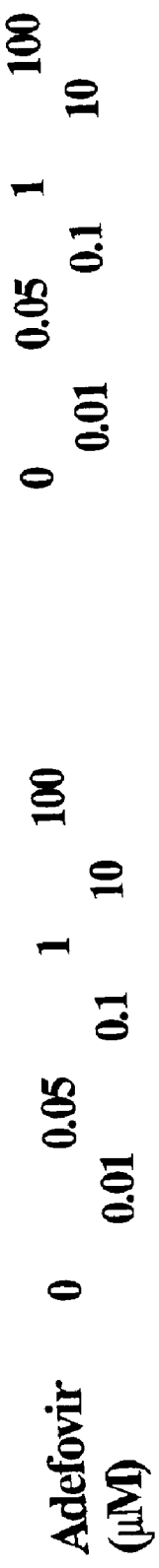
Figure 13C
Figure 13D

Sequence Range: 1 to 4496

```
         10        20        30        40        50
GATATCCTGCCTTAATGCCTTTGTATGCATGTATACAAGCTAAACAGGCT 60        70        80        90       100
TTCACTTTCTCGCCAACTTACAAGGCCTTTCTAAGTAAACAGTACATGAA 110       120       130       140       150
CCTTTACCCCGTTGCTCGGCAACGGCCTGGTCTGTGCCAAGTGTTTGCTG 160       170       180       190       200
ACGCAACCCCCACTGGCTGGGGCTTGGCCATAGGCCATCAGCGCATGCGT 210       220       230       240       250
GGAACCTTTGTGGCTCCTCTGCCGATCCATACTGCGGAACTCCTAGCCGC 260       270       280       290       300
TTGTTTTGCTCGCAGCCGGTCTGGAGCAAAGCTCATCGGAACTGACAATT 310       320       330       340       350
CTGTCGTCCTCTCGCGGAAATATACATCGTTTCCATGGCTGCTAGGCTGT 360       370       380       390       400
ACTGCCAACTGGATCCTTCGCGGGACGTCCTTTGTTTACGTCCCGTCGGC 410       420       430       440       450
GCTGAATCCCGCGGACGACCCCTCGCGGGGCCGCTTGGGACTCTCTCGTC 460       470       480       490       500
CCCTTCTCCGTCTGCCGTTCCAGCCGACCACGGGGCGCACCTCTCTTTAC 510       520       530       540       550
GCGGTCTCCCCGTCTGTGCCTTCTCATCTGCCGGTCCGTGTGCACTTCGC 560       570       580       590       600
TTCACCTCTGCACGTTGCATGGAGACCACCGTGAACGCCCATCAGATCCT 610       620       630       640       650
GCCCAAGGTCTTACATAAGAGGACTCTTGGACTCCCAGCAATGTCAACGA 660       670       680       690       700
CCGACCTTGAGGCCTACTTCAAAGACTGTGTGTTTAAGGACTGGGAGGAG
```

```
            710       720       730       740       750
      CTGGGGGAGGAGATTAGGTTAAAGGTCTTTGTATTAGGAGGCTGTAGGCA 760       770       780       790       800
      TAAATTGGTCTGCGCACCAGCACCATGCAACTTTTTCACCTCTGCCTAAT 810       820       830       840       850
      CATCTCTTGTACATGTCCCACTGTTCAAGCCTCCAAGCTGTGCCTTGGGT 860       870       880       890       900
      GGCTTTGGGGCATGGACATTGACCCTTATAAAGAATTTGGAGCTACTGTG 910       920       930       940       950
      GAGTTACTCTCGTTTTTGCCTTCTGACTTCTTTCCTTCCGTCAGAGATCT 960       970       980       990      1000
      CCTAGACACCGCCTCAGCTCTGTATCGAGAAGCCTTAGAGTCTCCTGAGC 1010      1020      1030      1040      1050
      ATTGCTCACCTCACCATACTGCACTCAGGCAAGCCATTCTCTGCTGGGGG 1060      1070      1080      1090      1100
      GAATTGATGACTCTAGCTACCTGGGTGGGTAATAATTTGGAAGATCCAGC 1110      1120      1130      1140      1150
      ATCCAGGGATCTAGTAGTCAATTATGTTAATACTAACATGGGTTTAAAGA 1160      1170      1180      1190      1200
      TCAGGCAACTATTGTGGTTTCATATATCTTGCCTTACTTTTGGAAGAGAG 1210      1220      1230      1240      1250
      ACTGTACTTGAATATTTGGTCTCTTTCGGAGTGTGGATTCGCACTCCTCC 1260      1270      1280      1290      1300
      AGCCTATAGACCACCAAATGCCCCTATCTTATCAACACTTCCGGAAACTA 1310      1320      1330      1340      1350
      CTGTTGTTAGACGACGGGACCGAGGCAGGTCCCCTAGAAGAAGAACTCCC 1360      1370      1380      1390      1400
      TCGCCTCGCAGACGCAGATCTCAATCGCCGCGTCGCAGAAGATCTCAATC 1410      1420      1430      1440      1450
      TCGGGAATCTCAATGTTAGTATTCCTTGGACTCATAAGGTGGGAAACTTT
```

```
         1460       1470       1480       1490       1500
    ACGGGGCTTTATTCCTCTACAGTACCTATCTTTAATCCTGAATGGCAAAC 1510       1520       1530       1540       1550
    TCCTTCCTTTCCTAAGATTCATTTACAAGAGGACATTATTAATAGGTGTC 1560       1570       1580       1590       1600
    AACAATTTGTGGGCCCTCTCACTGTAAATGAAAAGAGAAGATTGAAATTA 1610       1620       1630       1640       1650
    ATTATGCCTGCTAGATTCTATCCTACCCACACTAAATATTTGCCCTTAGA 1660       1670       1680       1690       1700
    CAAAGGAATTAAACCTTATTATCCAGATCAGGTAGTTAATCATTACTTCC 1710       1720       1730       1740       1750
    AAACCAGACATTATTTACATACTCTTTGGAAGGCTGGTATTCTATATAAG 1760       1770       1780       1790       1800
    AGGGAAACCACACGTAGCGCATCATTTTGCGGGTCACCATATTCTTGGGA 1810       1820       1830       1840       1850
    ACAAGAGCTACAGCATGGGAGGTTGGTCATCAAAACCTCGCAAAGGCATG 1860       1870       1880       1890       1900
    GGGACGAATCTTTCTGTTCCCAACCCTCTGGGATTCTTTCCCGATCATCA 1910       1920       1930       1940       1950
    GTTGGACCCTGCATTCGGAGCCAACTCAAACAATCCAGATTGGGACTTCA 1960       1970       1980       1990       2000
    ACCCCATCAAGGACCACTGGCCAGCAGCCAACCAGGTAGGAGTGGGAGCA 2010       2020       2030       2040       2050
    TTCGGGCCAGGGCTCACCCCTCCACACGGCGGTATTTTGGGGTGGAGCCC 2060       2070       2080       2090       2100
    TCAGGCTCAGGGCATATTGACCACAGTGTCAACAATTCCTCCTCCTGCCT 2110       2120       2130       2140       2150
    CCACCAATCGGCAGTCAGGAAGGCAGCCTACTCCCATCTCTCCACCTCTA 2160       2170       2180       2190       2200
    AGAGACAGTCATCCTCAGGCCATGCAGTGGAATTCCACTGCCTTCCACCA
```

```
        2210       2220       2230       2240       2250
     AGCTCTGCAGGATCCCAGAGTCAGGGGTCTGTATCTTCCTGCTGGTGGCT 2260       2270       2280       2290       2300
     CCAGTTCAGGAACAGTAAACCCTGCTCCGAATATTGCCTCTCACATCTCG 2310       2320       2330       2340       2350
     TCAATCTCCGCGAGGACTGGGGACCCTGTGACGAACATGGAGAACATCAC 2360       2370       2380       2390       2400
     ATCAGGATTCCTAGGACCCCTGCTCGTGTTACAGGCGGGGTTTTTCTTGT 2410       2420       2430       2440       2450
     TGACAAGAATCCTCACAATACCGCAGAGTCTAGACTCGTGGTGGACTTCT 2460       2470       2480       2490       2500
     CTCAATTTTCTAGGGGGATCTCCCGTGTGTCTTGGCCAAAATTCGCAGTC 2510       2520       2530       2540       2550
     CCCAACCTCCAATCACTCACCAACCTCCTGTCCTCCAATTTGTCCTGGTT 2560       2570       2580       2590       2600
     ATCGCTGGATGTGTCTGCGGCGTTTTATCATATTCCTCTTCATCCTGCTG 2610       2620       2630       2640       2650
     CTATGCCTCATCTTCTTATTGGTTCTTCTGGATTATCAAGGTATGTTGCC 2660       2670       2680       2690       2700
     CGTTTGTCCTCTAATTCCAGGATCAACAACAACCAGTACGGGACCATGCA 2710       2720       2730       2740       2750
     AAACCTGCACGACTCCTGCTCAAGGCAACTCTATGTTTCCCTCATGTTGC 2760       2770       2780       2790       2800
     TGTACAAAACCTACGGATGGAAATTGCACCTGTATTCCCATCCCATCGTC 2810       2820       2830       2840       2850
     CTGGGCTTTCGCAAAATACCTATGGGAGTGGGCCTCAGTCCGTTTCTCTT 2860       2870       2880       2890       2900
     GGCTCAGTTTACTAGTGCCATTTGTTCAGTGGTTCGTAGGGCTTTCCCCC 2910       2920       2930       2940       2950
     ACTGTTTGGCTTTCAGCTATATGGATGATGTGGTATTGGGGGCCAAGTCT
```

```
       2960      2970      2980      2990      3000
GTACAGCATCGTGAGTCCCTTTATACCGCTGTTACCAATTTTCTTTTGTC 3010      3020      3030      3040      3050
TCTGGGTATACATTTAAACCCTAACAAAACAAAAAGATGGGGTTATTCCC 3060      3070      3080      3090      3100
TAAACTTCATGGGCTACATAATTGGAAGTTGGGGAACTTTGCCACAGGAT 3110      3120      3130      3140      3150
CATATTGTACAAAAGATCAAACACTGTTTTAGAAAACTTCCTGTTAACAG 3160      3170      3180      3190      3200
GCCTATTGATTGGAAAGTATGTCAAAGAATTGTGGGTCTTTTGGGCTTTG 3210      3220      3230      3240      3250
CTGCTCCATTTACACAATGTGGATATCCTGCCTTAATGCCTTTGTATGCA 3260      3270      3280      3290      3300
TGTATACAAGCTAAACAGGCTTTCACTTTCTCGCCAACTTACAAGGCCTT 3310      3320      3330      3340      3350
TCTAAGTAAACAGTACATGAACCTTTACCCCGTTGCTCGGCAACGGCCTG 3360      3370      3380      3390      3400
GTCTGTGCCAAGTGTTTGCTGACGCAACCCCCACTGGCTGGGGCTTGGCC 3410      3420      3430      3440      3450
ATAGGCCATCAGCGCATGCGTGGAACCTTTGTGGCTCCTCTGCCGATCCA 3460      3470      3480      3490      3500
TACTGCGGAACTCCTAGCCGCTTGTTTTGCTCGCAGCCGGTCTGGAGCAA 3510      3520      3530      3540      3550
AGCTCATCGGAACTGACAATTCTGTCGTCCTCTCGCGGAAATATACATCG 3560      3570      3580      3590      3600
TTTCCATGGCTGCTAGGCTGTACTGCCAACTGGATCCTTCGCGGGACGTC 3610      3620      3630      3640      3650
CTTTGTTTACGTCCCGTCGGCGCTGAATCCCGCGGACGACCCCTCGCGGG 3660      3670      3680      3690      3700
GCCGCTTGGGACTCTCTCGTCCCCTTCTCCGTCTGCCGTTCCAGCCGACC
```

```
         3710       3720       3730       3740       3750
      ACGGGGCGCACCTCTCTTTACGCGGTCTCCCCGTCTGTGCCTTCTCATCT 3760       3770       3780       3790       3800
      GCCGGTCCGTGTGCACTTCGCTTCACCTCTGCACGTTGCATGGAGACCAC 3810       3820       3830       3840       3850
      CGTGAACGCCCATCAGATCCTGCCCAAGGTCTTACATAAGAGGACTCTTG 3860       3870       3880       3890       3900
      GACTCCCAGCAATGTCAACGACCGACCTTGAGGCCTACTTCAAAGACTGT 3910       3920       3930       3940       3950
      GTGTTTAAGGACTGGGAGGAGCTGGGGGAGGAGATTAGGTTAAAGGTCTT 3960       3970       3980       3990       4000
      TGTATTAGGAGGCTGTAGGCATAAATTGGTCTGCGCACCAGCACCATGCA 4010       4020       4030       4040       4050
      ACTTTTTCACCTCTGCCTAATCATCTCTTGTACATGTCCCACTGTTCAAG 4060       4070       4080       4090       4100
      CCTCCAAGCTGTGCCTTGGGTGGCTTTGGGGCATGGACATTGACCCTTAT 4110       4120       4130       4140       4150
      AAAGAATTTGGAGCTACTGTGGAGTTACTCTCGTTTTTGCCTTCTGACTT 4160       4170       4180       4190       4200
      CTTTCCTTCCGTCAGAGATCTCCTAGACACCGCCTCAGCTCTGTATCGAG 4210       4220       4230       4240       4250
      AAGCCTTAGAGTCTCCTGAGCATTGCTCACCTCACCATACTGCACTCAGG 4260       4270       4280       4290       4300
      CAAGCCATTCTCTGCTGGGGGAATTGATGACTCTAGCTACCTGGGTGGG 4310       4320       4330       4340       4350
      TAATAATTTGGAAGATCCAGCATCCAGGGATCTAGTAGTCAATTATGTTA 4360       4370       4380       4390       4400
      ATACTAACATGGGTTTAAAGATCAGGCAACTATTGTGGTTTCATATATCT 4410       4420       4430       4440       4450
      TGCCTTACTTTTGGAAGAGAGACTGTACTTGAATATTTGGTCTCTTTCGG 4460       4470       4480       4490
      AGTGTGGATTCGCACTCCTCCAGCCTATAGACCACCAAATGCCCCT
```

Figure 14F

SEQUENCE LISTING

<160> NUMBER OF SEQ ID NOS: 23

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 1
gcctcatttt gtgggtcacc ata                                        23

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 2
tctctgacat actttccaat                                            20

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:Primer

<400> SEQUENCE: 3
tgcacgattc ctgctcaa                                              18

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 4
tttctcaaag gtggagacag                                            20

<210> SEQ ID NO 5
<211> LENGTH: 181
<212> TYPE: PRT
<213> ORGANISM: Artificial Sequence
<220> FEATURE:
<223> OTHER INFORMATION: Description of Artificial Sequence:Reference
      HBV (Formula I)
<220> FEATURE:
<221> NAME/KEY: variant
<222> LOCATION: (2)..(2)
<223> OTHER INFORMATION: X = N or D
<220> FEATURE:
<221> NAME/KEY: variant
<222> LOCATION: (17)..(17)
<223> OTHER INFORMATION: X = I or P
<220> FEATURE:
<221> NAME/KEY: variant
<222> LOCATION: (29)..(29)
<223> OTHER INFORMATION: X = I or V
<220> FEATURE:
<221> NAME/KEY: variant
<222> LOCATION: (35)..(35)
<223> OTHER INFORMATION: X = S or D
<220> FEATURE:
<221> NAME/KEY: variant
<222> LOCATION: (44)..(44)

```
<223> OTHER INFORMATION: X = T or N
<220> FEATURE:
<221> NAME/KEY: variant
<222> LOCATION: (46)..(46)
<223> OTHER INFORMATION: X = R or N
<220> FEATURE:
<221> NAME/KEY: variant
<222> LOCATION: (47)..(47)
<223> OTHER INFORMATION: X = N or I
<220> FEATURE:
<221> NAME/KEY: variant
<222> LOCATION: (48)..(48)
<223> OTHER INFORMATION: X = any amino acid
<220> FEATURE:
<221> NAME/KEY: variant
<222> LOCATION: (49)..(49)
<223> OTHER INFORMATION: X = N
<220> FEATURE:
<221> NAME/KEY: variant
<222> LOCATION: (50)..(50)
<223> OTHER INFORMATION: X = N or Y or H
<220> FEATURE:
<221> NAME/KEY: variant
<222> LOCATION: (52)..(52)
<223> OTHER INFORMATION: X = H or Y
<220> FEATURE:
<221> NAME/KEY: variant
<222> LOCATION: (53)..(53)
<223> OTHER INFORMATION: X = G or R
<220> FEATURE:
<221> NAME/KEY: variant
<222> LOCATION: (54)..(56)
<223> OTHER INFORMATION: X = any amino acid
<220> FEATURE:
<221> NAME/KEY: variant
<222> LOCATION: (57)..(57)
<223> OTHER INFORMATION: X = D or N
<220> FEATURE:
<221> NAME/KEY: variant
<222> LOCATION: (60)..(60)
<223> OTHER INFORMATION: X = D or N
<220> FEATURE:
<221> NAME/KEY: variant
<222> LOCATION: (61)..(61)
<223> OTHER INFORMATION: X = S or Y
<220> FEATURE:
<221> NAME/KEY: variant
<222> LOCATION: (65)..(65)
<223> OTHER INFORMATION: X = N or Q
<220> FEATURE:
<221> NAME/KEY: variant
<222> LOCATION: (71)..(71)
<223> OTHER INFORMATION: X = L or M
<220> FEATURE:
<221> NAME/KEY: variant
<222> LOCATION: (75)..(75)
<223> OTHER INFORMATION: X = K or Q
<220> FEATURE:
<221> NAME/KEY: variant
<222> LOCATION: (77)..(77)
<223> OTHER INFORMATION: X = Y or F
<220> FEATURE:
<221> NAME/KEY: variant
<222> LOCATION: (79)..(79)
<223> OTHER INFORMATION: X = R or W
<220> FEATURE:
<221> NAME/KEY: variant
<222> LOCATION: (84)..(84)
<223> OTHER INFORMATION: X = Y or L
<220> FEATURE:
<221> NAME/KEY: variant
<222> LOCATION: (85)..(85)
<223> OTHER INFORMATION: X = S or A
<220> FEATURE:
<221> NAME/KEY: variant
<222> LOCATION: (89)..(89)
<223> OTHER INFORMATION: X = I or V
<220> FEATURE:
<221> NAME/KEY: variant
```

-continued

```
<222> LOCATION: (95)..(95)
<223> OTHER INFORMATION: X = I  or L
<220> FEATURE:
<221> NAME/KEY: variant
<222> LOCATION: (99)..(99)
<223> OTHER INFORMATION: X = V or G
<220> FEATURE:
<221> NAME/KEY: variant
<222> LOCATION: (114)..(114)
<223> OTHER INFORMATION: X = C or L
<220> FEATURE:
<221> NAME/KEY: variant
<222> LOCATION: (115)..(115)
<223> OTHER INFORMATION: X = A or S
<220> FEATURE:
<221> NAME/KEY: variant
<222> LOCATION: (116)..(116)
<223> OTHER INFORMATION: X = V or M
<220> FEATURE:
<221> NAME/KEY: variant
<222> LOCATION: (117)..(117)
<223> OTHER INFORMATION: X = V or T
<220> FEATURE:
<221> NAME/KEY: variant
<222> LOCATION: (118)..(118)
<223> OTHER INFORMATION: X = R or C
<220> FEATURE:
<221> NAME/KEY: variant
<222> LOCATION: (122)..(122)
<223> OTHER INFORMATION: X = F or P
<220> FEATURE:
<221> NAME/KEY: variant
<222> LOCATION: (125)..(125)
<223> OTHER INFORMATION: X = L or V
<220> FEATURE:
<221> NAME/KEY: variant
<222> LOCATION: (126)..(126)
<223> OTHER INFORMATION: X = A or V
<220> FEATURE:
<221> NAME/KEY: variant
<222> LOCATION: (128)..(128)
<223> OTHER INFORMATION: X = S or A
<220> FEATURE:
<221> NAME/KEY: variant
<222> LOCATION: (133)..(133)
<223> OTHER INFORMATION: X = V or L or M
<220> FEATURE:
<221> NAME/KEY: variant
<222> LOCATION: (138)..(138)
<223> OTHER INFORMATION: X = K or R
<220> FEATURE:
<221> NAME/KEY: variant
<222> LOCATION: (139)..(139)
<223> OTHER INFORMATION: X = S or T
<220> FEATURE:
<221> NAME/KEY: variant
<222> LOCATION: (140)..(140)
<223> OTHER INFORMATION: X = V or G
<220> FEATURE:
<221> NAME/KEY: variant
<222> LOCATION: (141)..(141)
<223> OTHER INFORMATION: X = Q or E
<220> FEATURE:
<221> NAME/KEY: variant
<222> LOCATION: (143)..(143)
<223> OTHER INFORMATION: X = L or S or R
<220> FEATURE:
<221> NAME/KEY: variant
<222> LOCATION: (145)..(145)
<223> OTHER INFORMATION: X = S or F
<220> FEATURE:
<221> NAME/KEY: variant
<222> LOCATION: (147)..(147)
<223> OTHER INFORMATION: X = F or Y
<220> FEATURE:
<221> NAME/KEY: variant
<222> LOCATION: (148)..(148)
<223> OTHER INFORMATION: X = T or A
<220> FEATURE:
```

```
<221> NAME/KEY: variant
<222> LOCATION: (149)..(149)
<223> OTHER INFORMATION: X = A or S
<220> FEATURE:
<221> NAME/KEY: variant
<222> LOCATION: (150)..(150)
<223> OTHER INFORMATION: X = V or I
<220> FEATURE:
<221> NAME/KEY: variant
<222> LOCATION: (151)..(151)
<223> OTHER INFORMATION: X = T or C
<220> FEATURE:
<221> NAME/KEY: variant
<222> LOCATION: (152)..(152)
<223> OTHER INFORMATION: X = F or V
<220> FEATURE:
<221> NAME/KEY: variant
<222> LOCATION: (153)..(153)
<223> OTHER INFORMATION: X = F or V
<220> FEATURE:
<221> NAME/KEY: variant
<222> LOCATION: (156)..(156)
<223> OTHER INFORMATION: X = S or D
<220> FEATURE:
<221> NAME/KEY: variant
<222> LOCATION: (157)..(157)
<223> OTHER INFORMATION: X = L or V
<220> FEATURE:
<221> NAME/KEY: variant
<222> LOCATION: (162)..(162)
<223> OTHER INFORMATION: X = N
<220> FEATURE:
<221> NAME/KEY: variant
<222> LOCATION: (164)..(165)
<223> OTHER INFORMATION: X = N or Q
<220> FEATURE:
<221> NAME/KEY: variant
<222> LOCATION: (174)..(174)
<223> OTHER INFORMATION: X = N
<220> FEATURE:
<221> NAME/KEY: variant
<222> LOCATION: (179)..(179)
<223> OTHER INFORMATION: X = V or I

<400> SEQUENCE: 5

Ser Xaa Leu Ser Trp Leu Ser Leu Asp Val Ser Ala Ala Phe Tyr His
1               5                   10                  15

Xaa Pro Leu His Pro Ala Ala Met Pro His Leu Leu Xaa Gly Ser Ser
            20                  25                  30

Gly Leu Xaa Arg Tyr Val Ala Arg Leu Ser Ser Xaa Ser Xaa Xaa Xaa
        35                  40                  45

Xaa Xaa Gln Xaa Xaa Xaa Xaa Xaa Xaa Leu His Xaa Xaa Cys Ser Arg
50                  55                  60

Xaa Leu Tyr Val Ser Leu Xaa Leu Leu Tyr Xaa Thr Xaa Gly Xaa Lys
65                  70                  75                  80

Leu His Leu Xaa Xaa His Pro Ile Xaa Leu Gly Phe Arg Lys Xaa Pro
                85                  90                  95

Met Gly Xaa Gly Leu Ser Pro Phe Leu Leu Ala Gln Phe Thr Ser Ala
            100                 105                 110

Ile Xaa Xaa Xaa Xaa Xaa Arg Ala Phe Xaa His Cys Xaa Xaa Phe Xaa
    115                 120                 125

Tyr Met Asp Asp Xaa Val Leu Gly Ala Xaa Xaa Xaa Xaa His Xaa Glu
130                 135                 140

Xaa Leu Xaa Xaa Xaa Xaa Xaa Xaa Leu Leu Xaa Xaa Xaa Gly Ile His
145                 150                 155                 160

Leu Xaa Pro Xaa Lys Thr Lys Arg Trp Gly Tyr Ser Leu Xaa Phe Met
            165                 170                 175
```

```
Gly Tyr Xaa Ile Gly
        180

<210> SEQ ID NO 6
<211> LENGTH: 226
<212> TYPE: PRT
<213> ORGANISM: Artificial Sequence
<220> FEATURE:
<223> OTHER INFORMATION: Description of Artificial Sequence:Reference
      HBV (Formula II)
<220> FEATURE:
<221> NAME/KEY: variant
<222> LOCATION: (2)..(2)
<223> OTHER INFORMATION: X = E or G or D
<220> FEATURE:
<221> NAME/KEY: variant
<222> LOCATION: (3)..(3)
<223> OTHER INFORMATION: X = N or S or K
<220> FEATURE:
<221> NAME/KEY: variant
<222> LOCATION: (4)..(4)
<223> OTHER INFORMATION: X = I or T
<220> FEATURE:
<221> NAME/KEY: variant
<222> LOCATION: (5)..(5)
<223> OTHER INFORMATION: X = T or A
<220> FEATURE:
<221> NAME/KEY: variant
<222> LOCATION: (8)..(8)
<223> OTHER INFORMATION: X = F or L
<220> FEATURE:
<221> NAME/KEY: variant
<222> LOCATION: (10)..(10)
<223> OTHER INFORMATION: X = G or R
<220> FEATURE:
<221> NAME/KEY: variant
<222> LOCATION: (13)..(13)
<223> OTHER INFORMATION: X = L or R
<220> FEATURE:
<221> NAME/KEY: variant
<222> LOCATION: (18)..(18)
<223> OTHER INFORMATION: X = G or V
<220> FEATURE:
<221> NAME/KEY: variant
<222> LOCATION: (19)..(19)
<223> OTHER INFORMATION: X = F or C
<220> FEATURE:
<221> NAME/KEY: variant
<222> LOCATION: (21)..(21)
<223> OTHER INFORMATION: X = L or S or W
<220> FEATURE:
<221> NAME/KEY: variant
<222> LOCATION: (24)..(24)
<223> OTHER INFORMATION: X = R or K
<220> FEATURE:
<221> NAME/KEY: variant
<222> LOCATION: (26)..(26)
<223> OTHER INFORMATION: X = L or R
<220> FEATURE:
<221> NAME/KEY: variant
<222> LOCATION: (27)..(27)
<223> OTHER INFORMATION: X = T or K
<220> FEATURE:
<221> NAME/KEY: variant
<222> LOCATION: (30)..(30)
<223> OTHER INFORMATION: X = Q or K
<220> FEATURE:
<221> NAME/KEY: variant
<222> LOCATION: (31)..(31)
<223> OTHER INFORMATION: X = D or H
<220> FEATURE:
<221> NAME/KEY: variant
<222> LOCATION: (40)..(40)
<223> OTHER INFORMATION: X = N
<220> FEATURE:
<221> NAME/KEY: variant
<222> LOCATION: (44)..(44)
<223> OTHER INFORMATION: X = G or E or A
```

```
-continued

<220> FEATURE:
<221> NAME/KEY: variant
<222> LOCATION: (45)..(45)
<223> OTHER INFORMATION: X = S or A or V or T or L
<220> FEATURE:
<221> NAME/KEY: variant
<222> LOCATION: (46)..(46)
<223> OTHER INFORMATION: X = P or T
<220> FEATURE:
<221> NAME/KEY: variant
<222> LOCATION: (47)..(47)
<223> OTHER INFORMATION: X = V or R or T or K or G
<220> FEATURE:
<221> NAME/KEY: variant
<222> LOCATION: (49)..(49)
<223> OTHER INFORMATION: X = L or P
<220> FEATURE:
<221> NAME/KEY: variant
<222> LOCATION: (51)..(51)
<223> OTHER INFORMATION: X = Q or L or K
<220> FEATURE:
<221> NAME/KEY: variant
<222> LOCATION: (52)..(52)
<223> OTHER INFORMATION: X = N
<220> FEATURE:
<221> NAME/KEY: variant
<222> LOCATION: (53)..(53)
<223> OTHER INFORMATION: X = S or L
<220> FEATURE:
<221> NAME/KEY: variant
<222> LOCATION: (56)..(56)
<223> OTHER INFORMATION: X = P or Q
<220> FEATURE:
<221> NAME/KEY: variant
<222> LOCATION: (57)..(57)
<223> OTHER INFORMATION: X = T or I
<220> FEATURE:
<221> NAME/KEY: variant
<222> LOCATION: (59)..(59)
<223> OTHER INFORMATION: X = N or S
<220> FEATURE:
<221> NAME/KEY: variant
<222> LOCATION: (61)..(61)
<223> OTHER INFORMATION: X = S or L
<220> FEATURE:
<221> NAME/KEY: variant
<222> LOCATION: (63)..(63)
<223> OTHER INFORMATION: X = T or I
<220> FEATURE:
<221> NAME/KEY: variant
<222> LOCATION: (64)..(64)
<223> OTHER INFORMATION: X = S or C
<220> FEATURE:
<221> NAME/KEY: variant
<222> LOCATION: (68)..(68)
<223> OTHER INFORMATION: X = I or T
<220> FEATURE:
<221> NAME/KEY: variant
<222> LOCATION: (70)..(70)
<223> OTHER INFORMATION: X = P or A
<220> FEATURE:
<221> NAME/KEY: variant
<222> LOCATION: (78)..(78)
<223> OTHER INFORMATION: X = R or Q
<220> FEATURE:
<221> NAME/KEY: variant
<222> LOCATION: (85)..(85)
<223> OTHER INFORMATION: X = F or C
<220> FEATURE:
<221> NAME/KEY: variant
<222> LOCATION: (100)..(100)
<223> OTHER INFORMATION: X = Y or C
<220> FEATURE:
<221> NAME/KEY: variant
<222> LOCATION: (105)..(105)
<223> OTHER INFORMATION: X = P or H or S
<220> FEATURE:
<221> NAME/KEY: variant
<222> LOCATION: (110)..(110)
```

-continued

```
<223> OTHER INFORMATION: X = I or L
<220> FEATURE:
<221> NAME/KEY: variant
<222> LOCATION: (112)..(112)
<223> OTHER INFORMATION: X = G or R
<220> FEATURE:
<221> NAME/KEY: variant
<222> LOCATION: (113)..(113)
<223> OTHER INFORMATION: X = S or T
<220> FEATURE:
<221> NAME/KEY: variant
<222> LOCATION: (114)..(114)
<223> OTHER INFORMATION: X = T or S
<220> FEATURE:
<221> NAME/KEY: variant
<222> LOCATION: (118)..(118)
<223> OTHER INFORMATION: X = T or V or A
<220> FEATURE:
<221> NAME/KEY: variant
<222> LOCATION: (119)..(119)
<223> OTHER INFORMATION: X = G or E or Q
<220> FEATURE:
<221> NAME/KEY: variant
<222> LOCATION: (120)..(120)
<223> OTHER INFORMATION: X = P or A or S
<220> FEATURE:
<221> NAME/KEY: variant
<222> LOCATION: (122)..(122)
<223> OTHER INFORMATION: X = K or R
<220> FEATURE:
<221> NAME/KEY: variant
<222> LOCATION: (125)..(125)
<223> OTHER INFORMATION: X = T or M
<220> FEATURE:
<221> NAME/KEY: variant
<222> LOCATION: (126)..(126)
<223> OTHER INFORMATION: X = T or I or S or A
<220> FEATURE:
<221> NAME/KEY: variant
<222> LOCATION: (127)..(127)
<223> OTHER INFORMATION: X = P or T or A or I or L
<220> FEATURE:
<221> NAME/KEY: variant
<222> LOCATION: (128)..(128)
<223> OTHER INFORMATION: X = A or V
<220> FEATURE:
<221> NAME/KEY: variant
<222> LOCATION: (131)..(131)
<223> OTHER INFORMATION: X = N or T
<220> FEATURE:
<221> NAME/KEY: variant
<222> LOCATION: (133)..(133)
<223> OTHER INFORMATION: X = M or K or L
<220> FEATURE:
<221> NAME/KEY: variant
<222> LOCATION: (134)..(134)
<223> OTHER INFORMATION: X = F or Y or I
<220> FEATURE:
<221> NAME/KEY: variant
<222> LOCATION: (136)..(136)
<223> OTHER INFORMATION: X = S or Y
<220> FEATURE:
<221> NAME/KEY: variant
<222> LOCATION: (137)..(137)
<223> OTHER INFORMATION: X = C or S
<220> FEATURE:
<221> NAME/KEY: variant
<222> LOCATION: (140)..(140)
<223> OTHER INFORMATION: X = T or I or S
<220> FEATURE:
<221> NAME/KEY: variant
<222> LOCATION: (143)..(143)
<223> OTHER INFORMATION: X = T or S
<220> FEATURE:
<221> NAME/KEY: variant
<222> LOCATION: (144)..(144)
<223> OTHER INFORMATION: X = D or A
<220> FEATURE:
<221> NAME/KEY: variant
```

```
<222> LOCATION: (146)..(146)
<223> OTHER INFORMATION: X = N
<220> FEATURE:
<221> NAME/KEY: variant
<222> LOCATION: (155)..(155)
<223> OTHER INFORMATION: X = S or T
<220> FEATURE:
<221> NAME/KEY: variant
<222> LOCATION: (158)..(158)
<223> OTHER INFORMATION: X = F or L
<220> FEATURE:
<221> NAME/KEY: variant
<222> LOCATION: (159)..(159)
<223> OTHER INFORMATION: X = A or G or V
<220> FEATURE:
<221> NAME/KEY: variant
<222> LOCATION: (160)..(160)
<223> OTHER INFORMATION: X = K or R or T
<220> FEATURE:
<221> NAME/KEY: variant
<222> LOCATION: (161)..(161)
<223> OTHER INFORMATION: X = Y or F
<220> FEATURE:
<221> NAME/KEY: variant
<222> LOCATION: (165)..(165)
<223> OTHER INFORMATION: X = W or G
<220> FEATURE:
<221> NAME/KEY: variant
<222> LOCATION: (166)..(166)
<223> OTHER INFORMATION: X = A or G
<220> FEATURE:
<221> NAME/KEY: variant
<222> LOCATION: (168)..(168)
<223> OTHER INFORMATION: X = V or A
<220> FEATURE:
<221> NAME/KEY: variant
<222> LOCATION: (170)..(170)
<223> OTHER INFORMATION: X = F or L
<220> FEATURE:
<221> NAME/KEY: variant
<222> LOCATION: (174)..(174)
<223> OTHER INFORMATION: X = S or N
<220> FEATURE:
<221> NAME/KEY: variant
<222> LOCATION: (176)..(176)
<223> OTHER INFORMATION: X = V or A
<220> FEATURE:
<221> NAME/KEY: variant
<222> LOCATION: (177)..(177)
<223> OTHER INFORMATION: X = P or Q
<220> FEATURE:
<221> NAME/KEY: variant
<222> LOCATION: (182)..(182)
<223> OTHER INFORMATION: X = W or C or S
<220> FEATURE:
<221> NAME/KEY: variant
<222> LOCATION: (183)..(183)
<223> OTHER INFORMATION: X = F or C
<220> FEATURE:
<221> NAME/KEY: variant
<222> LOCATION: (184)..(184)
<223> OTHER INFORMATION: X = V or D or A
<220> FEATURE:
<221> NAME/KEY: variant
<222> LOCATION: (185)..(185)
<223> OTHER INFORMATION: X = G or E
<220> FEATURE:
<221> NAME/KEY: variant
<222> LOCATION: (187)..(187)
<223> OTHER INFORMATION: X = S or F
<220> FEATURE:
<221> NAME/KEY: variant
<222> LOCATION: (189)..(189)
<223> OTHER INFORMATION: X = T or I
<220> FEATURE:
<221> NAME/KEY: variant
<222> LOCATION: (192)..(192)
<223> OTHER INFORMATION: X = L or P
<220> FEATURE:
```

```
<221> NAME/KEY: variant
<222> LOCATION: (193)..(193)
<223> OTHER INFORMATION: X = S or L
<220> FEATURE:
<221> NAME/KEY: variant
<222> LOCATION: (194)..(194)
<223> OTHER INFORMATION: X = A or V
<220> FEATURE:
<221> NAME/KEY: variant
<222> LOCATION: (197)..(197)
<223> OTHER INFORMATION: X = M or I
<220> FEATURE:
<221> NAME/KEY: variant
<222> LOCATION: (198)..(198)
<223> OTHER INFORMATION: X = M or I
<220> FEATURE:
<221> NAME/KEY: variant
<222> LOCATION: (200)..(200)
<223> OTHER INFORMATION: X = Y or F
<220> FEATURE:
<221> NAME/KEY: variant
<222> LOCATION: (202)..(202)
<223> OTHER INFORMATION: X = G or E
<220> FEATURE:
<221> NAME/KEY: variant
<222> LOCATION: (204)..(204)
<223> OTHER INFORMATION: X = S or N or K
<220> FEATURE:
<221> NAME/KEY: variant
<222> LOCATION: (205)..(205)
<223> OTHER INFORMATION: X = L or Q
<220> FEATURE:
<221> NAME/KEY: variant
<222> LOCATION: (206)..(206)
<223> OTHER INFORMATION: X = Y or F or H or C
<220> FEATURE:
<221> NAME/KEY: variant
<222> LOCATION: (207)..(207)
<223> OTHER INFORMATION: X = S or G or N or D or T
<220> FEATURE:
<221> NAME/KEY: variant
<222> LOCATION: (209)..(209)
<223> OTHER INFORMATION: X = V or L
<220> FEATURE:
<221> NAME/KEY: variant
<222> LOCATION: (210)..(210)
<223> OTHER INFORMATION: X = S or N
<220> FEATURE:
<221> NAME/KEY: variant
<222> LOCATION: (213)..(213)
<223> OTHER INFORMATION: X = I or M or L
<220> FEATURE:
<221> NAME/KEY: variant
<222> LOCATION: (220)..(220)
<223> OTHER INFORMATION: X = F or C
<220> FEATURE:
<221> NAME/KEY: variant
<222> LOCATION: (221)..(221)
<223> OTHER INFORMATION: X = C or Y
<220> FEATURE:
<221> NAME/KEY: variant
<222> LOCATION: (223)..(223)
<223> OTHER INFORMATION: X = W or R
<220> FEATURE:
<221> NAME/KEY: variant
<222> LOCATION: (224)..(224)
<223> OTHER INFORMATION: X = V or A
<220> FEATURE:
<221> NAME/KEY: variant
<222> LOCATION: (225)..(225)
<223> OTHER INFORMATION: X = Y or I or S

<400> SEQUENCE: 6

Met Xaa Xaa Xaa Xaa Ser Gly Xaa Leu Xaa Pro Leu Xaa Val Leu Gln
 1               5                  10                  15

Ala Xaa Xaa Phe Xaa Leu Thr Xaa Ile Xaa Xaa Ile Pro Xaa Ser Leu
            20                  25                  30
```

```
Xaa Ser Trp Trp Thr Ser Leu Xaa Phe Leu Gly Xaa Xaa Xaa Xaa Cys
     35                  40                  45

Xaa Gly Xaa Xaa Xaa Gln Ser Xaa Xaa Ser Xaa His Xaa Pro Xaa Xaa
 50                  55                  60

Cys Pro Pro Xaa Cys Xaa Gly Tyr Arg Trp Met Cys Leu Xaa Arg Phe
 65              70                  75                  80

Ile Ile Phe Leu Xaa Ile Leu Leu Leu Cys Leu Ile Phe Leu Leu Val
                 85                  90                  95

Leu Leu Asp Xaa Gln Gly Met Leu Xaa Val Cys Pro Leu Xaa Pro Xaa
             100                 105                 110

Xaa Xaa Thr Thr Ser Xaa Xaa Xaa Cys Xaa Thr Cys Xaa Xaa Xaa Xaa
         115                 120                 125

Gln Gly Xaa Ser Xaa Xaa Pro Xaa Xaa Cys Cys Xaa Lys Pro Xaa Xaa
         130                 135                 140

Gly Xaa Cys Thr Cys Ile Pro Ile Pro Ser Xaa Trp Ala Xaa Xaa Xaa
145             150                 155                 160

Xaa Leu Trp Glu Xaa Xaa Ser Xaa Arg Xaa Ser Trp Leu Xaa Leu Leu
             165                 170                 175

Xaa Xaa Phe Val Gln Xaa Xaa Xaa Xaa Leu Xaa Pro Xaa Val Trp Xaa
             180                 185                 190

Xaa Xaa Ile Trp Xaa Xaa Trp Xaa Trp Xaa Pro Xaa Xaa Xaa Xaa Ile
         195                 200                 205

Xaa Xaa Pro Phe Xaa Pro Leu Leu Pro Ile Phe Xaa Xaa Leu Xaa Xaa
 210                 215                 220

Xaa Ile
225

<210> SEQ ID NO 7
<211> LENGTH: 261
<212> TYPE: DNA
<213> ORGANISM: Artificial Sequence
<220> FEATURE:
<223> OTHER INFORMATION: Description of Artificial Sequence:Nucleotide
      Sequence encoding the HBsAg from a reference HBV.
<220> FEATURE:
<221> NAME/KEY: variant
<222> LOCATION: (3)..(3)
<223> OTHER INFORMATION: N = A or C
<220> FEATURE:
<221> NAME/KEY: variant
<222> LOCATION: (10)..(10)
<223> OTHER INFORMATION: N = T or A
<220> FEATURE:
<221> NAME/KEY: variant
<222> LOCATION: (11)..(11)
<223> OTHER INFORMATION: N = C or T
<220> FEATURE:
<221> NAME/KEY: variant
<222> LOCATION: (15)..(15)
<223> OTHER INFORMATION: N = C or T
<220> FEATURE:
<221> NAME/KEY: variant
<222> LOCATION: (21)..(21)
<223> OTHER INFORMATION: N = C or T
<220> FEATURE:
<221> NAME/KEY: variant
<222> LOCATION: (27)..(27)
<223> OTHER INFORMATION: N = C or T
<220> FEATURE:
<221> NAME/KEY: variant
<222> LOCATION: (45)..(45)
<223> OTHER INFORMATION: N = A or G
<220> FEATURE:
<221> NAME/KEY: variant
<222> LOCATION: (48)..(48)
```

```
<223> OTHER INFORMATION: N = T or C
<220> FEATURE:
<221> NAME/KEY: variant
<222> LOCATION: (59)..(59)
<223> OTHER INFORMATION: N = C or G
<220> FEATURE:
<221> NAME/KEY: variant
<222> LOCATION: (61)..(61)
<223> OTHER INFORMATION: N = G or A
<220> FEATURE:
<221> NAME/KEY: variant
<222> LOCATION: (65)..(65)
<223> OTHER INFORMATION: N = T or A
<220> FEATURE:
<221> NAME/KEY: variant
<222> LOCATION: (76)..(76)
<223> OTHER INFORMATION: N = T or G
<220> FEATURE:
<221> NAME/KEY: variant
<222> LOCATION: (86)..(86)
<223> OTHER INFORMATION: N = T or C
<220> FEATURE:
<221> NAME/KEY: variant
<222> LOCATION: (96)..(96)
<223> OTHER INFORMATION: N = C or T
<220> FEATURE:
<221> NAME/KEY: variant
<222> LOCATION: (134)..(134)
<223> OTHER INFORMATION: N = T or C
<220> FEATURE:
<221> NAME/KEY: variant
<222> LOCATION: (153)..(153)
<223> OTHER INFORMATION: N = T or C
<220> FEATURE:
<221> NAME/KEY: variant
<222> LOCATION: (164)..(164)
<223> OTHER INFORMATION: N = T or C
<220> FEATURE:
<221> NAME/KEY: variant
<222> LOCATION: (182)..(182)
<223> OTHER INFORMATION: N = A or T
<220> FEATURE:
<221> NAME/KEY: variant
<222> LOCATION: (203)..(203)
<223> OTHER INFORMATION: N = A or G
<220> FEATURE:
<221> NAME/KEY: variant
<222> LOCATION: (208)..(208)
<223> OTHER INFORMATION: N = T or G
<220> FEATURE:
<221> NAME/KEY: variant
<222> LOCATION: (220)..(220)
<223> OTHER INFORMATION: N = A or T
<220> FEATURE:
<221> NAME/KEY: variant
<222> LOCATION: (222)..(222)
<223> OTHER INFORMATION: N = A or G
<220> FEATURE:
<221> NAME/KEY: variant
<222> LOCATION: (225)..(225)
<223> OTHER INFORMATION: N = T or G
<220> FEATURE:
<221> NAME/KEY: variant
<222> LOCATION: (228)..(228)
<223> OTHER INFORMATION: N = A or G
<220> FEATURE:
<221> NAME/KEY: variant
<222> LOCATION: (243)..(243)
<223> OTHER INFORMATION: N = T or C
<220> FEATURE:
<221> NAME/KEY: variant
<222> LOCATION: (249)..(249)
<223> OTHER INFORMATION: N = T or C
<220> FEATURE:
<221> NAME/KEY: variant
<222> LOCATION: (254)..(254)
<223> OTHER INFORMATION: N = T or C

<400> SEQUENCE: 7
```

-continued

```
acnaaacctn nggnggaaa ntgcacntgt attcccatcc catcntcntg ggctttcgna      60
anatncctat gggagngggc ctcagnccgt ttctcntggc tcagtttact agtgccattt    120
gttcagtggt tcgnagggct ttcccccact gtntggcttt cagntatatg gatgatgtgg   180
tnttgggggc caagtctgta cancatcntg agtccctttn tnccnctntt accaattttc   240
ttntgtctnt gggnatacat t                                             261
```

```
<210> SEQ ID NO 8
<211> LENGTH: 230
<212> TYPE: PRT
<213> ORGANISM: consensus
<220> FEATURE:
<221> NAME/KEY: misc_feature
<222> LOCATION: (2)..(2)
<223> OTHER INFORMATION: X = N
<220> FEATURE:
<221> NAME/KEY: misc_feature
<222> LOCATION: (49)..(49)
<223> OTHER INFORMATION: X = N
<220> FEATURE:
<221> NAME/KEY: misc_feature
<222> LOCATION: (52)..(52)
<223> OTHER INFORMATION: X = N
<220> FEATURE:
<221> NAME/KEY: misc_feature
<222> LOCATION: (53)..(53)
<223> OTHER INFORMATION: X = N
<220> FEATURE:
<221> NAME/KEY: misc_feature
<222> LOCATION: (55)..(55)
<223> OTHER INFORMATION: X = N
<220> FEATURE:
<221> NAME/KEY: misc_feature
<222> LOCATION: (56)..(56)
<223> OTHER INFORMATION: X = N
<220> FEATURE:
<221> NAME/KEY: misc_feature
<222> LOCATION: (65)..(65)
<223> OTHER INFORMATION: X = N
<220> FEATURE:
<221> NAME/KEY: misc_feature
<222> LOCATION: (69)..(69)
<223> OTHER INFORMATION: X = N
<220> FEATURE:
<221> NAME/KEY: misc_feature
<222> LOCATION: (75)..(75)
<223> OTHER INFORMATION: X = N
<220> FEATURE:
<221> NAME/KEY: misc_feature
<222> LOCATION: (195)..(195)
<223> OTHER INFORMATION: X = N
<220> FEATURE:
<221> NAME/KEY: misc_feature
<222> LOCATION: (209)..(209)
<223> OTHER INFORMATION: X = N
<220> FEATURE:
<221> NAME/KEY: misc_feature
<222> LOCATION: (211)..(211)
<223> OTHER INFORMATION: X = N
<220> FEATURE:
<221> NAME/KEY: misc_feature
<222> LOCATION: (222)..(222)
<223> OTHER INFORMATION: X = N

<400> SEQUENCE: 8
```

```
Ser Xaa Asp Leu Ser Trp Leu Ser Leu Asp Val Ser Ala Ala Phe Tyr
 1               5                  10                  15

His Ile Pro Pro Leu His Pro Ala Ala Met Pro His Leu Leu Ile Val
            20                  25                  30

Gly Ser Ser Gly Leu Ser Asp Arg Tyr Val Ala Arg Leu Ser Ser Thr
        35                  40                  45
```

```
Xaa Ser Arg Xaa Xaa Ile Xaa Xaa Tyr His Gln His Tyr Gly Arg Asp
     50                  55                  60

Xaa Leu His Asp Xaa Ser Tyr Cys Ser Arg Xaa Gln Leu Tyr Val Ser
 65                  70                  75                  80

Leu Leu Met Leu Leu Tyr Lys Gln Thr Tyr Phe Gly Arg Trp Lys Leu
                 85                  90                  95

His Leu Tyr Leu Ser Ala His Pro Ile Ile Val Leu Gly Phe Arg Lys
            100                 105                 110

Ile Leu Pro Met Gly Val Gly Leu Ser Pro Phe Leu Leu Ala Gln
            115                 120                 125

Phe Thr Ser Ala Ile Cys Leu Ala Ser Val Met Val Thr Arg Cys Arg
    130                 135                 140

Ala Phe Phe Pro His Cys Leu Val Ala Val Phe Ser Ala Tyr Met Asp
145                 150                 155                 160

Asp Val Leu Met Val Leu Gly Ala Lys Arg Ser Thr Val Gly Gln Glu
                165                 170                 175

His Leu Ser Arg Glu Ser Phe Leu Phe Tyr Thr Ala Ala Ser Val Ile
            180                 185                 190

Thr Cys Xaa Ser Phe Val Leu Leu Ser Asp Leu Val Gly Ile His Leu
        195                 200                 205

Xaa Pro Xaa Gln Lys Thr Lys Arg Trp Gly Tyr Ser Leu Xaa Phe Met
    210                 215                 220

Gly Tyr Val Ile Ile Gly
225                 230

<210> SEQ ID NO 9
<211> LENGTH: 426
<212> TYPE: DNA
<213> ORGANISM: HBV

<400> SEQUENCE: 9
atcctgctgc tatgcctcat cttcttgttg gttcttctgg actaccaagg tatgttgtct    60
gtttgtcctc tacttccaag aacatcaact accagcacgg gaccatgcaa gacctgcacg   120
attcctgctc aaggaacctc tatgtttccc tcttcttgct gtacaaaacc ttcggacgga   180
aactgcactt gtattcccat ccatcatct tgggctttcg caagattcct atggagtgg    240 gcctcagtcc gtttctcctg gctcagttta ctagtgccat tgttcagtg gttcgtaggg    300 cttttccccca ctgtttggct ttcagttata tggatgatgt ggtattgggg gccaagtctg   360
tacaacatct tgagtccctt tttacctcta ttaccaattt tcttttgtct ttgggtatac    420
atttga                                                              426

<210> SEQ ID NO 10
<211> LENGTH: 425
<212> TYPE: DNA
<213> ORGANISM: HBV

<400> SEQUENCE: 10
atcctgctgc tatgcctcat cttcttgttg gttcttctgg actatcaagg tatgttgccc    60
gtttgtcctc taattccagg atcatcaacc accagcacag gaccatgcaa aacctgcacg   120
actcctgctc aaggaacctc tatgtttccc tcatgttgct gtacaaaacc tacggacgga   180
aactgcacct gtattcccat ccatcatct tgggctttcg caaaatacct atggagtgg    240 gcctcagtcc gtttctcttg gctcagttta ctagtgccat tgttcagtg gttcgtaggg    300
```

```
ctttccccca ctgtctggct tcagttata tggatgatgt ggttttgggg gccaagtctg    360
tacaacatct tgagtccctt tatgccgctg ttaccaattt tcttttgtct ttgggtatac    420
attta                                                                425

<210> SEQ ID NO 11
<211> LENGTH: 426
<212> TYPE: DNA
<213> ORGANISM: HBV

<400> SEQUENCE: 11
atcctgctgc tatgcctcat cttcttgttg gttcttctgg actaccaagg tatgttgccc     60
gtttgtcctc tacttccagg aacatcaact accagcacgg gaccatgcaa gacctgcacg    120
attcctgctc aaggaacctc tatgtttccc tcttgttggt gtacaaaacc ttcgacgga    180 aactgcactt gtattcccat cccatcatcc tgggctttcg caagattcct atgggagtgg    240
gcctcagtcc gtttctcctg gctcagttta ctagtgccat tgttcagtg gttcgcaggg    300 ctttccccca ctgtttggct tcagttata tggatgatgt ggtattgggg gccaagtctg    360
tacaacatct tgagtccctt tttacctcta ttaccaattt tcttttgtct ttgggtatac    420
atttga                                                               426

<210> SEQ ID NO 12
<211> LENGTH: 426
<212> TYPE: DNA
<213> ORGANISM: HBV

<400> SEQUENCE: 12
atcctgctgc tatgcctcat cttcttgttg gttcttctgg actatcaagg tatgttgccc     60
gtttgtcctc taattccagg atcttcaact accagcacgg gaccatgcag aacctgcacg    120
actcctgctc aaggaacctc tatgtatccc tcctgttgct gtaccaaacc ttcgacgga    180 aattgcacct gtattcccat cccatcatcc tgggctttcg gaaaattcct atgggagtgg    240
gcctcagccc gtttctcctg gctcagttta ctagtgccat tgttcagtg gttcgtaggg    300 ctttccccca ctgtttggct tcagttata tggatgatgt ggtattgggg gccaagtctg    360
tacagcatct tgagtccctt tttaccgctg ttaccaattt tcttctgtct ttgggtatac    420
atttaa                                                               426

<210> SEQ ID NO 13
<211> LENGTH: 426
<212> TYPE: DNA
<213> ORGANISM: HBV

<400> SEQUENCE: 13
atcctgctgc tatgcctcat cttcttgttg gttcttctgg actatcaagg tatgttgccc     60
gtttgtcctc taattccagg atcttcaaca accagcacgg gaccatgcag aacctgcacg    120
actcctgctc aaggaacctc tatgtatccc tcctgttgct gtaccaaacc ttcggacgga    180
aattgcacct gtattcccat cccatcatct tgggctttcg gaaaattcct atgggagtgg    240
gcctcagccc gtttctcctg gctcagttta ctagtgccat tgttcagtg gttcgtaggg    300 ctttccccca ctgtttggct tcagttata tggatgatgt ggtattgggg gccaagtctg    360
tacagcatct tgagtccctt tttaccgctg ttaccaattt tcttttgtct ctgggtatac    420
atttaa                                                               426
```

<210> SEQ ID NO 14
<211> LENGTH: 426
<212> TYPE: DNA
<213> ORGANISM: HBV

<400> SEQUENCE: 14

```
atcctgctgc tatgcctcat cttcttgttg gttcttctgg actatcaagg tatgttgccc      60
gtttgtcctc taattccagg atcctcaacc accagcacgg gaccatgccg aacctgcacg     120
actcctgctc aaggaacctc tatgtatccc tcctgttgct gtaccaaacc ttcggacgga     180
aattgcacct gtattcccat ccatcatcc tgggctttcg gaaaattcct atgggagtgg      240
gcctcagccc gtttctcctg gctcagttta ctagtgccat tgttcagtg gttcgtaggg      300
ctttcccca ctgtttggct ttcagttata tggatgatgt ggtattgggg gccaagtctg      360
tacagcatct tgagtccctt tttaccgctg ttaccaattt tcttttgtct ttgggtatac     420
atttaa                                                                 426
```

<210> SEQ ID NO 15
<211> LENGTH: 426
<212> TYPE: DNA
<213> ORGANISM: HBV

<400> SEQUENCE: 15

```
atcctgctgc tatgcctcat cttcttattg gttcttctgg attatcaagg tatgttgccc      60
gtttgtcctc taattccagg atcaacaaca accagtacgg gaccatgcaa aacctgcacg     120
actcctgctc aaggcaactc tatgtttccc tcatgttgct gtacaaaacc tacggatgga     180
aattgcacct gtattcccat ccatcgtcc tgggctttcg caaataccct atgggagtgg      240
gcctcagtcc gtttctcttg gctcagttta ctagtgccat tgttcagtg gttcgtaggg      300
ctttcccca ctgtttggct ttcagctata tggatgatgt ggtattgggg gccaagtctg      360
tacagcatcg tgagtccctt tataccgctg ttaccaattt tcttttgtct ctgggtatac     420
atttaa                                                                 426
```

<210> SEQ ID NO 16
<211> LENGTH: 426
<212> TYPE: DNA
<213> ORGANISM: HBV

<400> SEQUENCE: 16

```
atcctgctgc tatgcctcat cttcttgttg gttcttctgg actaccaagg tatgttgccc      60
gtttgtcctc tacttccagg aacatcaacc accagcacgg gaccatgcaa gacctgcacg     120
attcctgctc aaggaacctc tatgtttccc tcttgttgct gtacaaaacc ttcggacgga     180
aactgcactt gtattcccat ccatcatcc tgggctttcg caagattcct atgggagggg      240
gcctcagtcc gtttctcctg gctcagttta ctagtgccat tgttcagtg gttcgtaggg      300
ctttcccca ctgtttggct ttcagttata tggatgatgt ggtattgggg gccaagtctg      360
tacaacatct tgagtccctt tttacctcta ttaccaattt tcttttgtct ttgggtatac     420
atttga                                                                 426
```

<210> SEQ ID NO 17
<211> LENGTH: 426
<212> TYPE: DNA
<213> ORGANISM: HBV

<400> SEQUENCE: 17

| | |
|---|---:|
| atcctgctgc tatgcctcat cttcttgttg gttcttctgg actaccaagg tatgttgccc | 60 |
| gtttgtcctc tacttccagg aacatcaact accagcacgg gaccatgcaa gacctgcacg | 120 |
| attcctgctc aaggaacctc tatgtttccc tcttgttgct gtacaaaacc ttcggacgga | 180 |
| aactgcactt gtattcccat cccatcatcc tgggctttcg caagattcct atgggagggg | 240 |
| gcctcagtcc gtttctcctg gctcagttta ctagtgccat tgttcagtg gttcgtaggg | 300 |
| cttttccccca ctgtttggct ttcagttata tggatgatgt ggtattgggg gccaagtctg | 360 |
| tacaacatct tgagtccctt tttacctcta ttaccaattt tcttttgtct ttgggtatac | 420 |
| atttaa | 426 |

<210> SEQ ID NO 18
<211> LENGTH: 426
<212> TYPE: DNA
<213> ORGANISM: HBV

<400> SEQUENCE: 18

| | |
|---|---:|
| atcctgctgc tatgcctcat cttcttgttg gttcttctgg actatcaagg tatgttgccc | 60 |
| gtttgtcctc taattccagg atcctcaaca accagcacgg gaccatgccg gacctgcatg | 120 |
| actactgctc aaggaacctc tatgtatccc tcctgttgct gtaccaaacc ttcggacgga | 180 |
| aattgcacct gtattcccat cccatcatcc tgggctttcg gaaaattcct atgggagtgg | 240 |
| gcctcagccc gtttctcctg gctcagttta ctagtgccat tgttcagtg gttcgtaggg | 300 |
| cttttccccca ctgtttggct ttcagttata tggatgatgt ggtattgggg gccaagtctg | 360 |
| tacagcatct tgagtccctt tttaccgctg ttaccaattt tcttttgtct ttgggtatac | 420 |
| atttaa | 426 |

<210> SEQ ID NO 19
<211> LENGTH: 426
<212> TYPE: DNA
<213> ORGANISM: HBV

<400> SEQUENCE: 19

| | |
|---|---:|
| atcctgctgc tatgcctcat cttcttgttg gttcttctgg actatcaagg tatgttgccc | 60 |
| gtttgtcctc taattccagg atcttcaacc accagcacgg gaccatgcag gacctgcacg | 120 |
| actcctgctc aaggcaactc tatgtatccc tcctgttgct gtaccaaacc ttcggacgga | 180 |
| aattgcacct gtattcccat cccatcatct tgggctttcg gaaaattcct atgggagtgg | 240 |
| gcctcagccc gtttctcctg gctcagttta ctagtgccat tgttcagtg gttcgtaggg | 300 |
| cttttccccca ctgtttggct ttcagttata tggatgatgt ggtattgggg gccaagtctg | 360 |
| tacagcatct tgagtccctt tttaccgctg ttaccaattt tcttttgtct ttgggcatac | 420 |
| atttaa | 426 |

<210> SEQ ID NO 20
<211> LENGTH: 426
<212> TYPE: DNA
<213> ORGANISM: HBV

<400> SEQUENCE: 20

| | |
|---|---:|
| atcctgctgc tatgcctcat cttcttgttg gttcttctgg actatcaagg tatgttgccc | 60 |
| gtttgtcctc taattccagg atcatcaacc accagcacgg gaccatgcaa gacctgcaca | 120 |
| actcctgctc aaggaacctc tatgtttccc tcatgttgct gtacaaaacc tatggatgga | 180 |
| aactgcacct gtattcccat cccatcatct tgggctttcg caaaatacct atgggagtgg | 240 |

```
gcctcagtcc gtttctcttg gctcagttta ctagtgccat tgttcagtg gttcgtaggg      300 ctttcccca ctgtctggct ttcagttata tggatgatgt ggtattgggg gccaagtctg      360
tacaacatct tgagtccctt tatgccgctg ttaccaattt tcttttgtct ttgggtatac      420
atttaa                                                                426

<210> SEQ ID NO 21
<211> LENGTH: 4084
<212> TYPE: DNA
<213> ORGANISM: HBV 1.28 genome

<400> SEQUENCE: 21
ggacgacccc tcgcggggcc gcttgggact ctctcgtccc cttctccgtc tgccgttcca       60
gccgaccacg gggcgcacct ctctttacgc ggtctcccccg tctgtgcctt ctcatctgcc      120
ggtccgtgtg cacttcgctt cacctctgca cgttgcatgg agaccaccgt gaacgcccat      180
cagatcctgc ccaaggtctt acataagagg actcttggac tcccagcaat gtcaacgacc      240
gaccttgagg cctacttcaa agactgtgtg tttaaggact gggaggagct ggggaggag       300 attaggttaa aggtctttgt attaggaggc tgtaggcata aattggtctg cgcaccagca      360
ccatgcaact ttttcacctc tgcctaatca tctcttgtac atgtcccact gttcaagcct      420
ccaagctgtg ccttgggtgg ctttgggca tggacattga cccttataaa gaatttggag       480
ctactgtgga gttactctcg ttttttgcctt ctgacttctt ccttccgtc agagatctcc      540 tagacaccgc ctcagctctg tatcgagaag ccttagagtc cctgagcat tgctcacctc       600 accatactgc actcaggcaa gccattctct gctgggggga attgatgact ctagctacct      660
gggtgggtaa taatttggaa gatccagcat ccagggatct agtagtcaat tatgttaata      720
ctaacatggg tttaaagatc aggcaactat tgtggtttca tatatcttgc cttacttttg      780
gaagagagac tgtacttgaa tatttggtct ctttcggagt gtggattcgc actcctccag      840
cctatagacc accaaatgcc cctatcttat caacacttcc ggaaactact gttgttagac      900
gacgggaccc aggcaggtcc cctagaagaa gaactccctc gcctcgcaga cgcagatctc      960
aatcgccgcg tcgcagaaga tctcaatctc gggaatctca atgttagtat tccttggact     1020
cataaggtgg gaaactttac ggggctttat tcctctacag tacctatctt taatcctgaa     1080
tggcaaactc cttcctttcc taagattcat ttacaagagg acattattaa taggtgtcaa     1140
caatttgtgg gccctctcac tgtaaatgaa aagagaagat tgaaattaat tatgcctgct     1200
agattctatc ctacccacac taaatatttg cccttagaca aaggaattaa accttattat     1260
ccagatcagg tagttaatca ttacttccaa accagacatt atttacatac tctttggaag     1320
gctggtattc tatataagag ggaaaccaca cgtagcgcat cattttgcgg gtcaccatat     1380
tcttgggaac aagagctaca gcatgggagg ttggtcatca aaacctcgca aaggcatggg     1440
gacgaatctt tctgttccca accctctggg attctttccc gatcatcagt tggaccctgc     1500
attcggagcc aactcaaaca atccagattg ggacttcaac cccatcaagg accactggcc     1560
agcagccaac caggtaggag tgggagcatt cgggccaggg ctcacccctc cacacggcgg     1620 tatttttgggg tggagccctc aggctcaggg catattgacc acagtgtcaa caattcctcc     1680
tcctgcctcc accaatcggc agtcaggaag gcagcctact cccatctctc cacctctaag     1740
agacagtcat cctcaggcca tgcagtggaa ttccactgcc ttccaccaag ctctgcagga     1800
tcccagagtc agggtctgt atcttcctgc tggtggctcc agttcaggaa cagtaaaccc     1860
```

-continued

```
tgctccgaat attgcctctc acatctcgtc aatctccgcg aggactgggg accctgtgac      1920
gaacatggag aacatcacat caggattcct aggacccctg ctcgtgttac aggcggggtt      1980
tttcttgttg acaagaatcc tcacaatacc gcagagtcta gactcgtggt ggacttctct      2040
caattttcta gggggatctc ccgtgtgtct tggccaaaat tcgcagtccc caacctccaa      2100
tcactcacca acctcctgtc ctccaatttg tcctggttat cgctggatgt gtctgcggcg      2160
ttttatcata ttcctcttca tcctgctgct atgcctcatc ttcttattgg ttcttctgga      2220
ttatcaaggt atgttgcccg tttgtcctct aattccagga tcaacaacaa ccagtacggg      2280
accatgcaaa acctgcacga ctcctgctca aggcaactct atgtttccct catgttgctg      2340
tacaaaacct acggatggaa attgcacctg tattcccatc ccatcgtcct gggctttcgc      2400
aaaataccta tgggagtggg cctcagtccg tttctcttgg ctcagtttac tagtgccatt      2460
tgttcagtgg ttcgtagggc tttcccccac tgtttggctt tcagctatat ggatgatgtg      2520
gtattggggg ccaagtctgt acagcatcgt gagtcccttt ataccgctgt taccaatttt      2580
cttttgtctc tgggtataca tttaaaccct aacaaaacaa aaagatgggg ttattcccta      2640
aacttcatgg gctacataat tggaagttgg ggaactttgc cacaggatca tattgtacaa      2700
aagatcaaac actgttttag aaaacttcct gttaacaggc ctattgattg gaaagtatgt      2760
caaagaattg tgggtctttt gggctttgct gctccattta cacaatgtgg atatcctgcc      2820
ttaatgcctt tgtatgcatg tatacaagct aaacaggctt tcactttctc gccaacttac      2880
aaggcctttc taagtaaaca gtacatgaac ctttaccccg ttgctcggca acggcctggt      2940
ctgtgccaag tgtttgctga cgcaaccccc actggctggg gcttggccat aggccatcag      3000
cgcatgcgtg gaacctttgt ggctcctctg ccgatccata ctgcggaact cctagccgct      3060
tgttttgctc gcagccggtc tggagcaaag ctcatcggaa ctgacaattc tgtcgtcctc      3120
tcgcggaaat atacatcgtt tccatggctg ctaggctgta ctgccaactg gatccttcgc      3180
gggacgtcct ttgtttacgt cccgtcggcg ctgaatcccg cggacgaccc ctcgcggggc      3240
cgcttgggac tctctcgtcc ccttctccgt ctgccgttcc agccgaccac ggggcgcacc      3300
tctctttacg cggtctcccc gtctgtgcct tctcatctgc cggtccgtgt gcacttcgct      3360
tcacctctgc acgttgcatg gagaccaccg tgaacgccca tcagatcctg cccaaggtct      3420
tacataagag gactcttgga ctcccagcaa tgtcaacgac cgaccttgag gcctacttca      3480
aagactgtgt gtttaaggac tgggaggagc tgggggagga gattaggtta aaggtctttg      3540
tattaggagg ctgtaggcat aaattggtct gcgcaccagc accatgcaac tttttcacct      3600
ctgcctaatc atctcttgta catgtcccac tgttcaagcc tccaagctgt gccttgggtg      3660
gctttggggc atggacattg acccttataa agaatttgga gctactgtgg agttactctc      3720
gttttttgcct tctgacttct ttccttccgt cagagatctc ctagacaccg cctcagctct      3780
gtatcgagaa gccttagagt ctcctgagca ttgctcacct caccatactg cactcaggca      3840
agccattctc tgctgggggg aattgatgac tctagctacc tgggtgggta ataatttgga      3900
agatccagca tccagggatc tagtagtcaa ttatgttaat actaacatgg gtttaaagat      3960
caggcaacta ttgtggtttc atatatcttg ccttactttt ggaagagaga ctgtacttga      4020
atatttggtc tctttcggag tgtggattcg cactcctcca gcctatagac caccaaatgc      4080
ccct                                                                   4084
```

```
<210> SEQ ID NO 22
<211> LENGTH: 4496
```

<212> TYPE: DNA
<213> ORGANISM: HBV 1.5 genome

<400> SEQUENCE: 22

```
gatatcctgc cttaatgcct ttgtatgcat gtatacaagc taaacaggct ttcactttct    60
cgccaactta caaggccttt ctaagtaaac agtacatgaa cctttacccc gttgctcggc   120
aacggcctgg tctgtgccaa gtgtttgctg acgcaacccc cactggctgg ggcttggcca   180
taggccatca gcgcatgcgt ggaacctttg tggctcctct gccgatccat actgcggaac   240
tcctagccgc ttgttttgct cgcagccggt ctggagcaaa gctcatcgga actgacaatt   300
ctgtcgtcct ctcgcggaaa tatacatcgt ttccatggct gctaggctgt actgccaact   360
ggatccttcg cgggacgtcc tttgtttacg tcccgtcggc gctgaatccc gcggacgacc   420
cctcgcgggg ccgcttggga ctctctcgtc cccttctccg tctgccgttc cagccgacca   480
cggggcgcac ctctctttac gcggtctccc cgtctgtgcc ttctcatctg ccggtccgtg   540
tgcacttcgc ttcacctctg cacgttgcat ggagaccacc gtgaacgccc atcagatcct   600
gcccaaggtc ttacataaga ggactcttgg actcccagca atgtcaacga ccgaccttga   660
ggcctacttc aaagactgtg tgtttaagga ctggaggag ctgggggagg agattaggtt   720
aaaggtcttt gtattaggag gctgtaggca taaattggtc tgcgcaccag caccatgcaa   780
ctttttcacc tctgcctaat catctcttgt acatgtccca ctgttcaagc ctccaagctg   840
tgccttgggt ggctttgggg catggacatt gacccttata agaatttgg agctactgtg   900
gagttactct cgttttgcc ttctgacttc tttccttccg tcagagatct cctagacacc   960
gcctcagctc tgtatcgaga agccttagag tctcctgagc attgctcacc tcaccatact  1020
gcactcaggc aagccattct ctgctggggg gaattgatga ctctagctac ctgggtgggt  1080
aataatttgg aagatccagc atccagggat ctagtagtca attatgttaa tactaacatg  1140
ggtttaaaga tcaggcaact attgtggttt catatatctt gccttacttt tggaagagag  1200
actgtacttg aatatttggt ctctttcgga gtgtggattc gcactcctcc agcctataga  1260
ccaccaaatg cccctatctt atcaacactt ccggaaacta ctgttgttag acgacgggac  1320
cgaggcaggt cccctagaag aagaactccc tcgcctcgca gacgcagatc tcaatcgccg  1380
cgtcgcagaa gatctcaatc tcgggaatct caatgttagt attccttgga ctcataaggt  1440
gggaaacttt acgggctttt attcctctac agtacctatc tttaatcctg aatggcaaac  1500
tccttccttt cctaagattc atttacaaga ggacattatt aataggtgtc aacaatttgt  1560
gggccctctc actgtaaatg aaaagagaag attgaaatta attatgcctg ctagattcta  1620
tcctacccac actaaatatt tgcccttaga caaggaatt aaaccttatt atccagatca  1680
ggtagttaat cattacttcc aaaccagaca ttatttacat actctttgga aggctggtat  1740
tctatataag agggaaacca cacgtagcgc atcattttgc gggtcaccat attcttggga  1800
acaagagcta cagcatggga ggttggtcat caaaacctcg caaggcatg gggacgaatc  1860
tttctgttcc caaccctctg ggattctttc ccgatcatca gttggaccct gcattcggag  1920
ccaactcaaa caatccagat tgggacttca accccatcaa ggaccactgg ccagcagcca  1980
accaggtagg agtgggagca ttcgggccag ggctcacccc tccacacggc ggtattttgg  2040
ggtggagccc tcaggctcag ggcatattga ccacagtgtc aacaattcct cctcctgcct  2100
ccaccaatcg gcagtcagga aggcagccta ctcccatctc tccacctcta agagacagtc  2160
atcctcaggc catgcagtgg aattccactg ccttccacca agctctgcag gatcccagag  2220
```

```
tcagggtct gtatcttcct gctggtggct ccagttcagg aacagtaaac cctgctccga   2280
atattgcctc tcacatctcg tcaatctccg cgaggactgg ggaccctgtg acgaacatgg   2340
agaacatcac atcaggattc ctaggacccc tgctcgtgtt acaggcgggg tttttcttgt   2400
tgacaagaat cctcacaata ccgcagagtc tagactcgtg gtggacttct ctcaattttc   2460
taggggatc tcccgtgtgt cttggccaaa attcgcagtc cccaacctcc aatcactcac   2520
caacctcctg tcctccaatt tgtcctggtt atcgctggat gtgtctgcgg cgttttatca   2580
tattcctctt catcctgctg ctatgcctca tcttcttatt ggttcttctg gattatcaag   2640
gtatgttgcc cgtttgtcct ctaattccag gatcaacaac aaccagtacg ggaccatgca   2700
aaacctgcac gactcctgct caaggcaact ctatgtttcc ctcatgttgc tgtacaaaac   2760
ctacggatgg aaattgcacc tgtattccca tcccatcgtc ctgggctttc gcaaaatacc   2820
tatgggagtg ggcctcagtc cgtttctctt ggctcagttt actagtgcca tttgttcagt   2880
ggttcgtagg gctttccccc actgtttggc tttcagctat atggatgatg tggtattggg   2940
ggccaagtct gtacagcatc gtgagtccct ttataccgct gttaccaatt ttcttttgtc   3000
tctgggtata catttaaacc ctaacaaaac aaaaagatgg ggttattccc taaacttcat   3060
gggctacata attggaagtt ggggaacttt gccacaggat catattgtac aaaagatcaa   3120
acactgtttt agaaaacttc ctgttaacag gcctattgat tggaaagtat gtcaaagaat   3180
tgtgggtctt ttgggctttg ctgctccatt tacacaatgt ggatatcctg ccttaatgcc   3240
tttgtatgca tgtatacaag ctaaacaggc tttcactttc tcgccaactt acaaggcctt   3300
tctaagtaaa cagtacatga acctttaccc cgttgctcgg caacggcctg gtctgtgcca   3360
agtgtttgct gacgcaaccc ccactggctg gggcttggcc ataggccatc agcgcatgcg   3420
tggaaccttt gtggctcctc tgccgatcca tactgcggaa ctcctagccg cttgttttgc   3480
tcgcagccgg tctggagcaa agctcatcgg aactgacaat tctgtcgtcc tctcgcggaa   3540
atatacatcg tttccatggc tgctaggctg tactgccaac tggatccttc gcgggacgtc   3600
ctttgtttac gtcccgtcgg cgctgaatcc cgcggacgac ccctcgcggg gccgcttggg   3660
actctctcgt ccccttctcc gtctgccgtt ccagccgacc acggggcgca cctctcttta   3720
cgcggtctcc ccgtctgtgc cttctcatct gccggtccgt gtgcacttcg cttcacctct   3780
gcacgttgca tggagaccac cgtgaacgcc catcagatcc tgcccaaggt cttacataag   3840
aggactcttg gactcccagc aatgtcaacg accgaccttg aggcctactt caaagactgt   3900
gtgtttaagg actgggagga gctggggag gagattaggt taaaggtctt tgtattagga   3960
ggctgtaggc ataaattggt ctgcgcacca gcaccatgca actttttcac ctctgcctaa   4020
tcatctcttg tacatgtccc actgttcaag cctccaagct gtgccttggg tggctttggg   4080
gcatggacat tgacccttat aaagaatttg gagctactgt ggagttactc tcgttttgc   4140
cttctgactt ctttccttcc gtcagagatc tcctagacac cgcctcagct ctgtatcgag   4200
aagccttaga gtctcctgag cattgctcac ctcaccatac tgcactcagg caagccattc   4260
tctgctgggg ggaattgatg actctagcta cctgggtggg taataatttg gaagatccag   4320
catccaggga tctagtagtc aattatgtta atactaacat gggtttaaag atcaggcaac   4380
tattgtggtt tcatatatct tgccttactt ttggaagaga gactgtactt gaatatttgg   4440
tctctttcgg agtgtggatt cgcactcctc cagcctatag accaccaaat gccccct      4496
```

<210> SEQ ID NO 23
<211> LENGTH: 119

```
<212> TYPE: PRT
<213> ORGANISM: Artificial Sequence
<220> FEATURE:
<223> OTHER INFORMATION: Description of Artificial Sequence: Amino acid
      sequence of a surface antigen of HBV beginning from amino acid
      position 108.

<400> SEQUENCE: 23

Pro Leu Leu Pro Arg Thr Ser Thr Thr Ser Thr Gly Pro Cys Lys Thr
                 5                  10                  15

Cys Thr Ile Pro Ala Gln Gly Thr Ser Met Phe Pro Ser Ser Cys Cys
             20                  25                  30

Thr Lys Pro Ser Asp Gly Asn Cys Thr Cys Ile Pro Ile Pro Ser Ser
         35                  40                  45

Trp Ala Phe Ala Arg Phe Leu Trp Glu Trp Ala Ser Val Arg Phe Ser
     50                  55                  60

Trp Leu Ser Leu Leu Val Pro Phe Val Gln Trp Phe Val Gly Leu Ser
 65                  70                  75                  80

Pro Thr Val Trp Leu Ser Val Ile Trp Met Met Trp Tyr Trp Gly Pro
                 85                  90                  95

Ser Leu Tyr Asn Ile Leu Ser Pro Phe Leu Pro Leu Leu Pro Ile Phe
             100                 105                 110

Phe Cys Leu Trp Val Tyr Ile
             115
```

METHOD FOR DETECTING VARIANT HBV

CROSS-REFERENCE TO RELATED APPLICATION

This application claims priority from U.S. Provisional Application No. 60/179,948, filed on Feb. 3, 2000.

FIELD OF THE INVENTION

The present invention relates generally to an assay for detecting variant Hepatitis B viruses (HBVs) which exhibit altered sensitivity to agents. The variant HBVs are delivered to cells using a baculovirus vector. The same agents generally have a particular effect or absence of effect on a reference HBV. The altered sensitivity is in relation to the effects of the agent on one or more stages of infection, replication, assembly or release of virus or virus-like particles including any intermediary steps during the processes of viral infection, replication, assembly and/or release. The identification of variant HBVs with altered sensitivities to anti-HBV agents provides a means of monitoring cross resistance, or the development of new therapeutics effective against variant HBVs with altered sensitivities to other anti-HBV agents, as well as monitoring therapeutic protocols which may then need to be modified to ensure the appropriate anti-HBV agent is administered or that the appropriate therapeutic protocol is instituted. The present invention further provides variant HBVs detected by the assay of the present invention and to components thereof as well as recombinant, chemical analogue, homologue and derivative forms of such components.

BACKGROUND OF THE INVENTION

Reference to any prior art in this specification is not, and should not be taken as, an acknowledgment or any form of suggestion that this prior art forms part of the common general knowledge in Australia or any other country.

Bibliographic details of the publications numerically referred to in this specification are collected at the end of the description.

Specific mutations in amino acid sequence are represented herein as "$Xaa_1 n Xaa_2$" where $Xaa_1$ is the original amino acid residue before mutation, n is the residue number and $Xaa_2$ is the mutant amino acid. The abbreviation "Xaa" may be the three letter or single letter amino acid code. A mutation in single letter code is represented, for example, by $X_1 n X_2$ where $X_1$ and $X_2$ are the same as $Xaa_1$ and $Xaa_2$, respectively. The amino acid residues for Hepatitis B virus DNA polymerase are numbered with the residue methionine in the motif "Tyr Met Asp Asp (YMDD)," being residue number 550, wich corresponds to residue number 159 of SEQ ID NO:8.

The reference HBV is considered herein to comprise a composite or consensus nucleotide or amino acid sequence from HBV genotypes A through G (1, 2).

The rapidly increasing sophistication of recombinant DNA technology is greatly facilitating advances in the medical and allied health fields. This is particularly the case with the generation of therapeutic compositions and recombinant vaccines. Recombinant technology is providing the genetic bases for screening or identifying useful components for therapeutic compositions.

Hepatitis B virus (HBV) can cause debilitating disease conditions ranging from subclinical infection to chronic active hepatitis and can lead to acute liver failure or fulminant hepatitis.

Most patients will suffer an acute hepatitis during which time the virus is eliminated. In fulminant hepatitis, patients have acute liver failure and this frequently leads to patient death. About 5% of patients in North America and Europe fail to eliminate the virus, whereas in West Africa, up to 15% of infected patients fail to clear HBV (3). Persistent HBV infection predisposes the host to chronic liver disease and hepatocellular carcinoma (4).

The HBV genome comprises a series of overlapping genes in a circular, partially double-standard DNA molecule (5) [see also FIG. 1]. These genes encode for four overlapping open reading frames. For example, the gene encoding the DNA polymerase overlaps the viral envelope genes (Pre-S1, Pre-S2 and S) and partially overlaps the X and core genes. The protein component of the small HBV surface protein is generally referred to as the HBV surface antigen (HBsAg) and is encoded by the S gene sequence. The Pre-S1 and Pre-S2 gene sequences encode the other envelope components (6). The core open reading frame encodes for both the hepatitis B core protein (HBcAg) and HBeAg, which starts from a precore initiation codon. HBV variants can have single or multiple mutations in one or more of the overlapping genes.

The HBV DNA polymerase is a reverse transcriptase (i.e. an RNA dependent DNA polymerase) and also has DNA dependent DNA polymerase as well as primase and RNase H activity. Nucleoside analogues have been used to inhibit HBV DNA replication. However, mutations have arisen in the gene encoding the HBV DNA polymerase resulting in the development of HBV variants resistant to the nucleoside analogues. Resistance may occur to a single nucleoside analogue or cross-resistance may also occur to an entire family of nucleoside analogues. Furthermore, when the mutation occurs in a region overlapping with the gene encoding HBsAg, alterations may occur to the HBsAg itself leading to the development of vaccine escape mutants.

Some precore variants of HBV result in hepatitis B e antigen (HBeAg)-negative hepatitis B. Seven to 30% of patients with chronic HBV infection worldwide are HBeAg-negative and are positive for HBV DNA by hybridisation using commercial tests. One such variant is unable to synthesize HBeAg. A single base substitution (G-to-A) at nucleotide 1896 ($A_{1896}$; numbering from the unique EcoRI site) gives rise to a translational stop codon in the second last codon (codon 28) of the precore gene. Other precore and basal core promoter (BCP) mutations are listed in Table 1. Since the core gene itself is not affected, synthesis of the core protein proceeds normally enabling production of virions. Precore $A_{1896}$ mutations occur in both anti-HBe-positive patients with mild disease and those with high level viraemia and severe chronic hepatitis, suggesting that there is not a direct causal association with chronic progressive disease. However, infection with precore mutant virus has been associated with fulminant hepatitis and in the transplantation setting, graft failure (15).

The HBsAg comprises an antigenic region referred to as the "a" determinant (7). The "a" determinant is complex, conformational and dependent upon disulphide bonding among highly conserved cysteine residues. Genetic variation leading to changes in the "a" determinant has been implicated in mutants of HBV which escape the immunological response generated to conventional vaccines (8–12). One particularly common mutation is a glycine (G) to arginine (R) substitution at amino acid position 145 (G145R) of HBsAg. This mutation affects the "a" epitope region.

The increasing reliance on chemical and immunological intervention in treating or preventing HBV infection is resulting in greater selective pressure for the emergence of variants of HBV which are resistant to the interventionist therapy. Due to the overlapping genomic structure of HBV, HBV variants, may be directly or indirectly selected for by the use of chemical agents or vaccines.

It is important to be able to detect variant HBVs so that appropriate steps can be taken to modify a therapeutic protocol. This is also particularly important in the development of new therapeutic agents to be effective against known resistant variants of HBV and also when cross resistance develops within a family of chemically related anti-viral agents.

HBV baculovirus mediated HBV replication is a transient system and does not require integration of the HBV viral genome. This system was recently described by Delaney et al. (13, 14). The HBV baculovirus system has a number of advantages over standard transient transfection systems and cell lines expressing HBV.

In the study of HBV replication and the development of therapeutic agents directed against HBV, some cell lines have been developed which arc capable of expressing HBV DNA. However, these cell lines were developed using HBV DNA sequences under the control of heterologous promoters or heterologous regulatory sequences which are unlikely to mimic the situation in a naturally infected cell.

Furthermore, cell lines commonly used to study HBV contain multiple copies of integrated HBV DNA. Hepadnavirus genomes are maintained in the nucleus of infected cells in vivo as a pool of episomal, covalently closed circular (CCC) DNA molecules. Although the integration of HBV DNA in human liver has been reported, it is not an obligatory part of the HBV lifecycle and integration is not required for HBV replication. In addition, when integrated HBV DNA is found, it is frequently rearranged and is often transcriptionally silent. Because HBV expressing cell lines contain stably integrated HBV DNA, viral gene expression and replication is continuous; therefore, it is not possible to experimentally control the time or conditions under which these processes are initiated. Stable HBV expressing cell lines contain fixed numbers of integrated typically head-to tail orientated HBV genomes and, as such, HBV gene expression and replication levels cannot be regulated and are restricted to the number of integrated copies which each cell line contains. Consequently, it is not possible to study the effects of increasing or decreasing the copy number of integrated HBV genomes without transfecting the cell line and/or selecting new cell lines.

HBV baculovirus infection, even at high multiplicities, is not toxic to cells such as HepG2 or Huh-7. HBV expression can be enhanced or prolonged in a population of HBV baculovirus infected cells simply by superinfection of the cultures.

One major difference between baculovirus-mediated gene transfer of HBV to HepG2 cells and stably transfected cell lines is the ability to synchronously initiate the replication process. In a stably transfected HBV cell line, such as a derivative of the HepG2 cell line referred to as "2.2.15", each cell contains virus at all phases of the replication cycle. In contrast, HBV baculovirus infection can be used to synchronously start HBV replication in, for example, HepG2 cells because these cells contain no viral products before infection. In HBV baculovirus infected HepG2 cells, it is possible to follow the time course for secretion of both HBsAg and HBeAg with time after infection using the appropriate recombinant HBV baculovirus.

There is a need, therefore, to develop a baculovirus system to screen for specific HBV variants having altered sensitivities to particular agents.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier, i.e. <400>1, <400>2, etc. A sequence listing is provided after the claims.

The present invention relates generally to an assay for detecting a variant HBV which exhibits altered sensitivity to agents. In particular, the assay comprises the use of a baculovirus system to screen for sensitivities of HBV variants to particular agents. The agents contemplated herein include chemical agents such as nucleotide and nucleoside analogues and non-nucleoside analogues, immunological agents such as antibodies and cytokines as well as other therapeutic molecules. These agents generally but not exclusively have a known effect against a reference HBV such as inhibiting or reducing HBV infection, replication and/or assembly or release of virus or virus-like particles. The assay generally comprises detecting a variant HBV which exhibits an altered sensitivity to an agent by first generating a genetic construct comprising a replication competent amount of the genome from the HBV variant contained in or fused to an amount of baculovirus genome capable of infecting cells. Before, during or after the cells are infected, an agent to be tested is brought into contact with the cells. There is an optional further step where the cells are again infected with the same construct or a genetic construct comprising the genome of an HBV wild-type or other HBV variant. The cells are then cultured for a time and under conditions sufficient for the variant HBV to replicate, express genetic sequences and/or assembly and/or release virus or virus-like particles if resistant to the agent. The cells, cell lysates or culture supernatant fluid are then subjected to viral- or viral-component-detection means to determine whether or not the HBV variant has replicated, expressed genetic material and/or assembly and/or has been released in the presence of an agent. The presence or absence of the detectable components provides an indication of resistance or sensitivity to the agent.

BRIEF DESCRIPTION OF THE FIGURES

FIG. 2 is a representation of the amino acid consensus sequence (SEQ ID NO:8) from HBV DNA polymerase proteins encompassing regions which are conserved in the RNA polymerase protein. These regions are shown as domains A–E and are underlined. In the consensus sequence the M in the YMDD motif is designated as amino acid number 550. The amino acids which are subject to mutation during 3TC and/or FCV treatment are shown in bold. An asterisk (*) indicates greater than three amino acid possibilities at this position of the consensus sequence. The HBsAg major hydrophilic region containing the neutralisation domain is indicated by a double line and the polymerase mutations which alter the HBsAg are indicated in italics.

Figure 3A:
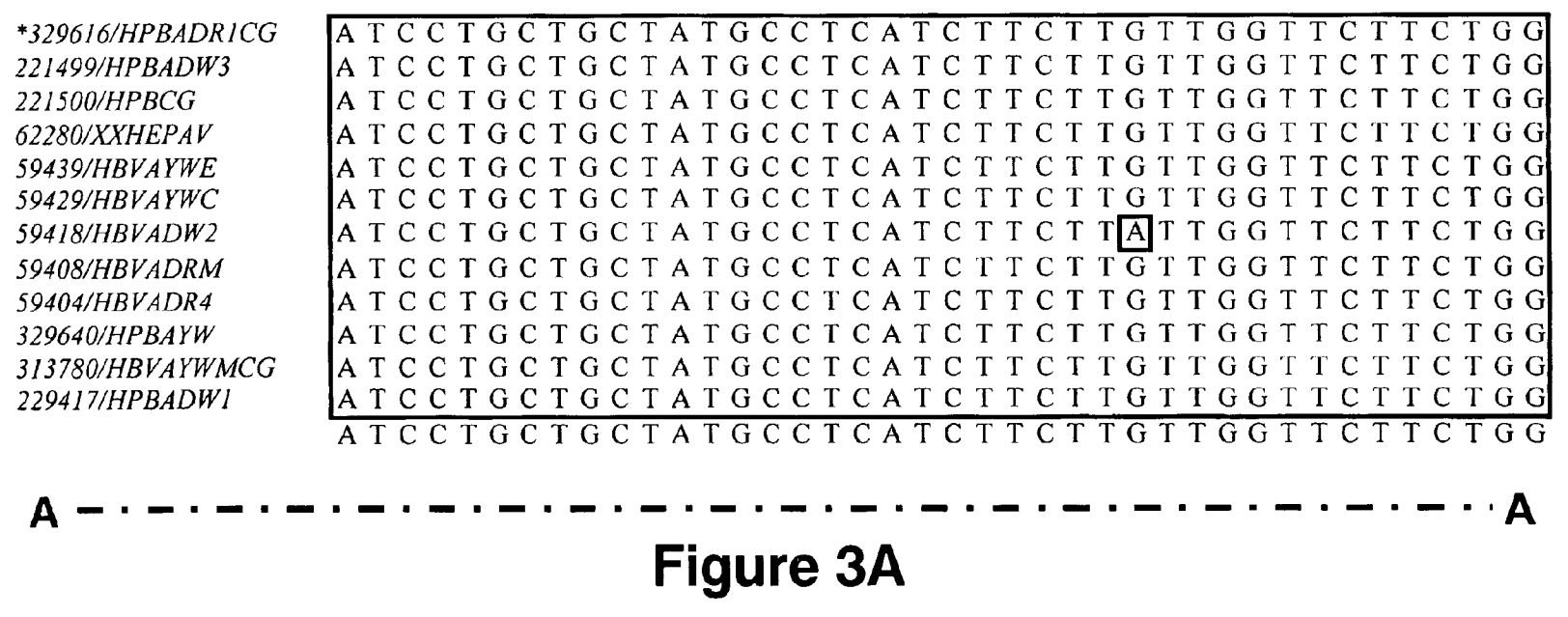
Figure 3C:
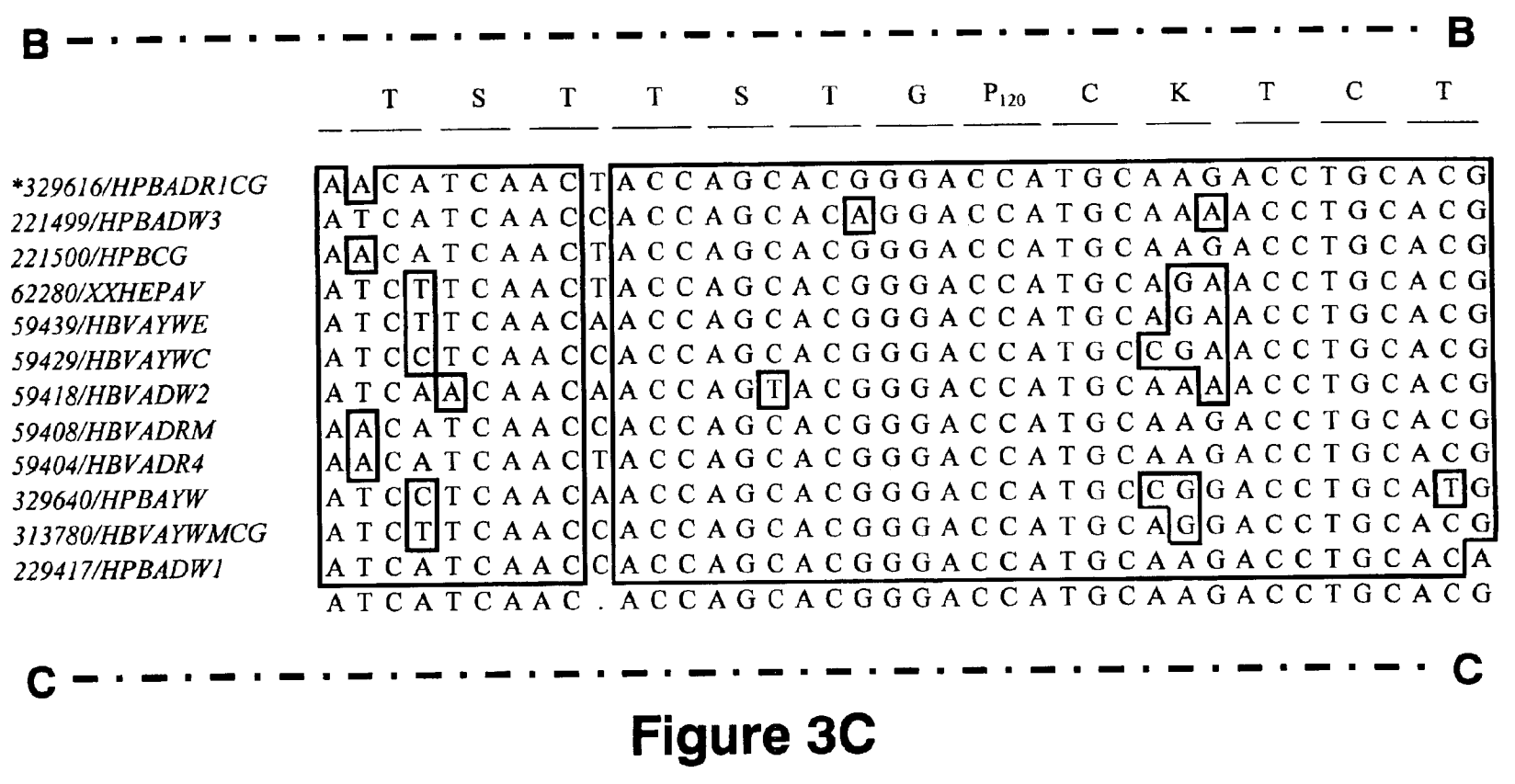
Figure 3D:
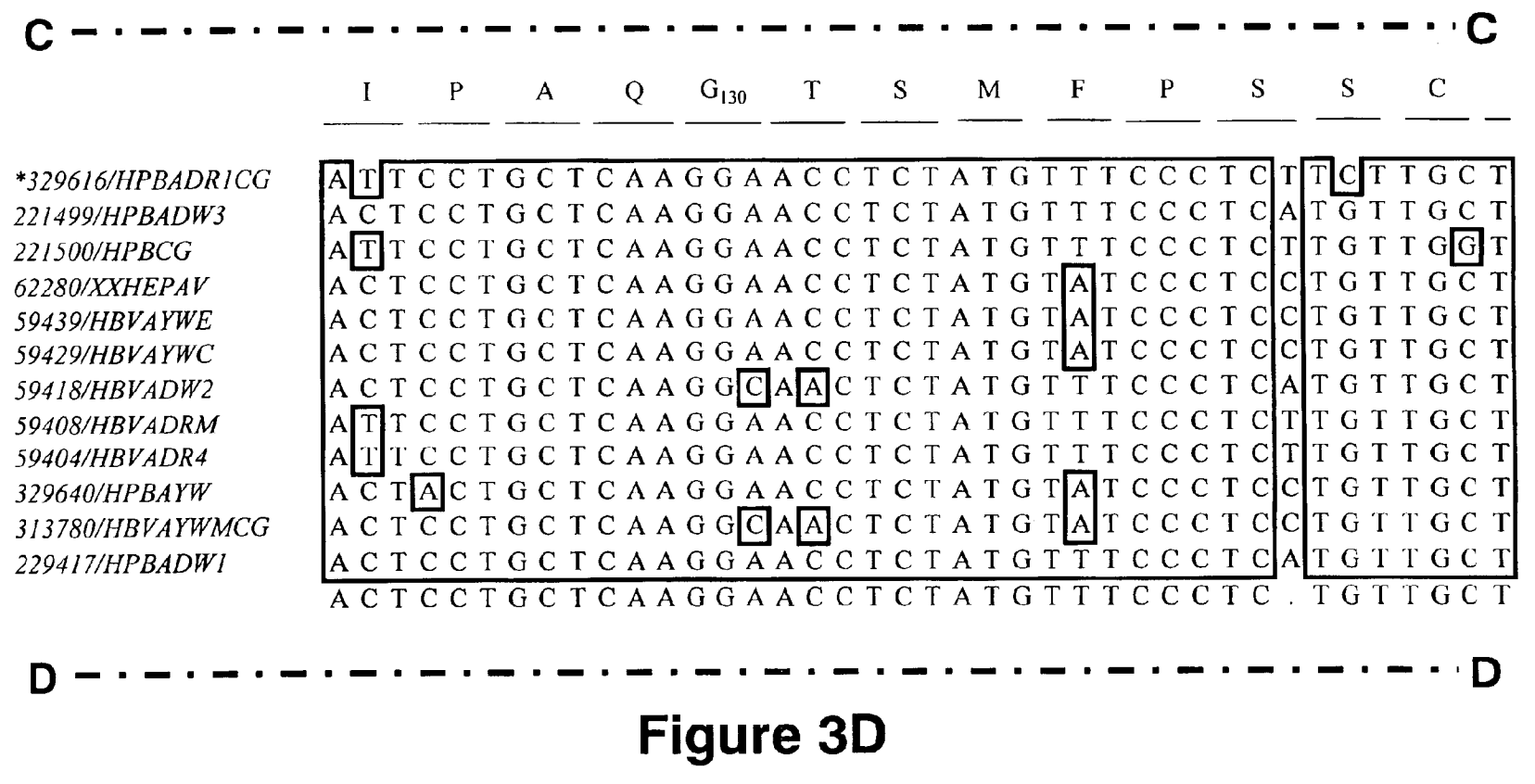
Figure 3E:
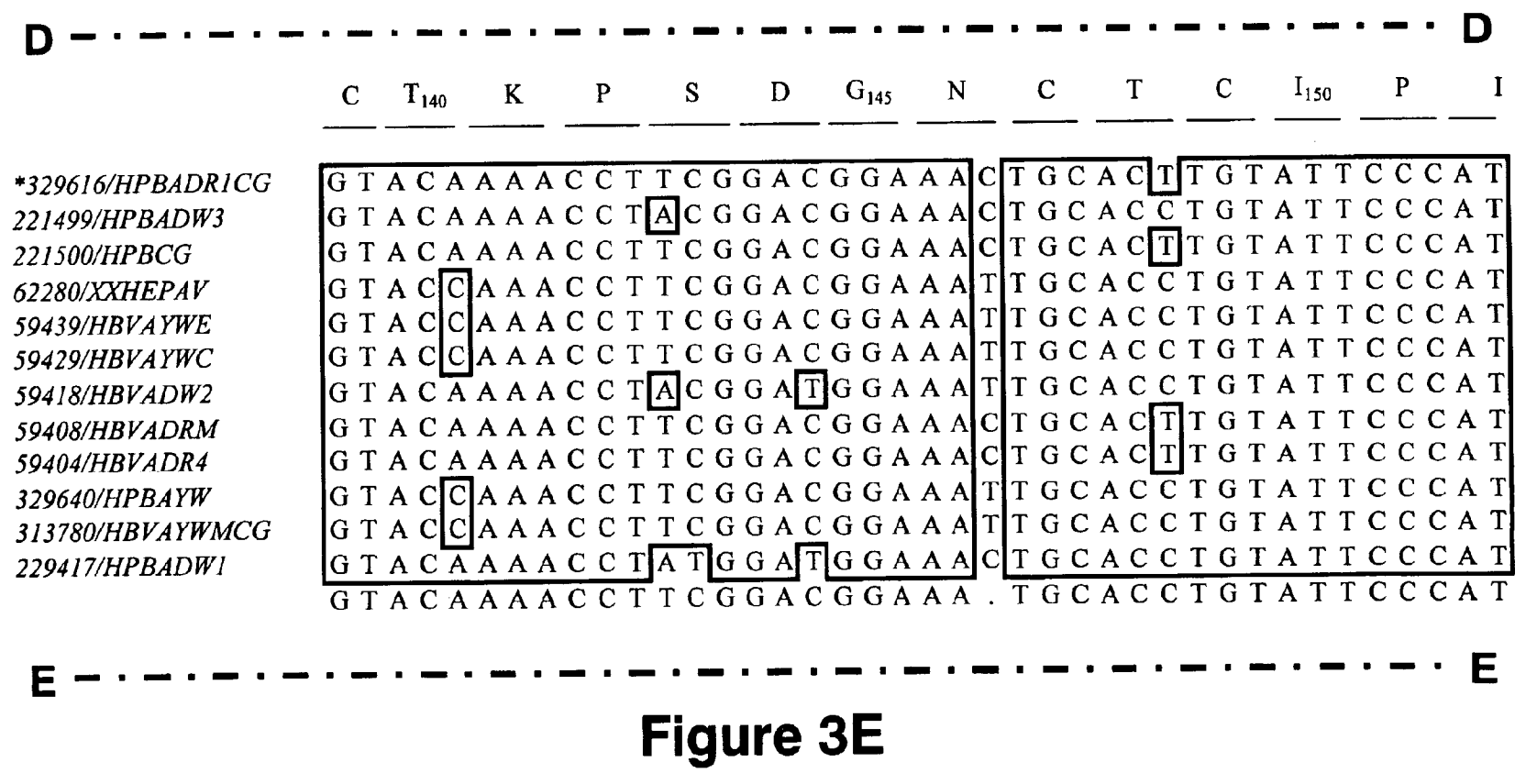
Figure 3F:
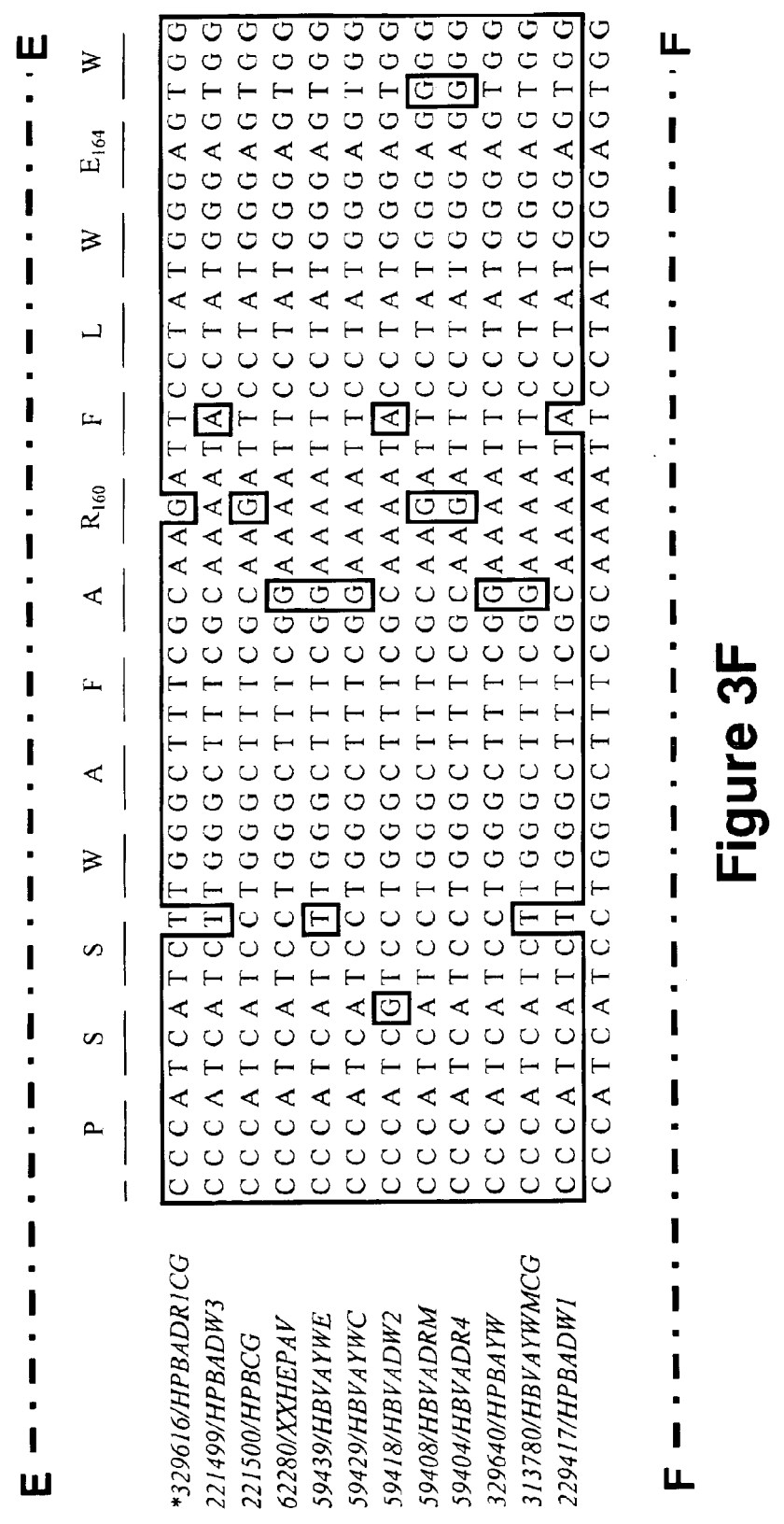
Figure 3G:
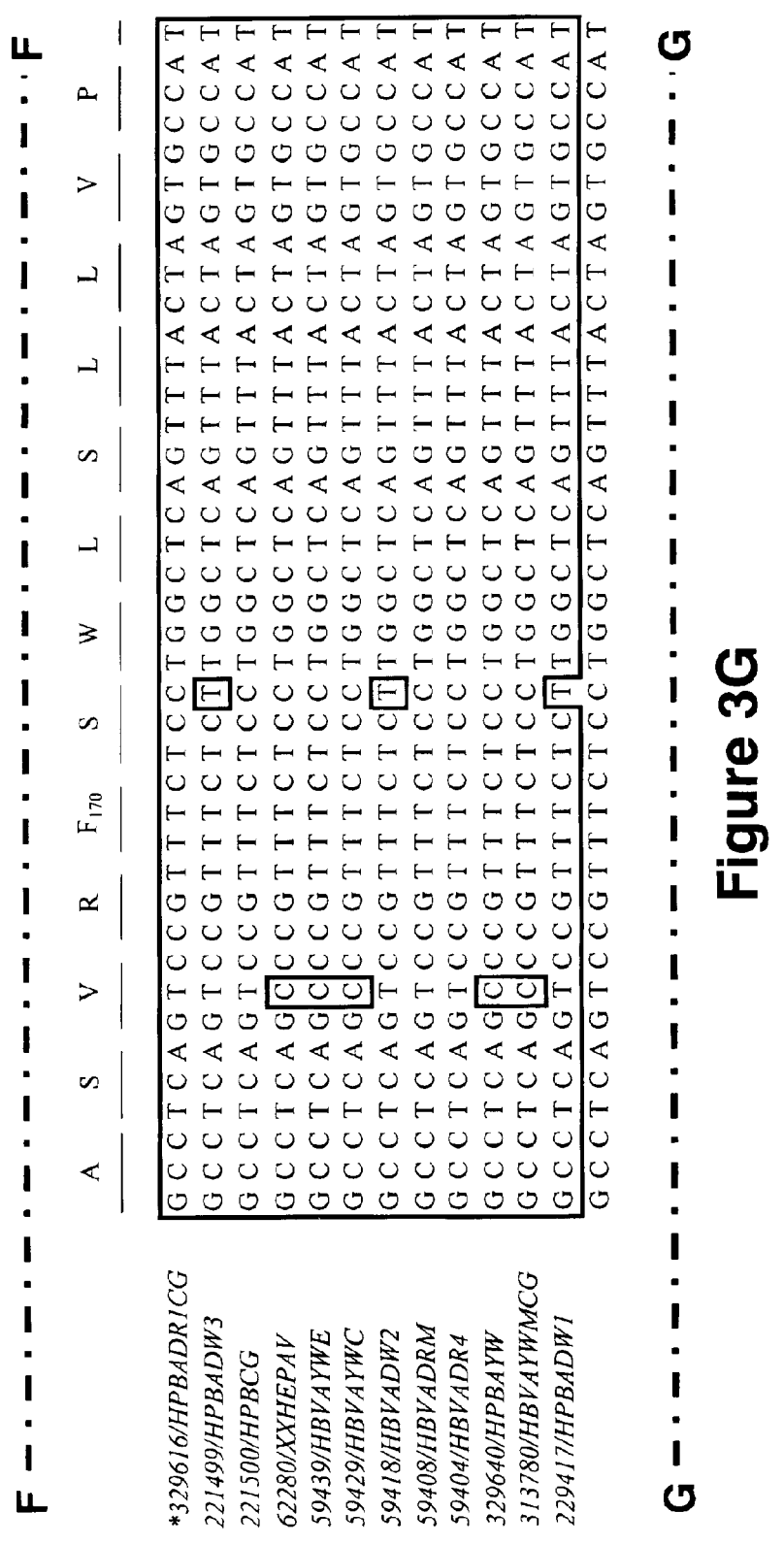
Figure 3H:
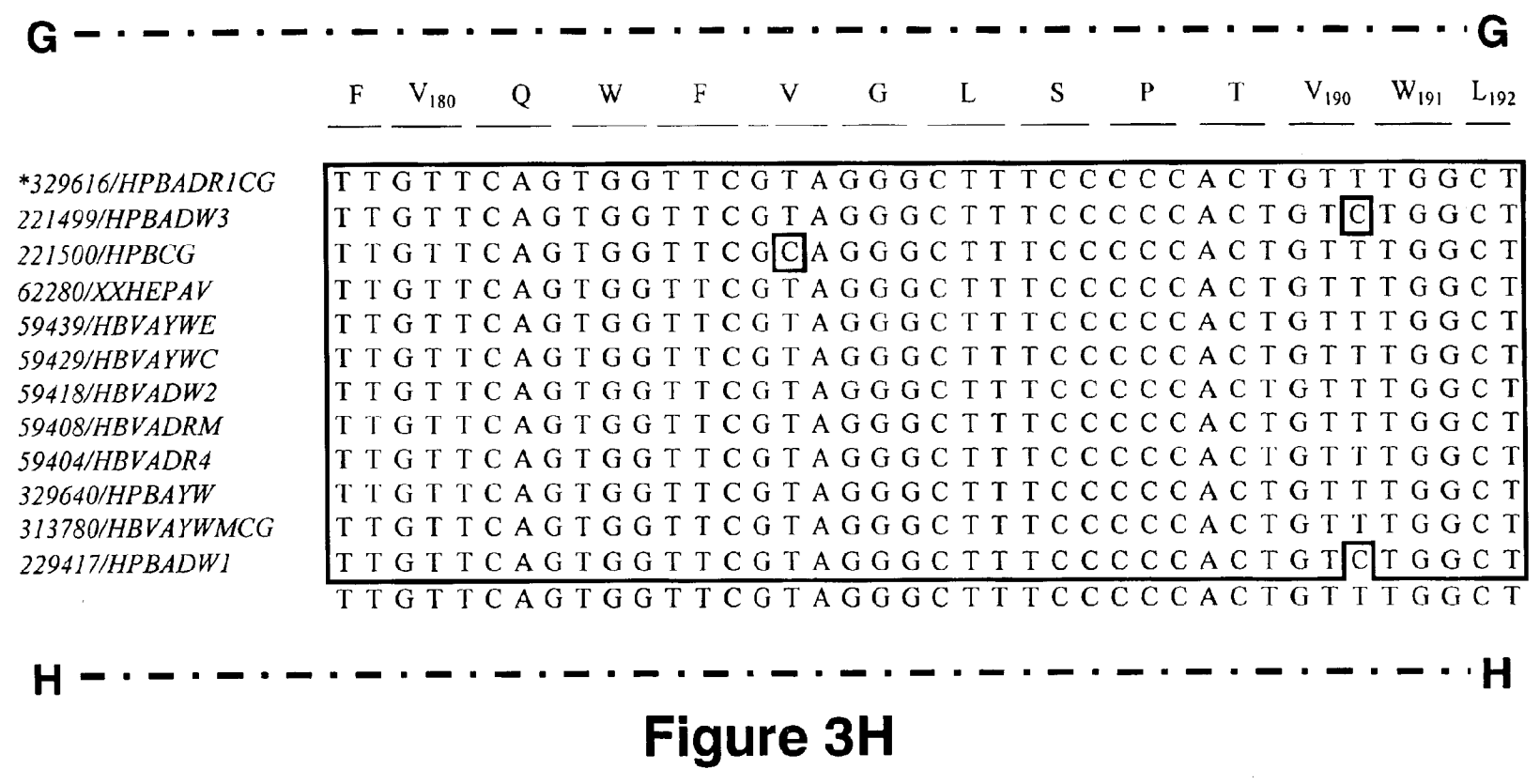

FIG. 3A–3K are representations of the nucleotide sequence from various strains of HBV encoding the surface antigen. The amino acid sequence of the surface antigen beginning at amino acid 108 is shown above the nucleotide sequence. Nucleotide sequences 329616/HPBADR1CG, 221499/HPBADW3, 221500/HPBCG, 62280/XXHEPAV, 59439/HBVAYWE, 59429/HBVAYWC, 59418/HBVADW2, 59408/HBVADRM, 59404/HBVADR4, 329640/HPBAYW, 313780/HBVAYWMCG, 229417/HPBADW1 are set forth in SEQ ID NO: 9–20, respectively.

FIG. 5A–5F are the representation of the nucleotide sequence (SEQ ID NO: 21) of HBV 1.28 genome.

FIGS. 13A to 13L are photographic representations showing Southern blot of intracellular and extracellular HBV DNA production from HepG2 cells transduced with recombinant HBV-baculovirus [M550I and precore/M550I (FIGS. 13A, 13B, 13E, 13F, 13I, 13J] L526M/M550V and precore/L526M/M550V (FIGS. 13C, 13D, 13G, 13H, 13K, 13L] exposed to various concentrations of adefovir, or lamivudine, or penciclovir. The extracellular virus production from cells transduced with L526M/M550V was too low to be measured. IC, intracellular; EC, extracelluar; RC, relaxed circular HBV DNA; DS, linear double-standard HBV DNA; SS, single-stranded HBV DNA.

FIGS. 14A–14F are the representation of the nucleotide sequence (SEQ ID NO: 22) of HBV 1.5 genome.

Figure 1A:
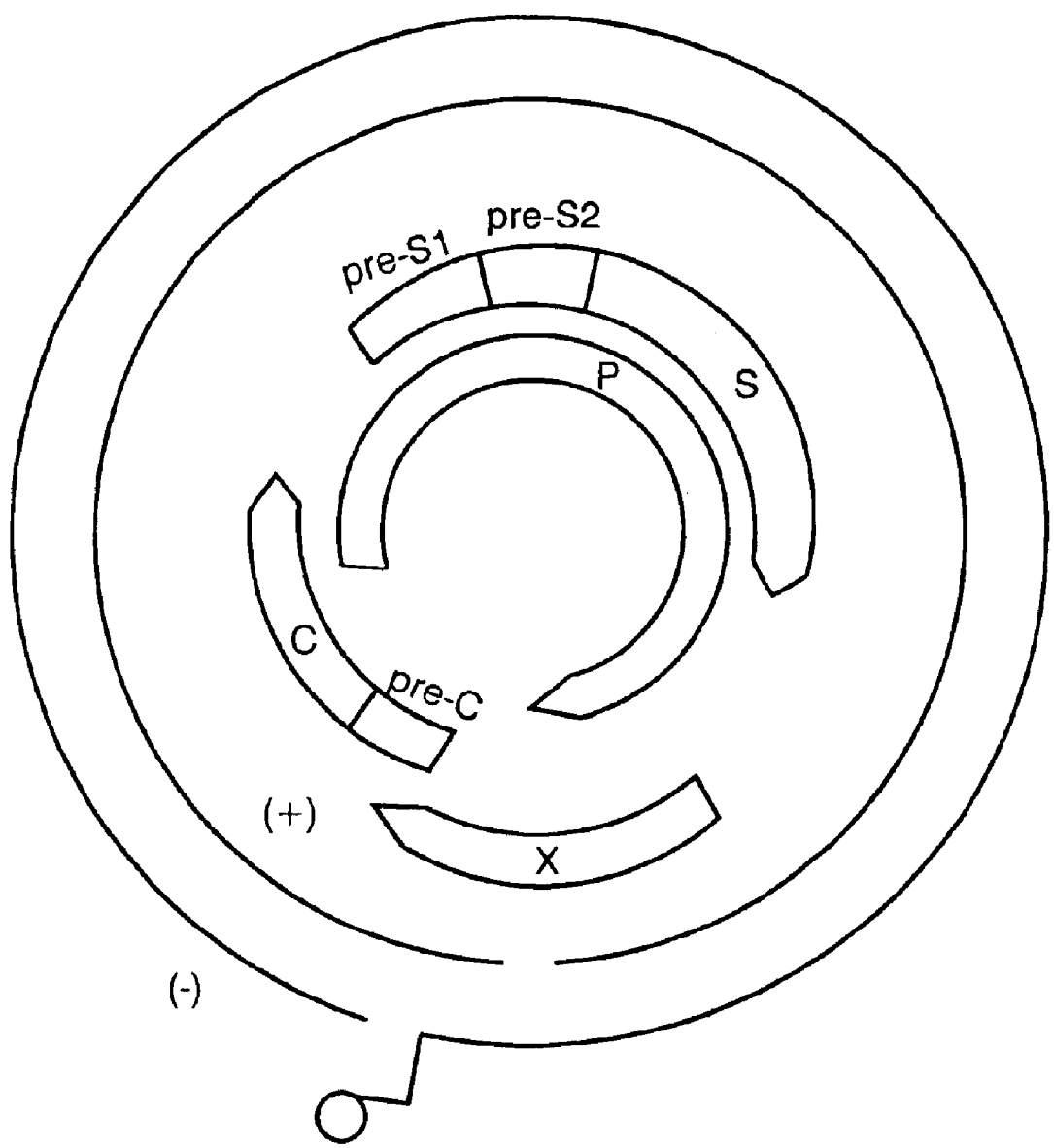
FIG. 1A is a diagrammatic representation showing overlapping genome of HBV.

The following abbreviations are used in the subject specification:

| Abbreviations | Definitions |
|---|---|
| 3TC, LAM | (−)-b-L-2',3'-dideoxy-3'-thiacytidine |
| PMEA | 9-(2-phosphonylmethoxyethyl)adenine |
| PCV | 9-[4-hydroxy-3-(hydroxymethyl)but-1-yl]guanine |
| YMDD | Amino acid motif from HBV DNA polymerase; Try Met Asp Asp; the Met is residue 550 |
| HBV | Hepatitis B virus |
| Xaa | Any amino acid |
| Pre-S1, Pre-S2, S | Viral envelope genes; S encodes HBsAg |
| HBsAg | HBV surface antigen |
| CCC DNA | Covalently closed circular DNA |
| moi | Multiplicity of infection |
| pfu | plaque forming units |
| DNA | Deoxyribonucleic acid |
| HBeAg | hepatitis B e antigen |
| RNA | Ribonucleic acid |
| PCR | Polymerase Chain Reaction |
| ELISA | Enzyme Linked Immunosorbent Assay |
| p.i. | Post infected |
| P | Polymerase gene |
| IC | intracellular |
| EC | extracellular |
| RC | Relaxed circular HBV DNA |
| DS | Linear double stranded HBV DNA |
| SS | Single-stranded HBV DNA |
| LDH | lactate dehydrogenase |
| FCV | Famciclovir |

DETAILED DESCRIPTION OF THE PREFERRED EMBODIMENTS

The present invention provides an assay using variant HBV baculovirus to screen for the sensitivities of HBV variants to particular agents. These agents generally but not exclusively have a known effect against a reference HBV such as inhibiting or reducing HBV infection, replication and/or assembly and/or release of virus or virus-like particles. The present invention provides an assay to screen for the sensitivities of HBV variants to particular agents. These agents generally but not exclusively have a known effect against a reference HBV such as inhibiting or reducing HBV infection, replication and/or assembly and/or release of virus or virus-like particles.

The present invention is predicated in part on the identification of HBV variants which have altered sensitivity to agents which would, under standard conditions, have a particular effect or absence of effect on a reference HBV.

Generally, although not exclusively, the agent inhibits or reduces HBV infection, replication and/or assembly and/or release of virus or virus-like particles. The assay determines whether the agent has the same effect on a particular variant HBV. The assay is also useful in determining the extent of cross resistance within a group of chemically or functionally related anti-viral agents. In one embodiment, the variant HBV is an escape mutant. The present invention extends, however, to the case where an agent has little effect on a reference HBV but is effective against the variant HBV. For the present purposes, a "reference" HBV is conveniently regarded as a "wild-type" HBV.

The term "variant" is used in its broadest context and includes mutants, derivatives, modified and altered forms of an HBV relative to a reference HBV. A variant generally contains a single or multiple nucleotide substitution, addition and/or deletion or truncation mutation in the viral genome and a corresponding single or multiple amino acid substitution, addition and/or deletion or truncation in a viral peptide, polypeptide or protein.

Accordingly, one aspect of the present invention contemplates a method for detecting a variant HBV which exhibits an altered sensitivity to an agent, said method comprising:

generating a genetic construct comprising a replication competent amount of the genome from said variant HBV contained in or fused to an amount of a baculovirus genome capable to infect cells, and then infecting said cells with said construct;

contacting said cells, before, during and/or after infection, with the agent to be tested;

optionally further infecting said cells with the same genetic construct or a genetic construct comprising the genome of HBV wild-type or another HBV variant;

culturing said cells for a time and under conditions sufficient for the variant HBV to replicate, express genetic sequences and/or assemble and/or release virus or virus-like particles if resistant to said agent; and subjecting the cells, cell lysates or culture supernatant fluid to viral- or viral-component-detection means to determine whether or not the variant virus has replicated, expressed genetic material and/or assembled and/or been released in the presence of said agent.

Preferably, the altered sensitivity includes an effect on viral infection, replication and/or assembly and/or release of virus or virus-like particles or an effect on intermediary steps during the processes of infection, replication, assembly and/or release. In a particularly preferred embodiment the identification of whether the HBV variant is resistant to an agent is determined. Resistance to an agent includes resistance to two or more chemically or functionally related agents as may occur during the development of cross resistance.

Accordingly, another aspect of the present invention provides a method for detecting a variant HBV which is capable of infecting, replicating, assembly and/or release in the presence of an agent which inhibits or reduces infection, replication, assembly and/or release of a reference HBV said method comprising:

generating a genetic construct comprising a replication competent amount of said variant HBV genome contained in or fused to an amount of a baculovirus genome capable to infect cells and then infecting cells with said construct;

contacting said cells, before and/or during and/or after infection, with the agent to be tested;

optionally further infecting said cells with the same genetic construct or a genetic construct comprising the genome of HBV wild-type or another HBV variant;

culturing said cells for a time and under conditions sufficient for the variant HBV to replicate, express genetic material and/or assemble and/or release virus or virus-like particles if resistant to said agent; and subjecting the cells or cell lysates to viral- or viral component-detection means to determine whether or not the variant virus has replicated, expressed genetic material or assembled and/or been released in the presence of said agent.

The optional step referred to above encompasses testing of the effects of co-infection by the same or other HBVs.

Accordingly, another aspect of the present invention provides a method for detecting a variant HBV which is capable of infecting, replicating, assembly and/or release in the presence of an agent which inhibits or reduces infection, replication, assembly and/or release of a reference HBV said method comprising:

generating a genetic construct comprising a replication competent amount of said variant HBV genome contained in or fused to an amount of a baculovirus genome capable to infect cells and then infecting cells with said construct;

contacting said cells, before and/or during, and/or after infection, with the agent to be tested;

optionally further infecting said cells with the same genetic construct or a genetic construct comprising the genome of HBV wild-type or another HBV variant at one or more times after the initial infection;

culturing said cells for a time and under conditions sufficient for the variant HBV to replicate, express genetic material and/or assemble and/or release virus or virus-like particles if resistant to said agent; and subjecting the cells or cell lysates to viral- or viral component-detection means to determine whether or not the variant virus has replicated, expressed genetic material or assembled and/or been released in the presence of said agent.

The optional step referred to above encompasses testing of the effects of superinfection by the same or other HBVs.

The detection of HBV or its components in cells, cell lysates and culture supernatant fluid may be by any convenient means. For example, total HBV DNA or RNA may be determined, replicative intermediates may be detected or HBV-specific products or gene transcripts may be determined. Suitable assay means includes PCR, nucleic acid hybridization protocols such as northern blots and Southern blots and antibody procedures such as ELISA and Western blot may be employed.

An example of an HBV variant of the present invention is a variant obtained following selective pressure in the clinical setting. One form of selective pressure is chemical pressure (e.g. via nucleoside analogues) directed to the HBV DNA polymerase which selects for a mutation in the gene encoding HBV DNA polymerase. Due to the overlapping nature of the HBV genome, a corresponding mutation may also occur in the gene encoding HBsAg (see FIG. 1B). Accordingly, a mutation in one or more nucleotides encoding HBV DNA polymerase may have an effect on the nucleotide sequence encoding HBsAg.

A viral variant may in accordance with the present invention, carry a mutation only in the DNA polymerase or the surface antigen or may carry a mutation in both genes. The term "mutation" is to be read in its broadest context and includes a silent mutation not substantially affecting the normal function of the DNA polymerase or surface antigen or may be an active mutation having the effect of selection of nucleoside analogue resistance or a vaccine escape mutant phenotype. Where multiple mutations occur in accordance with the present invention or where multiple phenotypes result from a single mutation, at least one mutation must be active or the virus must exhibit at least one altered phenotype such as nucleoside analogue resistance or reduced immunological interactivity of anti-HBs to the surface antigen of a reference HBV.

The present invention extends to assaying any HBV mutant carrying a single or multiple substitution, addition and/or deletion or truncation in the amino acid sequence of the catalytic region of the HBV DNA polymerase as compared to the amino acid sequence set forth in Formula I (SEQ ID NO: 5) which is considered herein to define a reference HBV:

FORMULA I

S $Z_1$ L S W L S L D V S A A F Y H $Z_2$ P L H P A A M P H L L $Z_3$ G S S G L $Z_4$ R Y V A R L S S $Z_5$ S $Z_6$ $Z_7$ X N $Z_8$ Q $Z_9$ $Z_{10}$ X X X $Z_{11}$ L H $Z_{12}$ $Z_{13}$ C S R $Z_{14}$ L Y V S L $Z_{15}$ L L Y $Z_{16}$ T $Z_{17}$ G $Z_{18}$ K L H L $Z_{19}$ $Z_{20}$ H P I $Z_{21}$ L G F R K $Z_{22}$ P M G $Z_{23}$ G L S P F L L A Q F T S A I $Z_{24}$ $Z_{25}$ $Z_{26}$ $Z_{27}$ $Z_{28}$ R A F $Z_{29}$ H C $Z_{30}$ $Z_{31}$ F $Z_{32}$ Y M* D D $Z_{33}$ V L G A $Z_{34}$ $Z_{35}$ $Z_{36}$ $Z_{37}$ H $Z_{38}$ E $Z_{39}$ L $Z_{40}$ $Z_{41}$ $Z_{42}$ $Z_{43}$ $Z_{44}$ $Z_{45}$ $Z_{46}$ L L $Z_{47}$ $Z_{48}$ G I H L N P $Z_{49}$ K T K R W G Y S L N F M G Y $Z_{50}$ I G wherein:
X is any amino acid;
$Z_1$ is N or D;
$Z_2$ is I or P;
$Z_3$ is I or V;
$Z_4$ is S or D;
$Z_5$ is T or N;
$Z_6$ is R or N;
$Z_7$ is N or I;
$Z_8$ is N or Y or H;
$Z_9$ is H or Y;
$Z_{10}$ is G or R;
$Z_{11}$ is D or N;
$Z_{12}$ is D or N;
$Z_{13}$ is S or Y;
$Z_{14}$ is N or Q;
$Z_{15}$ is L or M;
$Z_{16}$ is K or Q;
$Z_{17}$ is Y or F;
$Z_{18}$ is R or W;
$Z_{19}$ is Y or L;
$Z_{20}$ is S or A;
$Z_{21}$ is I or V;
$Z_{22}$ is I or L;
$Z_{23}$ is V or G;
$Z_{24}$ is C or L;
$Z_{25}$ is A or S;
$Z_{26}$ is V or M;
$Z_{27}$ is V or T;
$Z_{28}$ is R or C;
$Z_{29}$ is F or P;
$Z_{30}$ is L or V;
$Z_{31}$ is A or V;
$Z_{32}$ is S or A;
$Z_{33}$ is V or L or M;
$Z_{34}$ is K or R;
$Z_{35}$ is S or T;
$Z_{36}$ is V or G;
$Z_{37}$ is Q or E;
$Z_{38}$ is L or S or R;
$Z_{39}$ is S or F;
$Z_{40}$ is F or Y;
$Z_{41}$ is T or A;
$Z_{42}$ is A or S;
$Z_{43}$ is V or I;
$Z_{44}$ is T or C;
$Z_{45}$ is N or S;
$Z_{46}$ is F or V;
$Z_{47}$ is S or D;
$Z_{48}$ is L or V;
$Z_{49}$ is N or Q;
$Z_{50}$ is V or I; and
M* is amino acid 550.

Accordingly, another aspect of the present invention provides an assay for detecting an HBV variant having an altered sensitivity to an agent, said variant HBV comprising a single or multiple amino acid substitution, addition and/or deletion or truncation compared to the amino acid sequence set forth in Formula I and wherein the variant HBV is selected for by a nucleoside analogue of the HBV DNA polymerase said method comprising:

generating a genetic construct comprising a replication competent amount of the genome from said variant HBV contained in or fused to an amount of a baculovirus genome capable to infect cells and infecting said cells with said construct;

contacting said cells, before and/or during, and/or after infection, with the agent to be tested;

optionally further infecting said cells with the same genetic construct or a genetic construct comprising the genome of HBV wild-type or another HBV variant;

culturing said cells for a time and under conditions sufficient for the variant HBV to replicate, express genetic sequences and/or assemble and/or release virus or virus-like particles if resistant to said agent; and subjecting the cells, cell lysates or culture supernatant fluid to viral- or viral-component-detection means to determine whether or not the variant virus has replicated, expressed genetic material or assembled and/or been released in the presence of said agent.

In a related embodiment the present invention is directed to an assay for an HBV variant, in which the HBV variant exhibits reduced sensitivity to an agent which otherwise inhibits or reduces infection, replication or assembly and/or release by a reference HBV, said variant HBV comprising a single or multiple amino acid substitution, addition and/or deletion or truncation compared to the amino acid sequence set forth in Formula I, said method comprising:

generating a genetic construct comprising a replication competent amount of said variant HBV genome contained in or fused to an amount of a baculovirus genome capable to infect cells and then infecting cells with the construct;

contacting said cells, before, and/or during, and/or after infection, with the agent to be tested;

optionally further infecting said cells with the same genetic construct or a genetic construct comprising the genome of HBV wild-type or another HBV variant;

culturing said cells for a time and under conditions sufficient for the variant HBV, express genetic material and/or assemble and/or release virus or virus-like particles if resistant to said agent; and subjecting the cells or cell lysates to viral- or viral component-detection means to determine whether or not the variant virus has replicated, expressed genetic material or assembled and/or been released in the presence of said agent.

Another HBV variant contemplated by the present invention is in the precore or the basal core promoter sequences. Precore mutations contemplated by the present invention include those listed in Table 1 and include. Particular precore gene and basal core promoter (BCP) mutations include A1814T, C1856T, G1896A, G1897A, G1898A, G1899A, G1896A/G1899A, A1762T/ G1764A, T1753C, G1757A and C1653T (where the numbering is from the unique EcoR1 site in HBV).

Accordingly, another aspect of the present invention provides an assay for an HBV variant with an altered sensitivity to an agent, said variant HBV comprising a nucleotide sequence containing a single or multiple nucleotide substitution, addition and/or deletion to the precore nucleotide sequence, said method comprising:

generating a genetic construct comprising a replication competent amount of the genome from said variant HBV contained in or fused to an amount of a baculovirus genome capable to infect cells and infecting said cells with said construct;

contacting said cells, before and/or during, and/or after infection, with the agent to be tested;

optionally further infecting said cells with the same genetic construct or a genetic construct comprising the genome of HBV wild-type or another HBV variant;

culturing said cells for a time and under conditions sufficient for the variant HBV to replicate, express genetic sequences or assemble if resistant to said agent, and subjecting the cells, cell lysates or culture supernatant fluid to viral- or viral-component-detection means to determine whether or not the variant virus has replicated, expressed genetic material or assembled in the presence of said agent Preferably, the HBV variant according to this aspect of the present invention has a precore gene or a BCP mutation as listed in Table 1. In a particularly preferred embodiment, the precore or a BCP mutation is selected from A1814T, C1856T, G1896A, G1897A, G1898A, G1899A, G1896A/G1899A, A1762T/G1764A, T1753C, G1757A and C1653T (where the numbering is from the unique EcoR1 site in HBV).

In a related embodiment, the present invention contemplates an assay for an HBV variant which exhibits reduced sensitivity to an agent which otherwise inhibits or reduces infection, replication or assembly and/or release by a reference HBV, said variant HBV comprising a nucleotide sequence comprising a single or multiple nucleotide substitution, addition and/or deletion to the precore nucleotide sequence, said method comprising:

generating a genetic construct comprising a replication competent amount of the genome from said variant HBV contained in or fused to an amount of a baculovirus genome capable to infect cells and infecting said cells with said construct;

contacting said cells, before, and/or during, and/or after infection, with the agent to be tested;

optionally further infecting said cells with the same genetic construct or a genetic construct comprising the genome of HBV wild-type or another HBV variant;

culturing said cells for a time and under conditions sufficient for the variant HBV to replicate, express genetic sequences or assemble if resistant to said agent; and subjecting the cells, cell lysates or culture supernatant fluid to viral- or viral-component-detection means to determine whether or not the variant virus has replicated, expressed genetic material or assembled in the presence of said agent.

In another embodiment, the HBV variant comprises a precore mutation together with a mutation in the DNA polymerase or the corresponding mutation in the hepatitis B surface antigen (HBsAg). Preferred mutations according to this embodiment result from resistance to lamivudine (LAM) such as but are limited to a precore mutation together with L526M+M550V [M195I] or a precore mutation together with M550I [W196L, W196S or W196STOP]. The mutations given in parenthesis are the corresponding HBsAg mutations following a mutation in the HBV DNA polymerase gene, Preferred precore gene and BCP mutations are A1814T, C1856T, G1896A, G1897A, G1898A, G1899A, G1896A/G1899A, A1762T/G1764A, T1753C, G1757A, G1653T (Table 1).

Accordingly, another aspect of the present invention provides an assay for an HBV variant with an altered sensitivity to LAM or another agent, said variant HBV comprising a nucleotide sequence comprising a single or multiple nucleotide substitution, addition and/or deletion to the precore nucleotide sequence, and the DNA polymerase gene and optionally the overlapping HBsAg nucleotide sequence said method comprising:

generating a genetic construct comprising a replication competent amount of the genome from said variant HBV contained in or fused to an amount of a baculovirus genome capable to infect cells and infecting said cells with said construct;

contacting said cells, before and/or during, and/or after infection, with the agent to be tested;

optionally further infecting said cells with the same genetic construct or a genetic construct comprising the genome of HBV wild-type or another HBV variant;

culturing said cells for a time and under conditions sufficient for the variant HBV to replicate, express genetic sequences or assemble if resistant to said agent; and subjecting the cells, cell lysates or culture supernatant fluid to viral- or viral-component-detection means to determine whether or not the variant virus has replicated, expressed genetic material or assembled in the presence of said agent.

In a related embodiment, the present invention contemplates an assay for an HBV variant which exhibits reduced sensitivity to LAM or another agent and which otherwise inhibits or reduces infection, replication or assembly and/or release by a reference HBV, said variant HBV comprising a nucleotide sequence encoding a single or multiple nucleotide substitution, addition and/or deletion to the precore nucleotide sequence, and in the DNA polymerase gene and optionally the HBsAg nucleotide sequence said method comprising:

generating a genetic construct comprising a replication competent amount of the genome from said variant HBV contained in or fused to an amount of a baculovirus genome capable to infect cells and infecting said cells with said construct;

contacting said cells, before, and/or during, and/or after infection, with the agent to be tested;

optionally further infecting said cells with the same genetic construct or a genetic construct comprising the genome of HBV wild-type or another HBV variant;

culturing said cells for a time and under conditions sufficient for the variant HBV to replicate, express genetic sequences or assemble if resistant to said agent; and subjecting the cells, cell lysates or culture supernatant fluid to viral- or viral-component-detection means to determine whether or not the variant virus has replicated, expressed genetic material or assembled in the presence of said agent.

Preferably, the HBV variants according to these aspects of the present invention has a precore gene and BCP mutation as listed in Table 1. In a particularly preferred embodiment, the precore or a BCP mutation is selected from A1814T, C1856T, G1896A, G1897A, G1898A, G1899A, G1896A/G1899A, A1762T/G1764A, T1753C, G1757A and C1653T (where the numbering is from the unique EcoR1 site in HBV). Preferably, the mutation of the DNA polymerase gene [and HBsAg] is L526M+M550V [M195I] or M550I [W196L, W196S or W196STOP].

Another example of a variant to be tested in accordance with the present invention is one with an altered immunological profile. Such a variant would substantially not be affected by a neutralizing immune response directed to a conventional HBV vaccine such as a vaccine comprising a reference HBV or a surface component thereof. Similarly, the variant HBV may substantially not be affected at the infection, replication, assembly or release level or another level during the life cycle of the HBV by an agent which is capable of inhibiting or reducing infection, replication, assembly or release of a reference HBV. The expression "substantially not affected" includes reduced susceptibility to the immune response generated by a vaccine or reduce susceptibility to chemical agents such as nucleoside analogues which target HBV genes such as the DNA polymerase. Due to the overlapping nature of reading frames for DNA polymerase and certain viral surface components, an altered surface component may have a corresponding alteration in the DNA polymerase.

A preferred surface component of the HBV of the present invention is HBsAg. It is proposed in accordance with this aspect of the present invention that the HBsAg of the HBV variants exhibit an altered immune profile relative to an HBsAg from a reference HBV. For the purposes of the present invention, a reference HBV conveniently comprises an HBsAg with an amino acid sequence substantially as set forth by Norder et al. (1) and Stuyver et al. (2) which encompasses all known genotypes of HBV (currently A through G). The assay of the present invention can be used to screen for the effect of the altered HBsAg on the sensitivity of a variant HBV to a particular agent.

The present invention extends, therefore, to any single or multiple amino acid substitution, addition and/or deletion or truncation in the amino acid sequence of HBsAg relative to the amino acid sequence set forth in Formula II below as defined by a single or multiple amino acid substitution, addition and/or deletion to the catalytic region of the HBV DNA polymerase set forth above in Formula I.

The amino acid sequence of an HBsAg and which is considered to define a reference HBV is set forth below in Formula II (SEQ ID NO: 6):

FORMULA II

M $X_1$ $X_2$ $X_3$ $X_4$ S G $X_5$ L $X_6$ P L $X_7$ V L Q A $X_8$ $X_9$ F $X_{10}$ L T $X_{11}$ I $X_{12}$ $X_{13}$ I P $X_{14}$ S L $X_{15}$ S W W T S L N F L G $X_{16}$ $X_{17}$ $X_{18}$ $X_{19}$ C $X_{20}$ G $X_{21}$ N $X_{22}$ Q S $X_{23}$ $X_{24}$ S $X_{25}$ H $X_{26}$ P $X_{27}$ $X_{28}$ C P P $X_{29}$ C $X_{30}$ G Y R W M C L $X_{31}$ R F I I F L $X_{32}$ I L L L C L I F L L V L L D $X_{33}$ Q G M L $X_{34}$ V C P L $X_{35}$ P $X_{36}$ $X_{37}$ $X_{38}$ T T S $X_{39}$ $X_{40}$ $X_{41}$ C $X_{42}$ T C $X_{43}$ $X_{44}$ $X_{45}$ $X_{46}$ Q G $X_{47}$ S $X_{48}$ $X_{49}$ P $X_{50}$ $X_{51}$ C C $X_{52}$ K P $X_{53}$ $X_{54}$ G N C T C I P I P S $X_{55}$ W A $X_{56}$ $X_{57}$ $X_{58}$ $X_{59}$ L W E $X_{60}$ $X_{61}$ S $X_{62}$ R $X_{63}$ S W L $X_{64}$LL$X_{65}$$X_{66}$ F V Q $X_{67}$ $X_{68}$ $X_{69}$ $X_{70}$ L $X_{71}$ P $X_{72}$ V W $X_{73}$ $X_{74}$ $X_{75}$ I W $X_{76}$ $X_{77}$ W $X_{78}$ W $X_{79}$ P $X_{80}$ $X_{81}$ $X_{82}$ $X_{83}$ I $X_{84}$ $X_{85}$ P F $X_{86}$ P L L P I F $X_{87}$ $X_{88}$ L $X_{89}$ $X_{90}$ $X_{91}$ I wherein:
$X_1$ is E or G or D;
$X_2$ is N or S or K;
$X_3$ is I or T;
$X_4$ is T or A;
$X_5$ is F or L;
$X_6$ is G or R;
$X_7$ is L or R;
$X_8$ is G or V;
$X_9$ is F or C;
$X_{10}$ is L or S or W;
$X_{11}$ is R or K;
$X_{12}$ is L or R;
$X_{13}$ is T or K;
$X_{14}$ is Q or K;
$X_{15}$ is D or H;
$X_{16}$ is G or E or A;
$X_{17}$ is S or A or V or T or L;
$X_{18}$ is P or T;
$X_{19}$ is V or R or T or K or G;
$X_{20}$ is L or P;
$X_{21}$ is Q or L or K;
$X_{22}$ is S or L;
$X_{23}$ is P or Q;
$X_{24}$ is T or I;
$X_{25}$ is N or S;
$X_{26}$ is S or L;
$X_{27}$ is T or I;
$X_{28}$ is S or C;
$X_{29}$ is I or T;
$X_{30}$ is P or A;
$X_{31}$ is R or Q;

$X_{32}$ is F or C;
$X_{33}$ is Y or C;
$X_{34}$ is P or H or S;
$X_{35}$ is I or L;
$X_{36}$ is G or R;
$X_{37}$ is S or T;
$X_{38}$ is T or S;
$X_{39}$ is T or V or A;
$X_{40}$ is G or E or Q;
$X_{41}$ is P or A or S;
$X_{42}$ is K or R;
$X_{43}$ is T or M;
$X_{44}$ is T or I or S or A;
$X_{45}$ is P or T or A or I or L;
$X_{46}$ is A or V;
$X_{47}$ is N or T;
$X_{48}$ is M or K or L;
$X_{49}$ is F or Y or;
$X_{50}$ is S or Y;
$X_{51}$ is C or S;
$X_{52}$ is T or I or S;
$X_{53}$ is T or S;
$X_{54}$ is D or A;
$X_{55}$ is S or T;
$X_{56}$ is F or L;
$X_{57}$ is A or G or V;
$X_{58}$ is K or R or T;
$X_{59}$ is Y or F;
$X_{60}$ is W or G;
$X_{61}$ is A or G;
$X_{62}$ is V or A;
$X_{63}$ is F or L;
$X_{64}$ is S or N;
$X_{65}$ is V or A;
$X_{66}$ is P or Q;
$X_{67}$ is W or C or S;
$X_{68}$ is F or C;
$X_{69}$ is V or D or A;
$X_{70}$ is G or E;
$X_{71}$ is S or;
$X_{72}$ is T or I;
$X_{73}$ is L or P;
$X_{74}$ is S or L;
$X_{75}$ is A or V;
$X_{76}$ is M or I;
$X_{77}$ is M or I;
$X_{78}$ is Y or F;
$X_{79}$ is G or E;
$X_{80}$ is S or N or K;
$X_{81}$ is L or Q;
$X_{82}$ is Y or F or H or C;
$X_{83}$ is S or G or N or D or T;
$X_{84}$ is V or L;
$X_{85}$ is S or N;
$X_{86}$ is I or M or L;
$X_{87}$ is F or C;
$X_{88}$ is C or Y;
$X_{89}$ is W or R;
$X_{90}$ is V or A; and
$X_{91}$ is Y or I or S.

Accordingly, another aspect of the present invention provides a method for detecting a variant HBV having an altered sensitivity to an agent, the said variant HBV comprising a surface antigen having an amino acid sequence with a single or multiple amino acid substitution, addition and/or deletion or a truncation compared to a surface antigen from a reference HBV such that an antibody generated to the reference surface antigen exhibits altered capacity for neutralizing said HBV variant said method comprising:

generating a genetic construct comprising a replication competent amount of the genome from said variant HBV contained in or fused to an amount of a baculovirus genome capable to infect cells and then infecting said cells with said construct;

contacting said cells, before, and/or during, and/or after infection, with the agent to be tested;

culturing said cells for a time and under conditions sufficient for the variant HBV to replicate, express genetic sequences or assemble if resistant to said agent; and subjecting the cells, cell lysates or culture supernatant fluid to viral- or viral-component-detection means to determine whether or not the variant virus has replicated, expressed genetic material or assembled in the presence of said agent.

The amino acid sequence of the HBsAg of the reference HBV is as set forth in Formula II above.

Generally, the method of the present invention is capable of detecting an HBV variant which may be regarded as an escape mutant which it is substantially incapable of being adversely effected by chemical therapy directed against the HBV polymerase or vaccine therapy directed against the surface antigen. The term "escape" mutant also encompasses reduced susceptibility to chemical or vaccine therapy directed to the reference HBV.

More particularly, another aspect of the present invention provides a method for detecting a variant HBV which is capable of replicating in the presence of an agent which inhibits or reduces replication of a reference HBV, said reference HBV comprising a surface antigen having an amino acid sequence with a single or multiple amino acid substitution, addition and/or deletion or a truncation compared to a surface antigen from a reference HBV such that an antibody generated to the reference surface antigen exhibits altered capacity for neutralizing said HBV variant said method comprising:

generating a genetic construct comprising a replication competent amount of said variant HBV genome contained in or fused to an amount of a baculovirus genome capable to infect cells and then infecting cells with the construct;

contacting said cells, before and/or during, and/or after infection, with the agent to be tested;

culturing said cells for a time and under conditions sufficient for the variant HBV to replicate, express genetic material or assemble if resistant to said agent; and subjecting the cells or cell lysates to viral- or viral component-detection means to determine whether or not the variant virus has replicated, expressed genetic material or assembled in the presence of said agent.

The present invention also extends to changes in the HBsAg following immunological selection based on vaccines comprising HBsAg or a derivative thereof or an HBV comprising same and wherein the HBsAg comprises an amino acid sequence substantially as set forth in Formula II.

An "agent" therefore extends to a chemical agent (e.g. nucleotide and nucleoside analogues and non-nucleoside analogues), an immunological agent (e.g. antibodies or cytokines) or other therapeutic molecule. One group of agents contemplated by the present invention are non-nucleoside analogue reverse transcriptase inhibitors (such as but not limited to AT-61 a phenylpropenamide derivative;

16) and non-nucleoside analogue DNA dependent DNA polymerase inhibitors. A group of nucleoside analogues contemplated herein comprises 3TC, PMEA and PCV and related molecules.

Reference to an altered immunological profile in accordance with the present invention in relation to the surface antigen includes reference to an altered humoral or T cell response. Examples of an altered immunological profile include altered specificity to antibodies, altered amino acid sequences of an epitope or within the "a" determinant, an altered capacity to induce proliferation of T cells primed to an HBsAg from a reference HBV. Preferably, the altered immunological profile means that neutralizing antibodies which are capable of substantially neutralising or otherwise reducing serum or blood levels of the reference HBV are substantially incapable of or exhibit reduced capacity to neutralize and/or clear the variant HBV.

The HBsAg mutations of the present invention may also be defined in terms of a corresponding mutation in the HBV DNA polymerase. A mutation in the HBV DNA polymerase may be in amino acids 421–431, 426–436, 431–441, 436–446, 441–451, 446–456, 451–461, 456–466, 461–471, 466–476, 471–481, 476–486, 481–491, 486–496, 491–501, 496–506, 501–511, 506–516, 511–521, 516–526, 521–531, 526–536, 531–541, 536–546, 541–551, 546–556, 551–561, 556–566, 561–571, 566–576, 571–581, 576–586, 581–591, 586–596, 591–601, 596–601 (referring to the amino acid numbering in FIG. 2).

Preferred HBV DNA polymerase mutations include L426I/V, L428Iv, Q476, N480G, N485K, K495R, R499Q, G499E, W499Q, F512L, I515L, V519L, L526M, M550V, M550I, V553I, S565P. Useful multiple mutants include L526M/M550I, L526M/M550V, V519L/L526M/M550V and V519L/L526M/M550I.

Preferred mutations in the amino acid sequence of HBsAg are amino acid substitutions, deletions and/or additions or truncations in amino acids 1–10, 5–15, 10–20, 15–25, 20–30, 25–35, 30–40, 35–45, 40–50, 45–55, 50–60, 55–65, 60–70, 65–75, 70–80, 75–85, 80–90, 85–95, 90–100, 95–105, 100–110, 105–115, 110–120, 115–125, 120–130, 125–135, 130–140, 135–145, 140–150, 145–155, 150–160, 155–165, 160–170, 165–175, 170–180, 175–185, 180–190, 185–195, 190–200, 195–205, 200–210, 205–215, 210–220, 215–225, 220–226 (referring to the numbering of Formula II) of HBsAg. Particularly useful mutations are G112R, T123P Y/F134S, D144E, G145R, A157D, E164D, F170L, M195I, W196L, W196S, W196STOP, M198I, W199S, S204T and S210R. The term "stop" means a stop codon.

Even more preferred mutations are D144E, G145R, A157D, E164D, M195I, W196L, W196S, W196STOP, M198I, W199S and S210R.

Particularly preferred precore gene and BCP mutations are selected from A1814T, C1856T, G1896A, G1897A, G1898A, G1899A, G1896A/G1899A, A1762T/ G1764A, T1753C, G1757A and C1653T (where the numbering is from the unique EcoR1 site in HBV).

The present invention extends to combinations of two or more of the above mutations such as but not limited to a precore mutation and a mutation in the DNA polymerase and optionally the overlapping HBsAg nucleotide sequences resulting in, for example, reduce sensitivity to LAM. Examples of the latter include but are not limited to a precore mutation such as G1896A with L526M+M550V [M195I] or M550I [W196L, W196S or W196STOP].

The altered HBsAg molecules of the HBV variants of the present invention may also be defined at the nucleotide level. The nucleotide sequence encoding the HBsAg from a reference HBV is set forth below in Formula III (SEQ ID NO: 7):

---

FORMULA III

A C $N_1$ A A A C C T $N_2$ $N_3$ G G A $N_4$ G G A A A $N_5$ T G C A C $N_6$ T G T A T T C C C

A T C C C A T C $N_7$ T C $N_8$ T G G G C T T T C G $N_9$ A A $N_{10}$ A T $N_{11}$ C C T A T G G G

A G $N_{12}$ G G G C C T C A G $N_{13}$ C C G T T T C T C $N_{14}$ T G G C T C A G T T T A C T

A G T G C C A T T T G T T C A G T G G T T C G $N_{15}$ A G G G C T T T C C C C C A C

T G T $N_{16}$ T G G C T T T C A G $N_{17}$ T A T A T G G A T G A T G T G G T $N_{18}$ T T G G

G G G C C A A G T C T G T A C A $N_{19}$ C A T C $N_{20}$ T G A G T C C C T T T $N_{21}$ T $N_{22}$

C C $N_{23}$ C T $N_{24}$ T T A C C A A T T T T C T T $N_{25}$ T G T C T $N_{26}$ T G G G $N_{27}$ A T A C

A T T

--- wherein:
$N_1$ is A or C;
$N_2$ is T or A;
$N_3$ is C or T;
$N_4$ is C or T;
$N_5$ is C or T;
$N_6$ is C or T;
$N_7$ is A or G;
$N_8$ is T or C;
$N_9$ is C or G;
$N_{10}$ is G or A;
$N_{11}$ is T or A;
$N_{12}$ is T or G;
$N_{13}$ is T or C;
$N_{14}$ is C or T;
$N_{15}$ is T or C;
$N_{16}$ is T or C;
$N_{17}$ is T or C;
$N_{18}$ is A or T;
$N_{19}$ is A or G;
$N_{20}$ is T or G;
$N_{21}$ is A or T;
$N_{22}$ is A or G;
$N_{23}$ is T or G;
$N_{24}$ is A or G;
$N_{25}$ is T or C;
$N_{26}$ is T or C; and
$N_{27}$ is T or C.

Accordingly, another aspect of the present invention provides an assay for an HBV variant which an altered sensitivity to an agent, said variant HBV comprising a nucleotide sequence comprising a single or multiple nucleotide substitution, addition and/or deletion to the nucleotide sequence set forth in Formula III and which HBV variant has a surface antigen exhibiting altered immunological profile relative to a surface antigen defined by Formula II said method comprising:

generating a genetic construct comprising a replication competent amount of the genome from said variant HBV contained in or fused to an amount of a baculovirus genome capable to infect cells and infecting said cells with said construct;

contacting said cells, before, and/or during, and/or after infection, with the agent to be tested;

optionally further infecting said cells with the same genetic construct or a genetic construct comprising the genome of HBV wild-type or another HBV variant;

culturing said cells for a time and under conditions sufficient for the variant HBV to replicate, express genetic sequences or assemble if resistant to said agent; and subjecting the cells, cell lysates or culture supernatant fluid to viral- or viral-component-detection means to determine whether or not the variant virus has replicated, expressed genetic material or assembled in the presence of said agent.

Generally, the effective amount of HBV genome required to be inserted into the baculovirus genome is functionally equivalent to but comprises more than 100% of an HBV genome. For example, constructs containing approximately 1.05, 1.1, 1.2, 1.28, 1.3, 1.4, 1.5 and 1.6–1.9, 2.0 and 3.0 times the HBV genome are particularly useful.

Any cells which are capable of infection by baculovirus may be used in the practice of the present invention. The hepatoblastoma cell line, HepG2, or its derivatives, is particularly useful and is capable of in vitro cell culture. Huh-7 cells may also be used. Alternatively, any hepatocyte cell line and primary hepatocyte cell culture may be used.

For convenience, a genetic construct comprising an HBV genome and an infection effective amount of baculovirus genome is referred to herein as "HBV baculovirus", "recombinant HBV baculovirus" and "HBV baculovirus vector". Recombinant HBV baculovirus is an efficient vector for the delivery of HBV genetic information to human cells and can be used to initiate HBV gene expression and replication in the cells. HBV transcripts, intracellular and secreted HBV antigens are produced and replication occurs as evidenced by the presence of high levels of intracellular, replicative intermediates and protected HBV DNA in the medium. Viral CCC DNA can be detected indicating that, in this system, HBV core particles are capable of delivering newly synthesized HBV genomes back into the nucleus of infected cells. Strong HBV gene expression can be detected as early as one day post-infected (p.i.) High levels of HBV replicative intermediates, extracellular DNA, and CCC DNA persist through at least 11 days p.i. Endogenous HBV enhancers and promoters may be used to obtain high levels of HBV expression and replication in the cells.

The level of HBV expression and replication in the cells infected with HBV baculovirus can be altered over a considerable range simply by changing the moi.

Furthermore, co-infection or superinfection may occur using the genomes from two or more types of HBV such as two or more HBV variants or a variant and a wild-type strain. In this regard, a number of quasi-species of HBV are generally isolated from subjects infected with HBV which consists of two or more HBV variants, or a variant (or variants) and a wild-type strain. It is important, in some circumstances, to test for these quasi species and to determine the altered sensitivity or resistance of the quasi-species to the therapeutic agents. Nucleic acid or antibody detection systems may be used to detect relative amounts of the different HBVs. This is important for the development of therapeutic protocols which will need to be effective against HBV variants of a single species as well as multiple HBV variants including the wild type strain.

Reference to "HBV" or its "components" in relation to the detection assay includes reference to the presence of RNA, DNA, antigenic molecules or HBV-specific activities. Conveniently, the assay is conducted quantitively, partially quantitively or qualitively. Most preferably, total HBV RNA or DNA is detected which provides an amount of RNA or DNA in the presence of a particular agent. When the HBV variant is more resistant to a particular agent relative to a wild-type strain, then a graphical representation of total RNA or DNA versus concentration of agent is likely to result in a reduced gradient of inhibition and/or an increase in the concentration of agent required before inhibition of RNA or DNA generation.

Another aspect of the present invention provides a method for the detection of polymerase activity from HBV particles isolated from variant HBV baculovirus infected cells and determining the sensitivity of said polymerase to nucleoside triphosphate analogues or non-nucleoside analogues reverse transcriptase inhibitors or non-nucleoside analogues DNA dependent DNA polymerase inhibitors. The HBV particles can be collected from variant HBV cell culture fluid, cell lysates or infected cells. This assay will determine the effect of the said nucleoside triphosphate analogues or non-nucleoside analogues reverse transcriptase inhibitors or non-nucleoside analogues DNA dependent DNA polymerase inhibitors on the reference HBV and variant HBV.

Accordingly, this aspect of the present invention provides a method for detecting a variant HBV comprising DNA polymerase which exhibits an altered sensitivity to an agent, said method comprising:

generating a genetic construct comprising a replication competent amount of the genome from said variant HBV contained in or fused to an amount of a baculovirus genome capable to infect cells and then infecting said cells with said construct;

optionally further infecting said cells with the same genetic construct or a genetic construct comprising the genome of HBV wild-type or another HBV variant;

culturing said cells for a time and under conditions sufficient for the variant HBV to replicate, express genetic sequences and/or assemble and/or release virus or virus-like particles; and subjecting the cells, cell lysates or culture supernatant fluid or HBV particles purified therefrom to a HBV DNA polymerase assay in the presence or absence of nucleoside triphosphate analogues or non-nucleoside analogues reverse transcriptase inhibitors or non-nucleoside analogues DNA dependent DNA polymerase inhibitors.

A further aspect of the present invention provides a method for detecting a variant HBV comprising DNA polymerase which exhibits an altered sensitivity to an agent said method comprising:

generating a genetic construct comprising a replication competent amount of the genome from said variant HBV contained in or fused to an amount of a baculovirus genome capable to infect cells and then infecting said cells with said construct;

optionally contacting said cells, before and/or after infection, with the agent to be tested;

optionally further infecting said cells with the same genetic construct or a genetic construct comprising the genome of HBV wild-type or another HBV variant;

culturing said cells for a time and under conditions sufficient for the variant HBV to replicate, express genetic sequences and/or assemble and/or release virus or virus-like particles if resistant to said agent; and subjecting the cells, cell lysates or culture supernatant fluid or virus purified therefrom to HBV DNA polymerase assay in the presence or absence of nucleoside triphosphate analogues or non-nucleoside analogues reverse transcriptase inhibitors or non-nucleoside analogues DNA dependent DNA polymerase inhibitors.

Yet a further aspect of the present invention contemplates a method of detecting DNA polymerase activity the presence of an antiviral agent, said method comprising:

generating a genetic construct comprising a replication competent amount of a genome from said an HBV capable of producing said DNA polymerase, said genome contained in or fused to an amount of a baculovirus genome capable to infect cells and then infecting said cells with said construct;

contacting said cells, before and/or after infection, with the antiviral agent to be tested;

optionally further infecting said cells with the same genetic construct or a genetic construct comprising the genome of HBV wild-type or another HBV strain;

culturing said cells for a time and under conditions sufficient for the HBV to replicate, express genetic sequences and/or assemble and/or release virus or virus-like particles if resistant to said strain; and subjecting the cells, cell lysates or culture supernatant fluid or virus purified therefrom to HBV DNA polymerase assay in the presence or absence of nucleoside triphosphate analogues or non-nucleoside analogues reverse transciptase inhibitors or non-nucleoside analogues DNA dependent DNA polymerase inhibitors.

The present invention is further described by the following non-limiting Examples.

EXAMPLE 1

Overlapping Genome of HBV

The overlapping genome of HBV is represented in FIG. 1. The gene encoding DNA polymerase (P), overlaps the viral envelope genes, Pre-S1 and Pre-S2, and partially overlaps the X and core (C) genes. The HBV envelope comprises small, middle and large HBV surface antigens. The large protein component is referred to as the HBV surface antigen (HBsAg) and is enclosed by the S gene sequence. The Pre-S1 and Pre-S2 gene sequences encode the other envelope components.

EXAMPLE 2

Amino Acid Consensus Sequence of HBV DNA Polymerase

The amino acid consensus sequence for HBV DNA polymerase protein from genotypes A through G is shown in FIG. 2.

EXAMPLE 3

Consensus Sequence of HBsAg

The nucleotide sequence from various strains of HBV encoding the surface antigen is shown in FIGS. 3A to 3K. The amino acid sequence of the surface antigen beginning at amino acid 108 is shown above the nucleotide sequence.

EXAMPLE 4

HBV Variants Produced by Site Directed Mutagenesis

Table 1 provides a summary of some of the HBV variants produced by site directed mutagenesis.

TABLE 1

HBV varients produced by site directed mutagenesis

| | Corresponding surface (S) mutation |
|---|---|
| Nucleotide analogue selected polymerase mutations | |
| 1. L426V | No change |
| 2. L426I | No change |
| 3. G499E (B domain) | D144E |
| 4. W499Q (B domain) | G145R |
| 5. F512L (B domain) | A157D |
| 6. V519L (B domain) | E164D |
| 7. L526M (B domain) | No change |
| 8. M550V (C domain) | M195I |
| 9. M550V (C domain) | M196L |
| 10. M550I (C domain) | W196S |
| 11. V553I (C domain) | M198I |
| 12. V55EI (C domain) | W199S |
| 13. S565P | S21OR |
| Double polymerase mutations | |
| 14. L526M/M550V | M195I |
| 15. L526M/M550I | W196S |
| 16. L426I/M550I | W196S |
| 17. L426V/M550I | W196S |
| Triple polymerase mutations | |
| 18. V519L/L526M/M550V | E164D/M195I/W196L |
| 19. V519L/L526M/M550I | E164D/W196S |
| 20. L426I/L526M/M550I | W196S |
| 21. L426V/L526M/M550I | W196S |
| Precore and basal core promoter mutations (number from the unique EcoR1 site) | |
| A1814T | |
| C1856T | |
| G1896A | |
| G1897A | |
| G1898A | |
| G1899A | |
| G1896A/G1899A | |
| A1762T/G1764A | |
| T175C | |
| G1757A | |
| G1653T | |

EXAMPLE 5

Cell Culture

Sf21 insect cells were maintained in supplemented Grace's insect medium further supplemented with 10% v/v heat-inactivated fetal bovines serum (Gibco BRL, Gaithersburg, Md.) in humidified incubator at 28° C. with $CO_2$. HepG2 cells were maintained in minimal essential medium supplemented with 10% v/v heat-inactivated fetal bovine serum (MEM-FBS). HepG2 cells were grown in humidified 37° C. incubators at 5% v/v $CO_2$.

EXAMPLE 6

Preparation of Baculovirus Transfer Vector

Figure 4A:
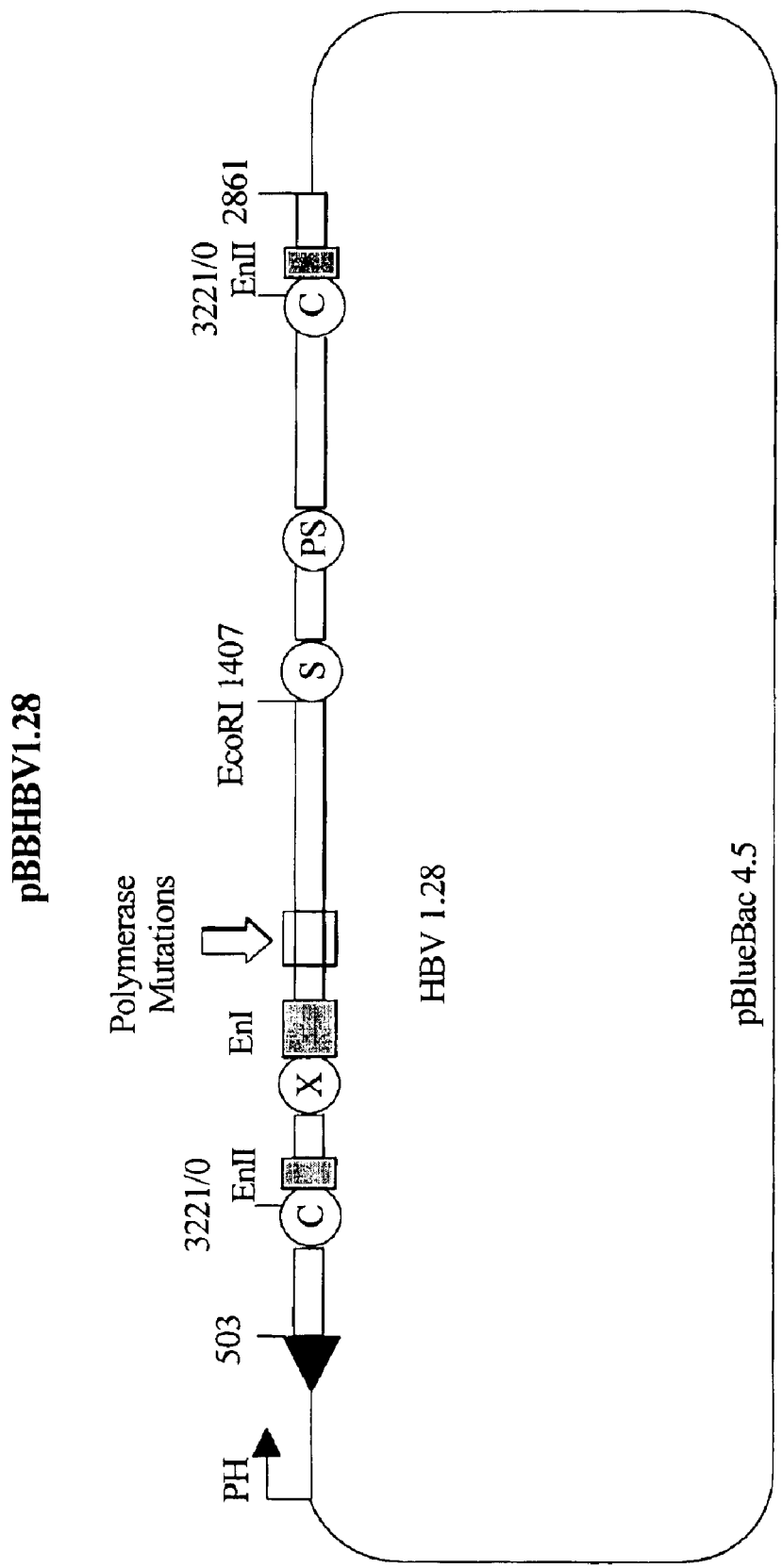
FIG. 4A is a diagrammatical representation of pBBHVB1.28 carrying the HBV 1.28 genome.
Figure 4B:
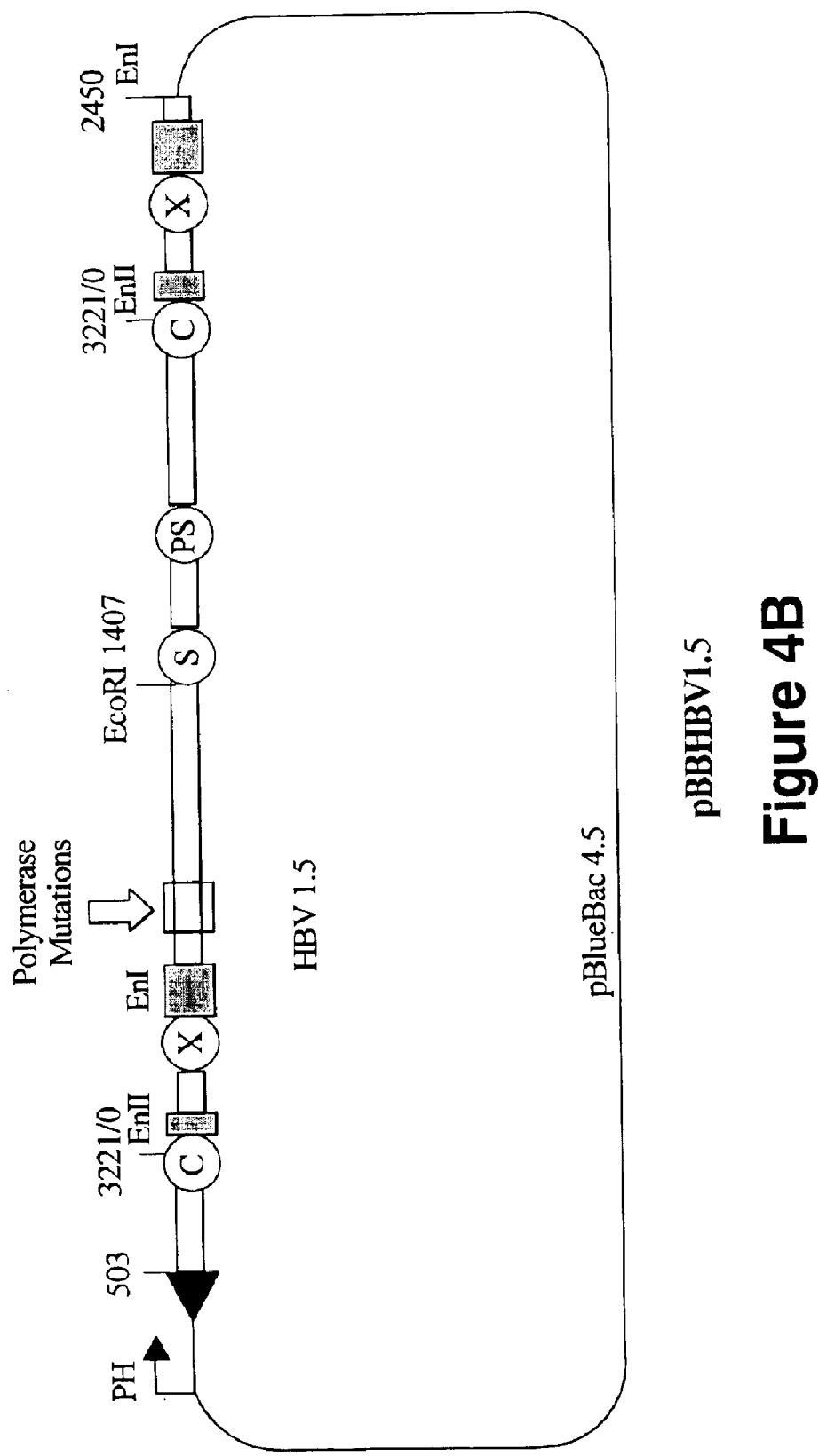
FIG. 4B is a diagrammatical representation of pBBHVB1.5 carrying the HBV 1.5 genome.

A recombinant transfer vector was created by excising a fragment containing the required amount of variant HBV genome construct and cloning it into the multiple cloning region of a baculovirus vector such as pBlueBac4.5 (Invitrogen, Carlsbad, Calif.). FIGS. 4A and 4B show a representation of the plasmid encoding the recombinant transfer vector 1.28 and the 1.5 HBV genome construct, respectively. Similar beculovirus transfer vectors may also be constructed from an HBV 1.3 construct. A diagrammatic representation of the recombinant transfer vector HBV 1.3 is shown in FIG. 1 of International Patent Application No. PCT/US99/01153 [WO 99/37821]. Analysis of recombinant transfer vector by restriction mapping demonstrated the presence of only one copy of the HBV genome portion in the construct. The nucleotide sequence of the plasmid and the point mutations generated by site directed mutagenesis were confirmed by sequencing using the ABI Prism Big Dye Terminator Cycle Sequencing Ready Reaction Kit according to the manufacturer's specifications (Perlin Elmer, Cetus Norwalk, Conn.).

EXAMPLE 7

The Sequence of 1.28 HBV Genome and the 1.5 HBV Genome

The sequence of the 1.28 and the 1.5 HBV genome (FIGS. 5A to 5F and FIGS. 14A to 14F, respectively) were elucidated using the ABI Prism Big Dye Terminator Cycle Sequencing Ready Reaction Kit according to the manufacturer's specifications (Perkin Elmer, Cetus Norwalk, Conn.).

EXAMPLE 8

Generation of Recombinant Baculoviruses Containing the 1.28, 1.5 or 1.3 HBV Construct Purified recombinant transfer vector and linear AcMNPV baculovirus DNA were co-transfected into Sf21 cells using the BacNBlue transfection kit from Invitrogen (Carlsbad, Calif.); recombinant viruses were isolated by plaque assay according to the manufacturer's instructions. A series of recombinant viruses were amplified from isolated plaques by infecting 100-mm dishes of Sf21 cells. Viral DNA was extracted from amplified viruses using standard procedures. Purified viral DNA was digested with restriction enzymes and then fractionated by electrophoresis in a 1.0% v/v agarose gel. Southern blotting was performed to determine which virus isolates contained the intact 1.28, 1.5 or 1.3 HBV construct. A Boehringer Mannheim Randorn Prime DNA Labeling kit, Indianapolis, Ind.) was used to generate [$P^{32}$]-radiolabeled probes. A full-length double-stranded HBV genome was used as a template for all radiolabeled probes. Viral DNA sequence was confirmed by PCR amplification of the polymerase catalytic region using the sense primer 5'-GCC TCA TTT TGT GGG TCA CCA TA-3' (SEQ ID NO: 1) (nucleolide 1408 to 1430 according to HBV Genebank Accession number M38454) and the antisense primer 5'-TCT CTG ACA TAC TTT CCA AT-3' (SEQ ID NO.: 2)(nucleotides 2817 to 2798 according to HBV Genebank Accession number M38454). The following primers were utilized for the sequencing of internal regions 5'-TGC ACG ATT CCT GCT CAA-3' (SEQ ID NO: 3) (nucleotides 2345–2362 according to HBV Genbank Accession number M38454) and 5'-TTT CTC AAA GGT GGA GAC AG-3' (SEQ ID NO: 4) (nucleotides 1790–1810 according to HBV Genbank Accession number M38454).

EXAMPLE 9

Preparative Baculovirus Amplification and Purification

Baculoviruses were amplified by infecting suspension cultures of Sf21 cells in log phase at a multiplicity of infection (moi) of 0.5 pfu/cell. Infections were allowed to proceed until a majority of the cells in the flasks showed visible signs of infection (four to five days). Virions were concentrated from infected Sf21 medium by centrifugation at 80,000×g and purified through a 20–60% w/v sucrose gradient. Purified virus was titrated in quadruplicate in Sf21 cells by end-point dilution. An aliquot of each high titre stock was used for DNA extraction. The polymerase gene was amplified and sequenced to confirm the presence of the site-directed mutagenesis as in Example 8.

EXAMPLE 10

Infection of HepG2 Cells with Recombinant HBV Expressing Baculovirus

HepG2 cells were seeded at approximately 20–40% confluency and then were grown for 16–24 hours before infection. On the day of infection, triplicate plates of cells were trypsinized, and viable cell number was determined with a hemocytometer using Trypan blue exclusion. Average cell counts were calculated and used to determine the volume of high-titer viral stock necessary to infect cells at the indicated moi. HepG2 cells were washed one time with serum-free MEM to remove traces of serum. Baculovirus was diluted into MEM without serum to achieve the appropriate moi using volumes of 1.0, 0.5, and 0.25 ml to infect 100-mm, 60 mm, and 35-mm dishes, respectively. Baculovirus was adsorbed to HepG2 cells for one hour at 37° C. with gentle rocking every 15 minutes to ensure that the inoculum was evenly distributed. The inoculum was then aspirated and HepG2 cells were washed two times with phosphate-buffered saline and refed MEM-FBS with or without various concentrations of agents.

EXAMPLE 11

Analysis of Secreted HBV Anitigens

Detection of hepatitis B surface antigen (HBsAg) and hepatitis B e antigen (HBeAg) was performed by radioimmunoassay and microparticle enzyme immunoassay using kits purchased from Abbott Laboratories (Abbott Park, Ill.). Medium from HepG2 cells was collected, centrifuged at 6,000 g to remove cellular debris, transferred to clean tubes, and stored at 20° C. until analysis. HBsAg amounts were calculated from a standard curve constructed using known amounts of HBsAg (provided with the kit). HBeAg values are expressed as fold of positive control. Medium samples were diluted appropriately so that radioimmunoassay results were within the standard curve (HBsAg) or below positive control values (HBeAg).

EXAMPLE 12

Detection of Intracellular Replicative Intermediates

HBV core particles were isolated from the cytoplasmic fraction of HepG2 cells lysed in 0.5% w/v NP-40. Cytoplasmic extracts were adjusted to 10 mmol/l McC12 and unprotected DNA was removed by an incubation to 500 μg/ml Proteinase K for 1.5 hours at 37° C. Following sequential phenol and chloroform extractions, nucleic acids were recovered by ethanol precipitation. Nucleic acids were resuspended in 50 μl/l TE (10 mmol/l Tris, 1 mmol/l ethylenedianinetetraacetic acid), normalized by OD260, and digested with 100 μg/ml RNase (Boehringer Mannheim, Indianapolis, Ind.) for one hour at 37° C. before analysis by electrophoresis and Southern blotting. A BioRad GS-670 imaging densitometer and the Molecular Analyst software (BioRad, Hecules Calif.) was used to analyze suitable exposures of Southern blots. Densitometry data was fitted to logistic dose response curves using the TableCurve2D software package from Jandel Scientific. Logistic dose response equations were used to calculate $IC_{50}$ and $IC_{90}$ values and co-efficients of variation.

EXAMPLE 13

Extracellular HBV DNA Analysis

Conditioned medium was collected from HepG2 cells and subjected to centrifugation at 6,000 g for five minutes to remove cellular debris. HBV particles were precipitated with 10% w/v PEG 8000 and were concentrated by centrifugation at 12,000 ×g. Viral pellets were resuspended us 1 ml of MEM-FBS and divided into two aliquots. One set of aliquots was treated with 750 μg/ml Pronase for one hour and then with 500 mg/ml DNase 1 for one hour. Both sets of aliquots were then digested with Proteinase K, and extracted with phenol and chloroform. DNA was precipitated with 0.1 volume of 3 mol/l sodium acetate and 1 volume of isopropanol. Ten micrograms of transfer RNA was added as a carrier during precipitation. Pellets were resuspended in 25 μl of TE and digested with 0.5 mg/ml RNase for one hour. DNA was then analyzed by electrophoresis and Southern blotting.

EXAMPLE 14

3TC, PMEA and PCV Treatments

3TC and PCV were a gift from Klaus Esser, SmithKline Beecham, Collegeville, Pa. PMEA was obtained from Gilead (Foster City, Calif.). 3TC was resuspended in sterile water, aliquoted, and frozen at −20° C. to avoid repeated freezing and thawing of the drug. PMEA was resuspended in sterile water after the pH was adjusted to 7.0 with NaOH. PCV was resuspended in dimethyl sulphoxide. Medium containing 3TC was prepared daily as needed using fresh aliquots of 3TC. In experiments in which 3TC treatment was initiated after viral infection, HepG2 cells were exposed to the indicated concentration of 3TC immediately after infection with HBV baculovirus. In experiments utilizing pre-treatment with 3TC, cells were fed medium containing 3TC 16 hours prior to HBV baculovirus infection, HBV baculovirus infection was also carried out in medium containing 3TC, and cells were refed fresh medium containing 3TC immediately after completion of the infection and washing procedures. Treatment with PMEA and PCV were conducted in a similar manner.

EXAMPLE 15

1. Antiviral Testing Performed with Wild-Type HBV Baculovirus

Figure 6A:
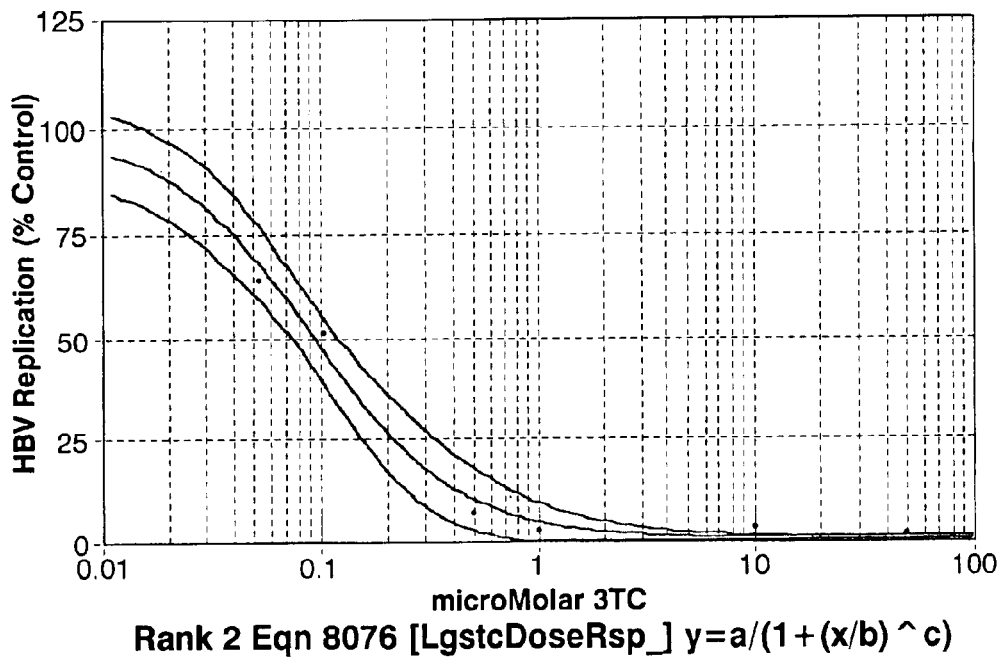
FIGS. 6A and 6B are graphical representations of antiviral testing performed with wild-type HBV baculovirus using A, 3TC; B, PMEA.
Figure 6B:
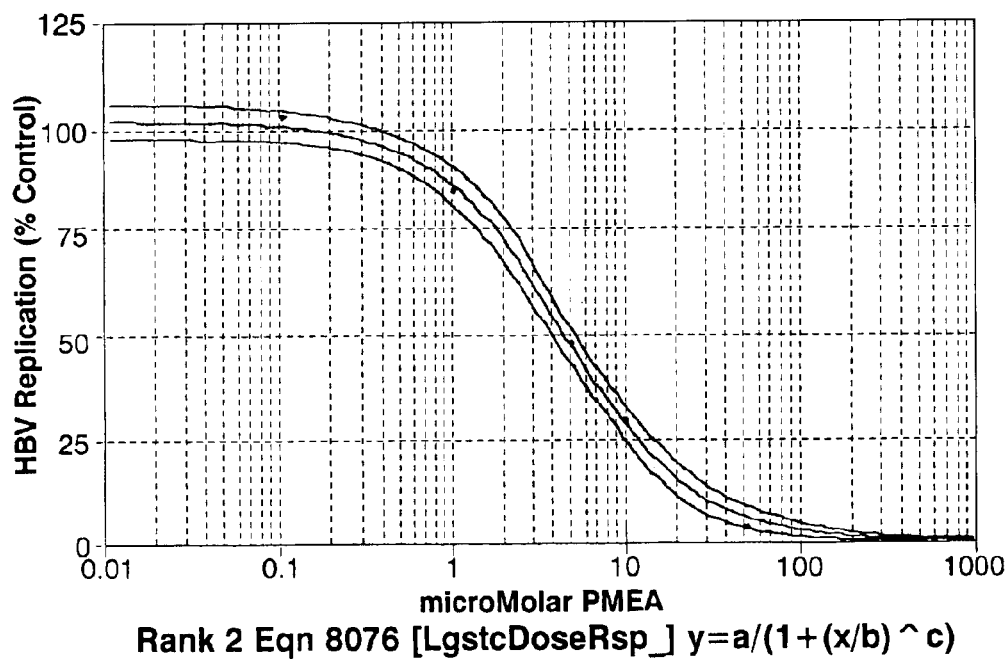
Figure 6C:
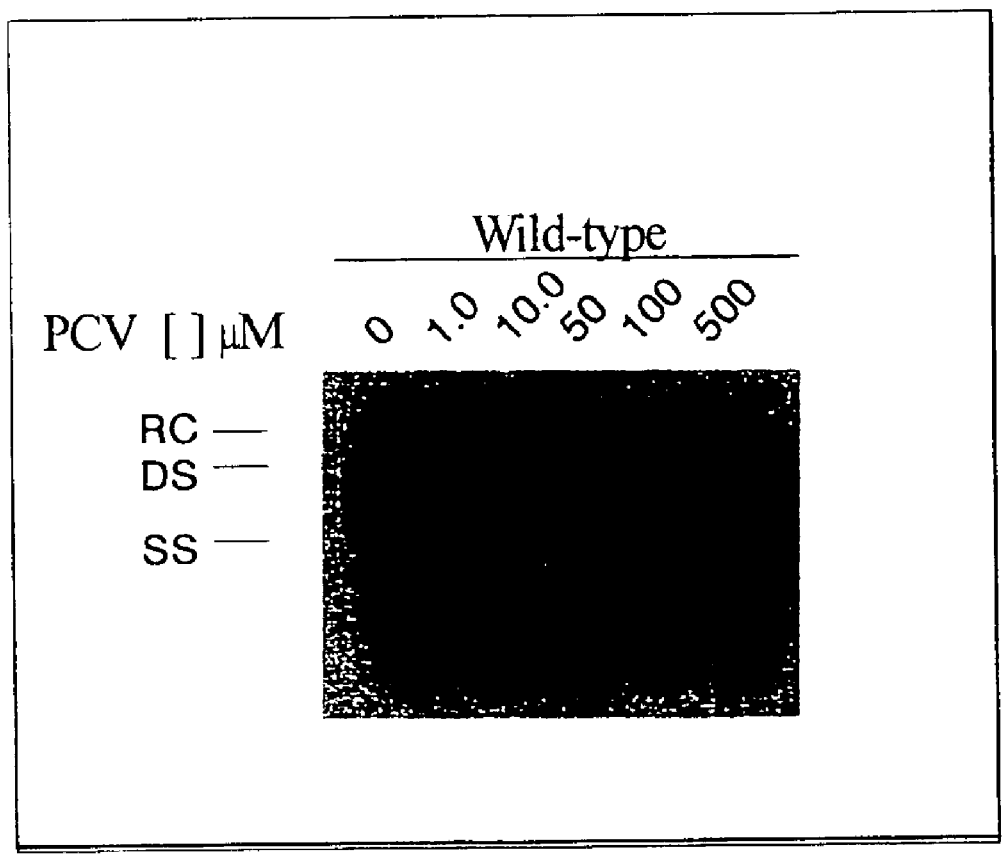
FIG. 6C is a photographic representation of a Southern blot showing the effect of PCV on wild-type HBV baculovirus.

The dose effect of 3TC and PMEA, on wild-type HBV is shown graphically in FIG. 6 (A, B,) and a Southern Blot of intracellular HBV replicative intermediates and extracellular virus produced by HepG2 cells transduced with wild-type HBV-baculovirus in the presence of increasing concentrations of PCV is shown in FIG. 6C and the $IC_{50}$ for each antiviral agent is shown in Table 2. 3TC had the most pronounced effect whereas PCV had a modest effect on wild-type HBV replication.

2. Antiviral Testing with L526M HBV Baculovirus

Figure 1B:
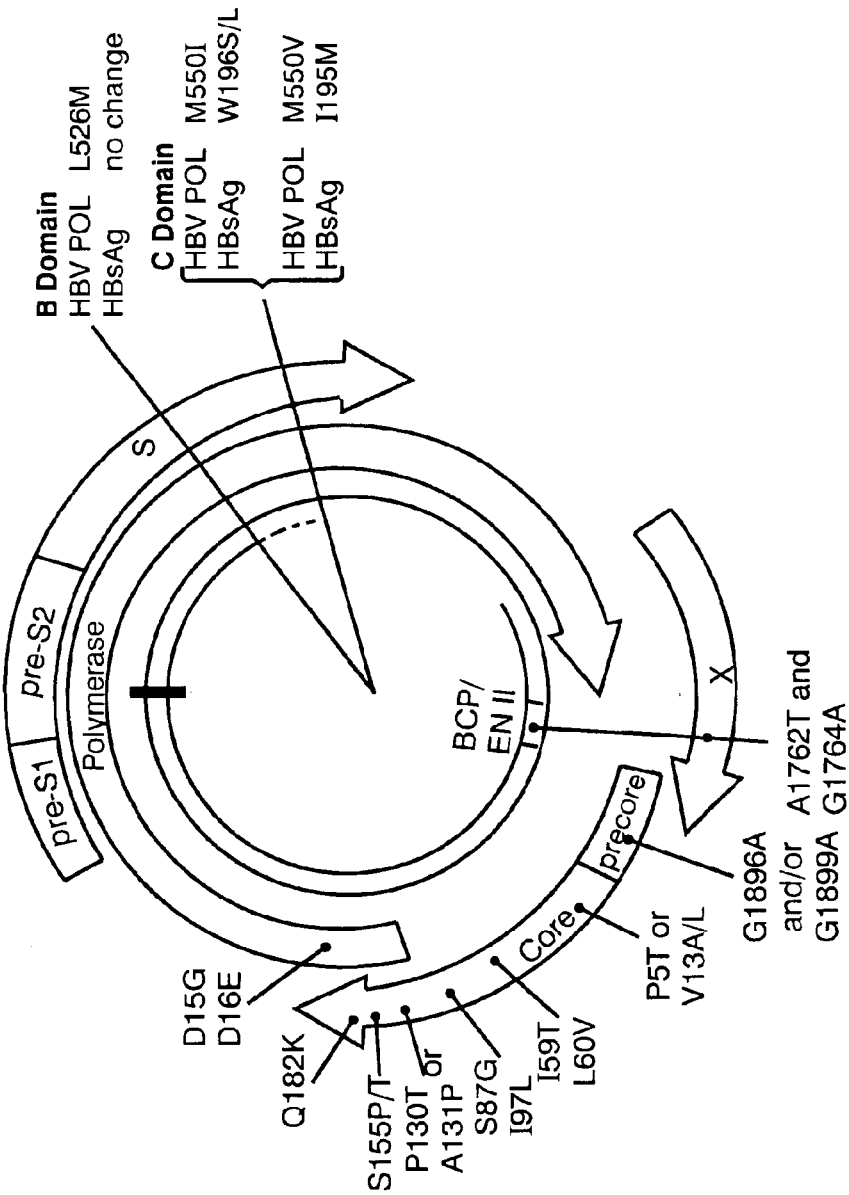
FIG. 1B is a diagrammatic representation showing examples of the major mutations detected in the precore, envelope and polymerase genes.
Figure 7A:
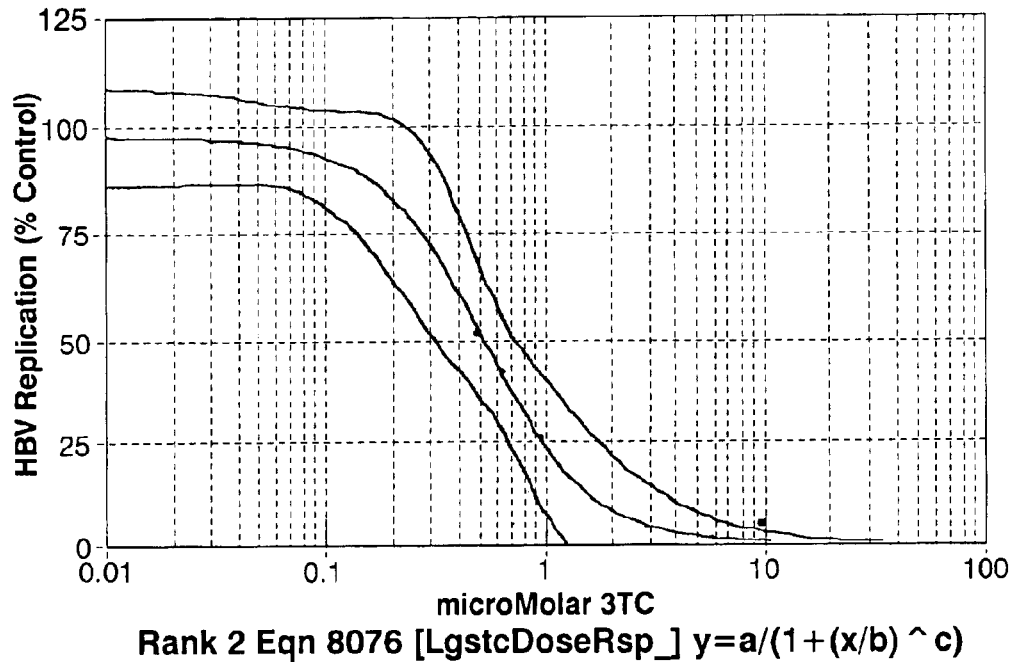
FIGS. 7A to 7C are graphical representations of antiviral testing performed with L526M HBV baculovirus using A, 3TC; B, PMEA; C, PCV.
Figure 7B:
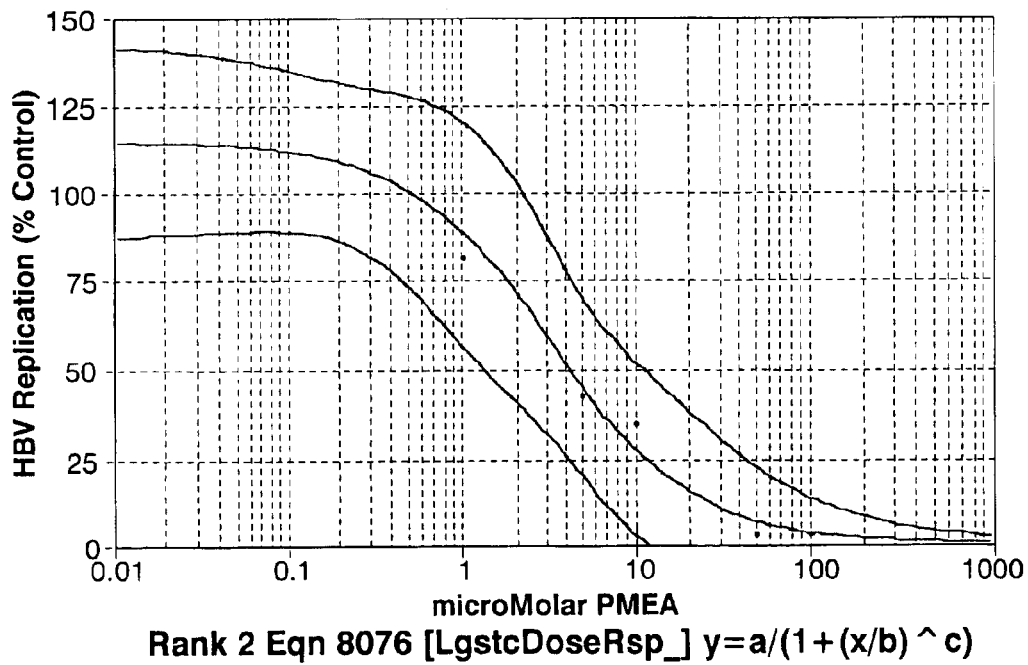
Figure 7C:
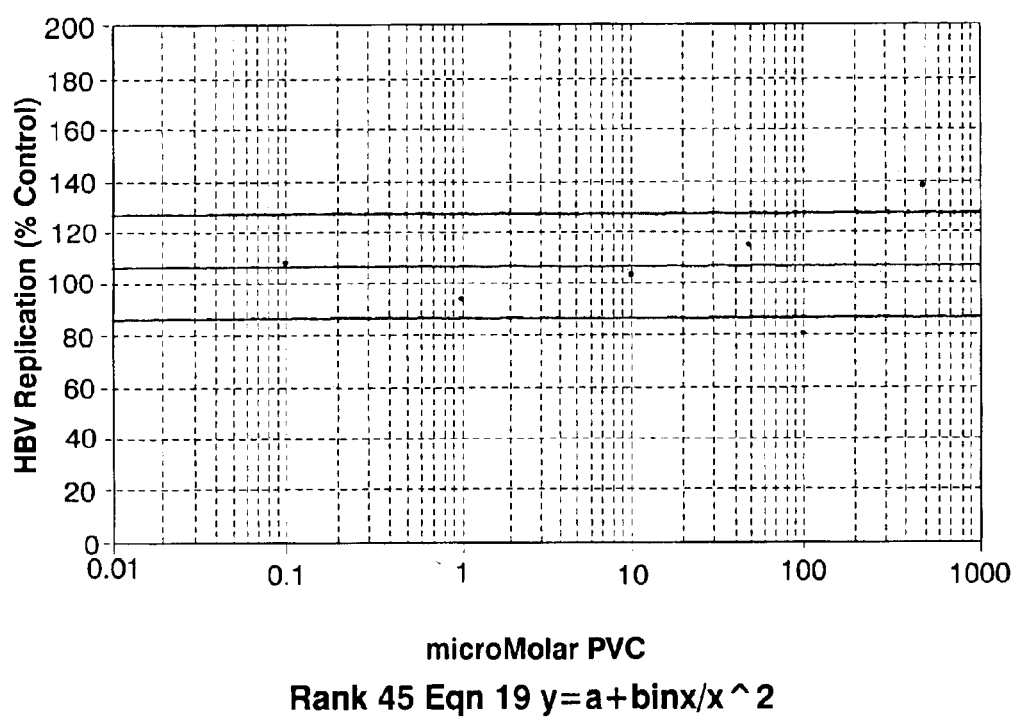

FIG. 7A shows a pronounced resistance of L526M to 3TC compared to the wild-type in FIG. 1A in which there was >0.5 log shift in the $IC_{50}$. No significant change was observed with PMLA or PCV (FIGS. 7B, 7C).

3. Antiviral Testing with L526M/M550V HBV Baculovirus

Figure 8A:
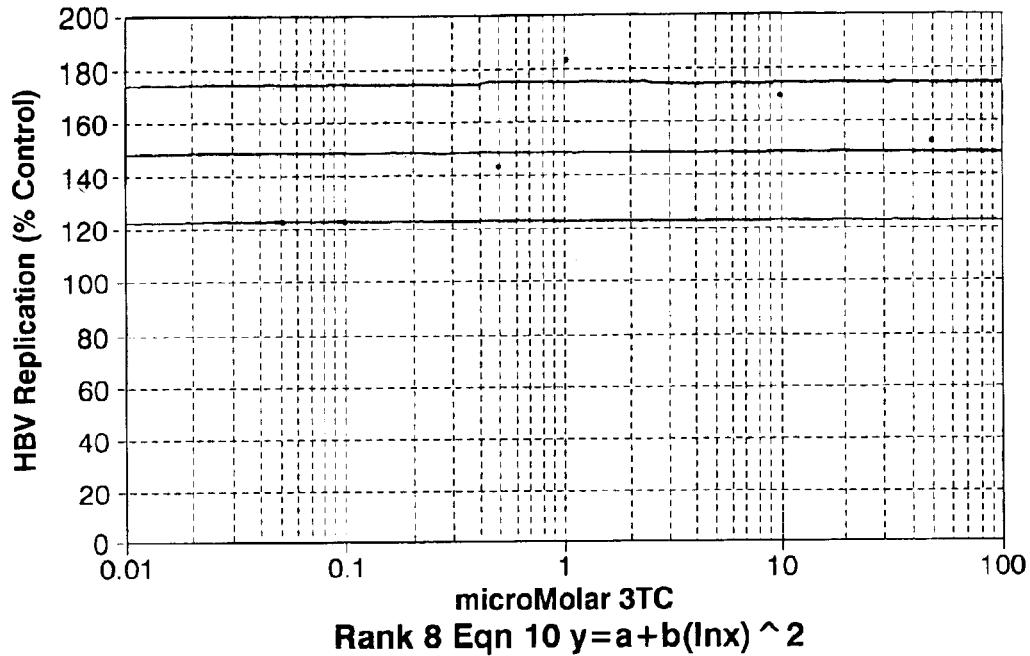
FIGS. 8A to 8C arc graphical representations of antiviral testing performed with L526M/M550V HBV baculovirus using A, 3TC; B, PMEA; C, PCV.
Figure 8B:
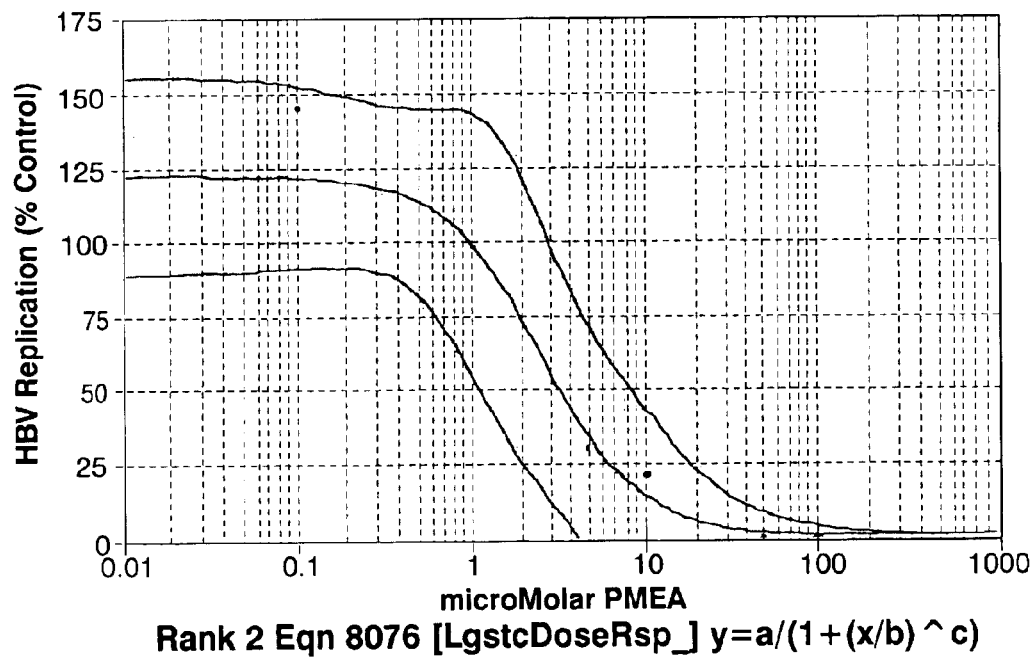
Figure 8C:
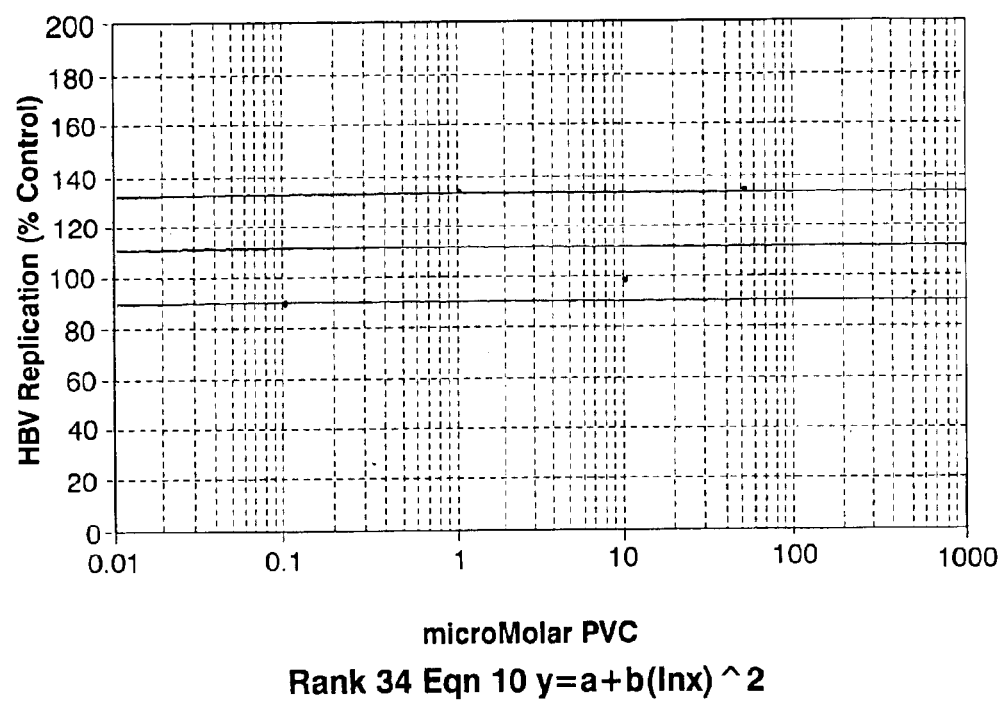

FIG. 8A shows that L526M/M550V is completely resistant to 3TC. There was no substantial change to PMBA or PCV (FIGS. 8B, 8C).

4. Antiviral Testing with M550I HBV Baculovirus

Figure 9A:
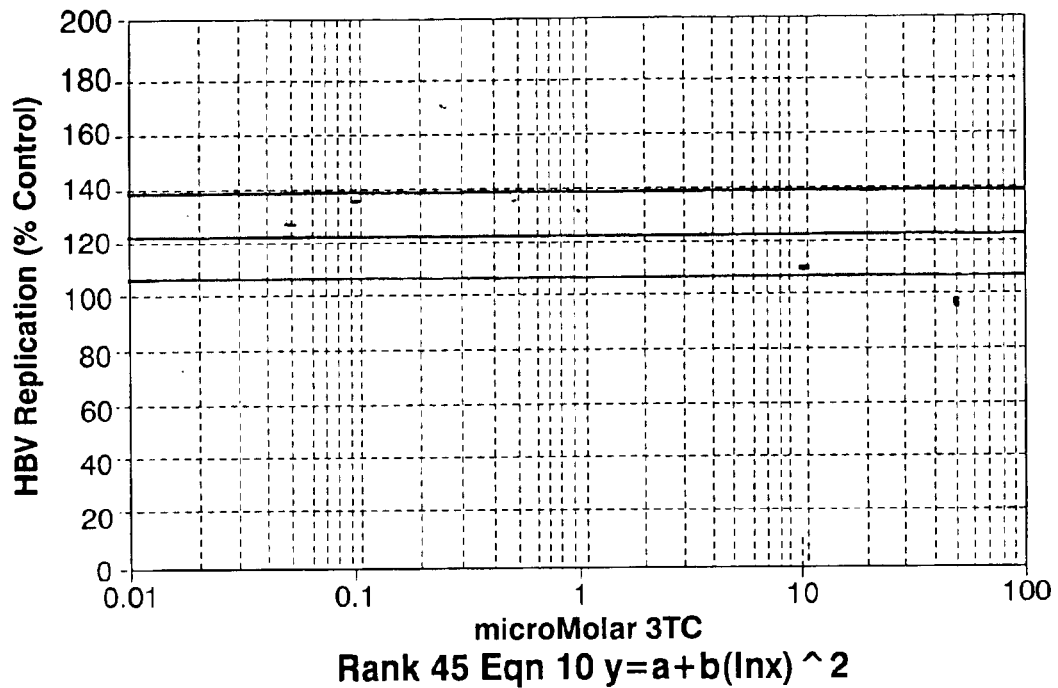
FIGS. 9A to 9C are graphical representations of antiviral testing performed with M550I HBV baculovirus using A, 3TC; B, PMEA; C, PCV.
Figure 9B:
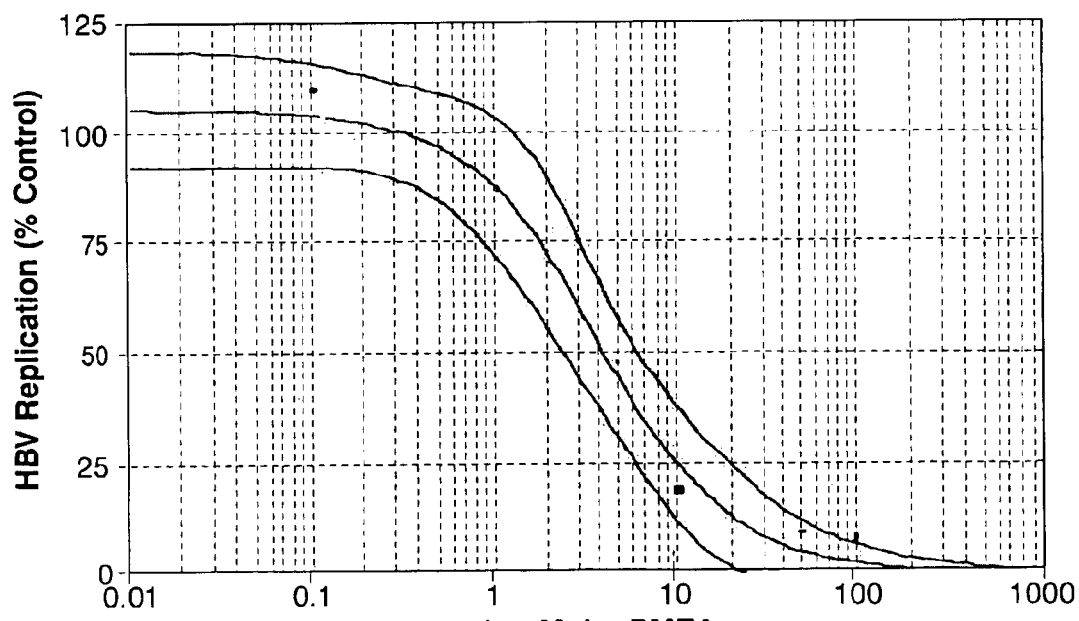
Figure 9C:
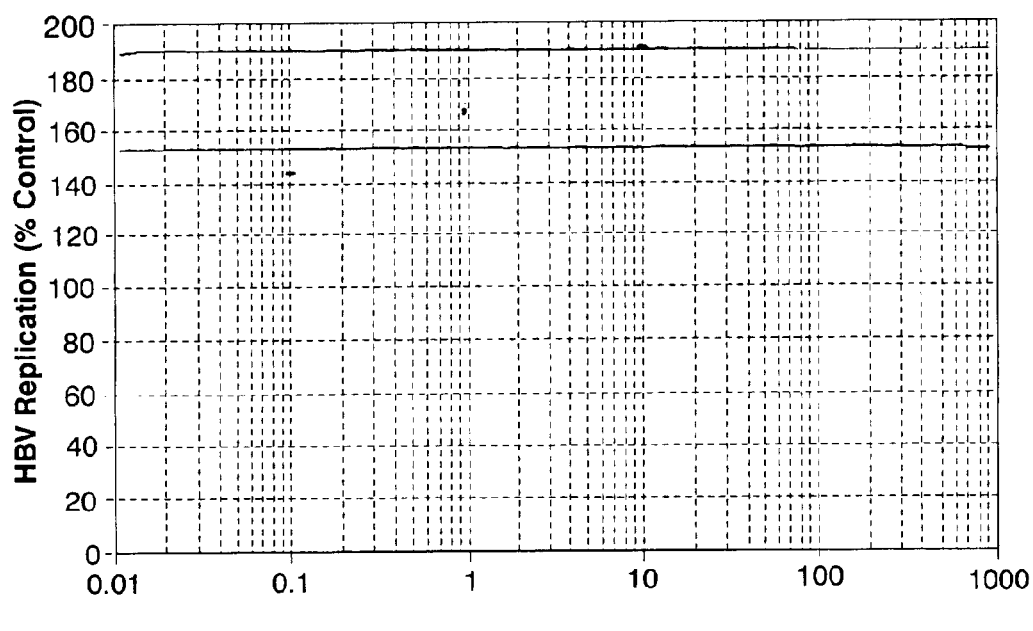

M550I is completely resistant to 3TC (FIG. 9A). The M550I HBV baculovirus had a similar sensitivity to PMEA as the wild-type virus as in FIG. 9B.

TABLE 2

Sensitivity of replication of wt and mutant HBV to inhibition by Lamivudine, Penciclovir and Adefovir

| HBV | | Equation Parameters | | | Correlation | Inhibition | Sensitivity Parameters | Resistance |
|---|---|---|---|---|---|---|---|---|
| | | a | b | c | ($r^2$) | at 1 μM | $IC_{50}$ (μM) | Factor |
| | | | | | Lamivudine | | | |
| wt | | 185 ± 8 | 0.004 ± 0.001 | 1.10 ± 0.07 | 1.0 | 99.6 | 0.009 | 1 |
| 526 | | 102 ± 18 | 0.027 ± 0.04 | 0.51 ± 0.27 | 0.89 | 85.8 | 0.03 | 3 |
| 550 | | 186 ± 48 | 0.35 ± 0.64 | 0.42 ± 0.26 | 0.93 | 26.7 | 3.8 | 422 |
| dual | | 127 ± 10 | 41.5 ± 31 | 0.60 ± 0.4 | 0.90 | (−15)** | 86.2 | 9578 |
| | | | | | Penciclovir | | | |
| wt | | 101 ± 2 | 11.2 ± 0.95 | 1.0 ± 0.06 | 1.0 | 7.0 | 11.5 | 1 |
| 526 | I | 100 ± 7 | 103 ± 12 | 4.8 ± 7.3 | 0.93 | (−3.0) | 103 | 9 |
| 550 | | 124 ± 6 | 0.0007 | —* | 0.73 | (−24) | 1217*** | 106 |
| dual | | 111 ± 7 | 0.002 | —* | 0.86 | (−10) | 370 | 32 |
| | | | | | Adefovir | | | |
| wt | | 170 ± 16 | 0.025 ± 0.001 | 0.80 ± 0.07 | 1.0 | 91.6 | 0.08 | 1 |
| 526 | | 203 ± 49 | 0.014 ± 0.01 | 0.61 ± 0.08 | 1.0 | 86.2 | 0.09 | 1 |

TABLE 2-continued

Sensitivity of replication of wt and mutant HBV to inhibition by Lamivudine, Penciclovir and Adefovir

| HBV | Equation Parameters | | | Correlation $(r^2)$ | Inhibition at 1 $\mu$M | Sensitivity Parameters IC$_{50}$ ($\mu$M) | Resistance Factor |
|---|---|---|---|---|---|---|---|
| | a | b | c | | | | |
| 550 | 159 ± 24 | 0.078 ± 0.05 | 0.57 ± 0.1 | 1.0 | 70.0 | 0.31 | 4 |
| dual | 155 ± 8 | 0.039 ± 0.009 | 0.53 ± 0.02 | 1.0 | 77.0 | 0.16 | 2 |

Footnote to Table 2
Measurements were made by assessing the image density of the ds HBV DNA bands in each autoradiograph and expressing the result as a percentage of the mean density of untreated controls.
Logistic dose response (LDR) equations did not accurately describe these data sets; instead the a and b parameters are for a single exponential decay equation $y = a^{(-bx)}$
Values given are means or means ± standard errors. In several cases, low concentrations of inhibitor stimulated HBV replication, reflected by a values >100%. The percentage inhibition which occurs at a drug concentration of 1 $\mu$M has been estimated from each fitted curve plot; negative values (**) represent stimulation of replication relative to controls.
***Extrapolated value.
The "Resistance Factor" is the factor (to the nearest integer) by which IC$_{50}$ estimated for the mutants differ from the corresponding estimate for wt, calculated by dividing the mutant IC$_{50}$ by wt IC$_{50}$.

EXAMPLE 16

1. Preparation of HBV Particles from HBV Baculovirus Infected Cells

HepG2 cells were infected with 1.5 HBV baculovirus at an moi of 50–200. Starting on day three post infection, conditioned medium was collected from infected cells, centrifuged at 3000×g to remove cellular debris, and stored frozen at −20° C. HBV particles were concentrated from conditioned medium by ultra-centrifugation in an SW28 rotor at 27,000 rpm for 5 hours. Pelleted virus was resuspended in a small volume phosphate-buffered saline, aliquoted and frozen at −20° C.

2. Endogenous Polymerase Assay Using HBV Particles Prepared from HBV Baculovirus Infected Cells Aliquots of virus were thawed and brought to a final concentration of 0.5% NP-40, 2.5 mM Tris pH 7.5, and 6 mM DTT for 10 minutes at room temperature to disrupt the viral envelope. The virus solution was then brought to 150 mM NaCl, 10 mM MgCl$_2$, 20 mM KCL and 10 mM dATP, dGTP and dTTP. 10 mC of $^{32}$P-labled dCTP (approximately 0.2 mM) was added and the reaction was incubated at 37° C. for 40 minutes to allow the HBV polymerase to extend the viral DNA genome. In order to stop the reaction it was adjusted to 0.5% SDS, 25 mM Tris, and 10 mM EDTA. The reaction mixture was digested with 500 $\mu$g/ml of proteinase K overnight at 37° C. and HBV DNA was purified from by one extraction with 1:1 phenol:chloroform followed by ethanol precipitation. DNA pellets were resuspended in a small volume of water and electrophoresed through 1% w/v agarose gels for 2 hours. Gels were dried using a Biorad gel dryer and autoradiography of the dried gels was performed to visualize the amount of $^{32}$P-labelled dCTP incorporated into HBV genomes by HBV polymerase.

Figure 10:
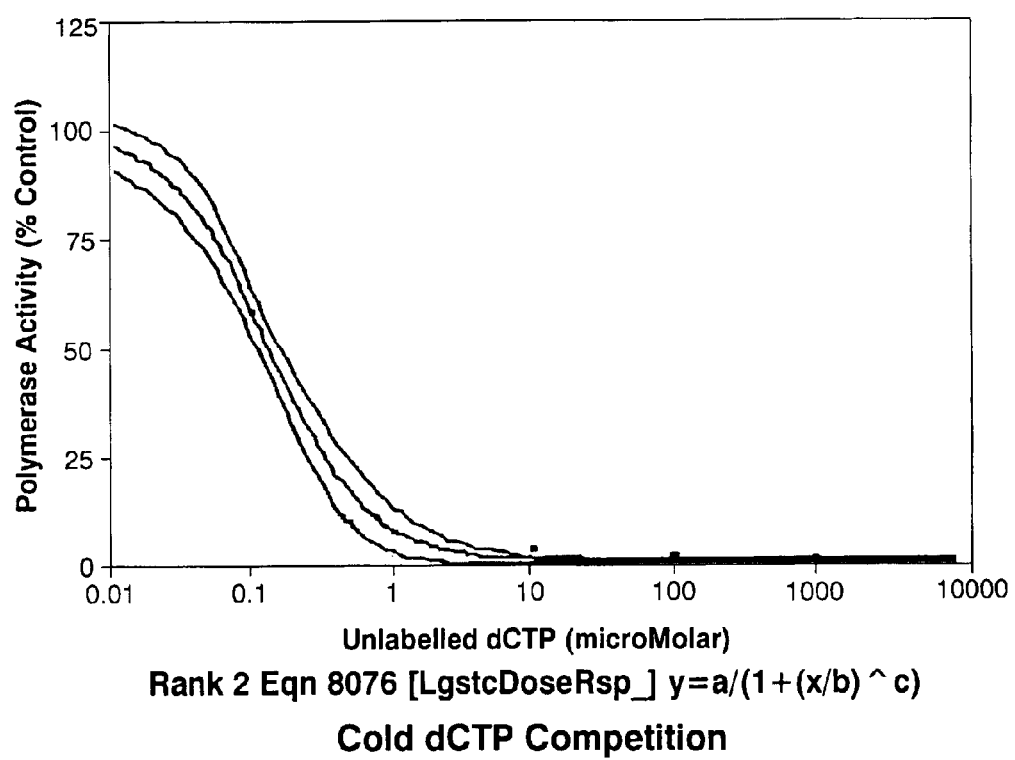
FIG. 10 is a graphical representation showing the competition of radio-labelled [$\alpha^{32}$P]-dCTP by cold dCTP using the endogenous polymerase assay with particles prepared from baculovirus infected cells.
Figures 11A, 11B:
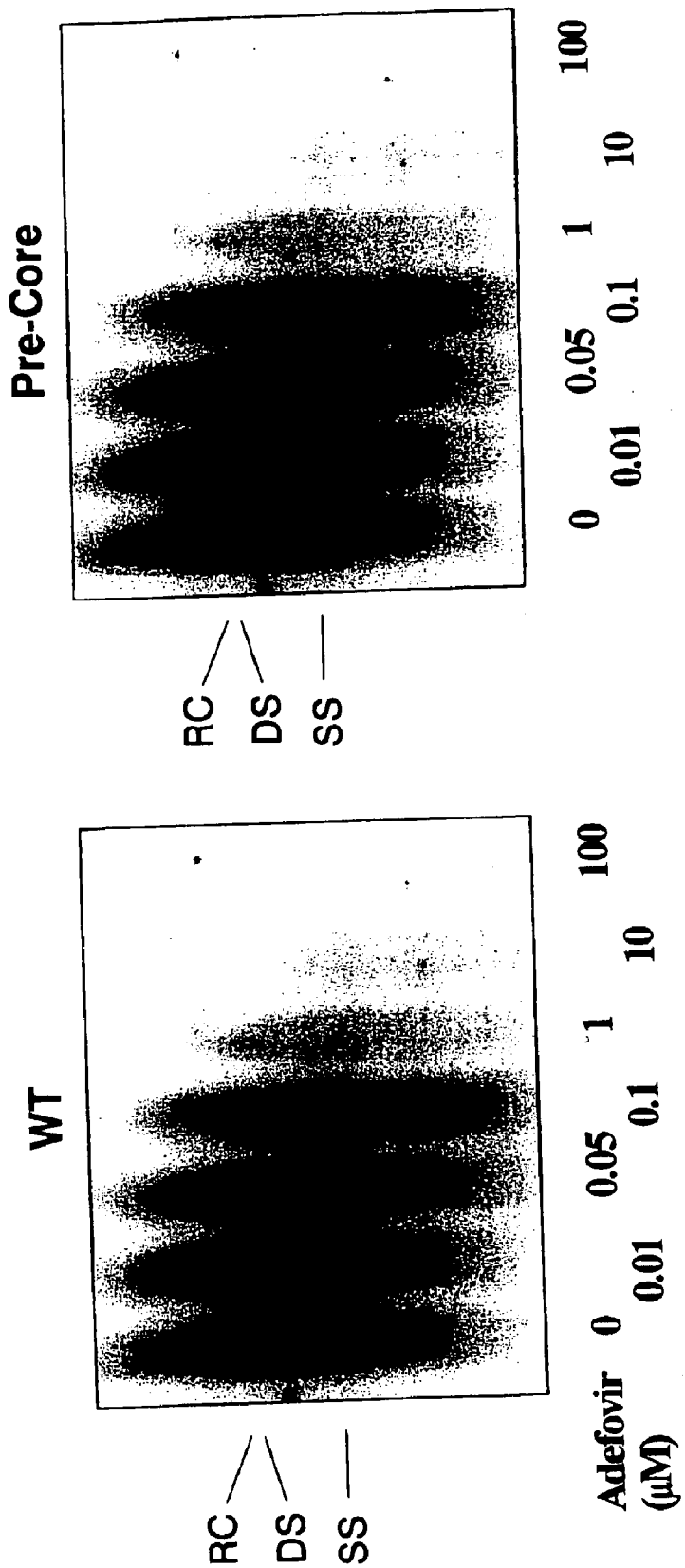
FIGS. 11A to 11F are photographic representations showing Southern blot of the intracellular and extracellular HBV DNA production from HepG2 cells transduced with wild-type (WT) and precore (G1 896A) recombinant HBV-baculovirus exposed to increasing concentrations of (A) adefovir, (B) lamivudine and (C) penciclovir. IC, intracellular; EC, extracellular; RC, relaxed circular HBV DNA; DS, linear double-standard HBV DNA; SS, single-stranded HBV DNA.
Figures 11C, 11D:
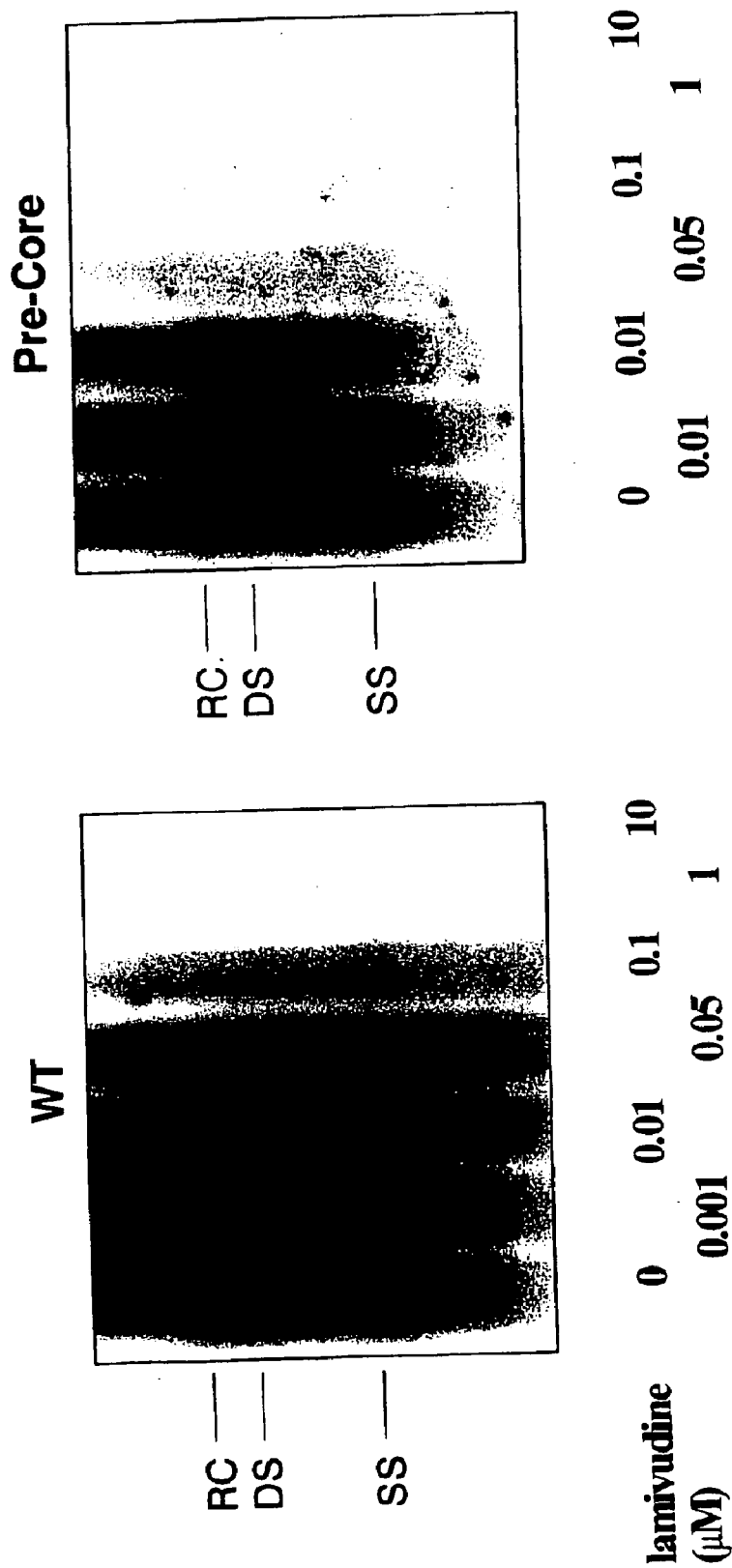
Figures 11E, 11F:
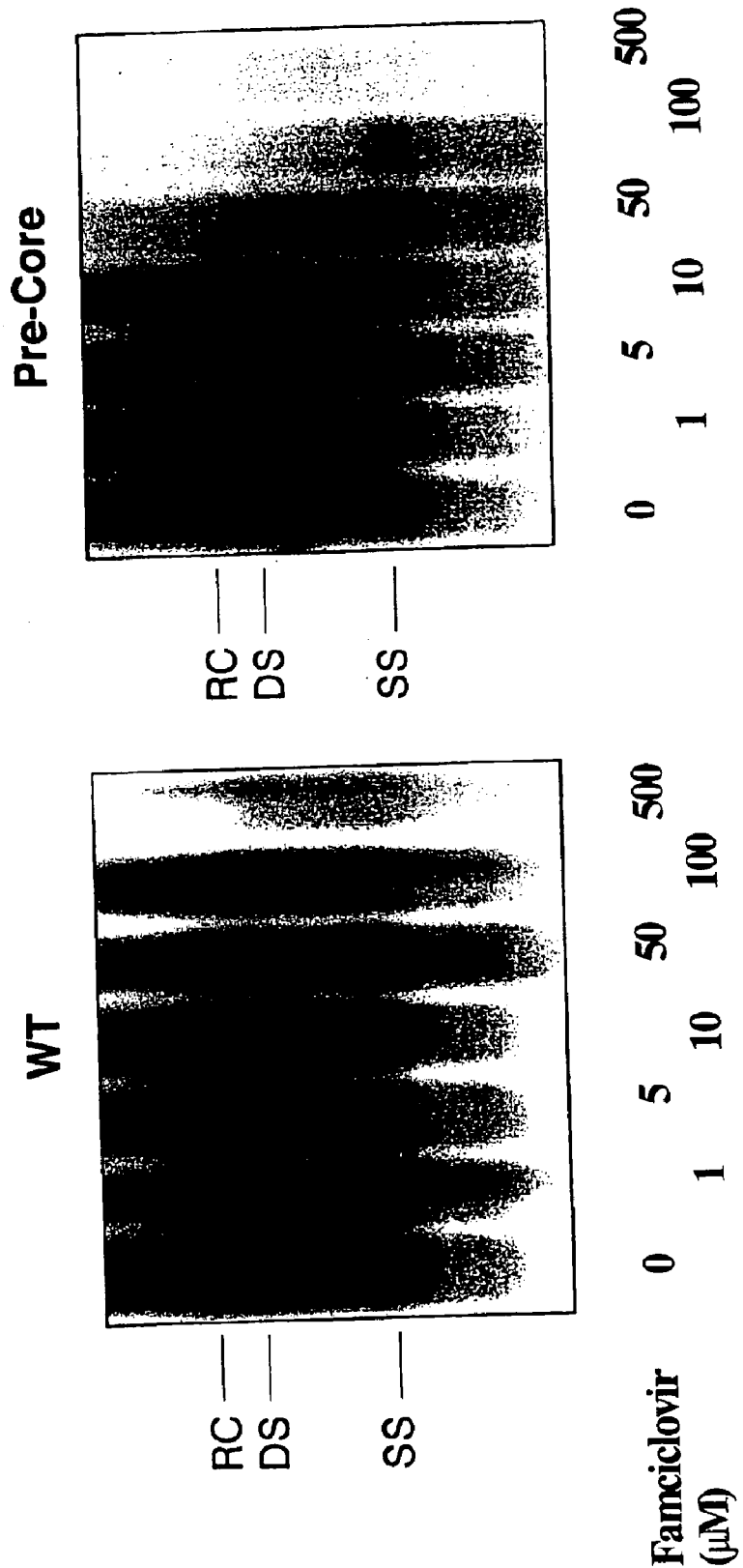

3. An Assay to Measure the Competition of Radio-Labelled [a$^{32}$P]-dCTP Incorporation by Cold dCTP Using the Endogenous Polymerase Assay Using HBV PARTICLES Prepared from Baculovirus Infected Cells Polymerase assays were performed as described above except that cold dCTP was added to each reaction to compete with the incorporation of labelled dCTP. In separate reactions, concentrations of 01, 1, 10, 100, and 1000 mM were added at the same time as labelled dCTP and the polymerase reactions were allowed to proceed. After an extraction of viral DNA and analysis by gel electrophoresis and autoradiography, the amount of labelled DNA from each reaction was quantified by densitometery of the audioradiogram. Densitometry data were fitted to logistic dose response curves using Tablecurve2D software. FIG. 10 shows the effect of the competition of cold dCTP on $^{32}$P-labelled dCTP.

4. An Assay which can be Used to Measure the Efficacy of an Antiviral Agents in an Endogenous Polymerase Assay, Using HBV Particles Prepared from Baculovirus Infected Cells In an analogous manner, to that described in the above example, the efficacy of antiviral agents such as nucleotide triphosphates and non-nucleoside analogue polymerase inhibitors in inhibiting the catalytic activity of the HBV polymerase can be tested using this assay. The nucleoside triphosphates includes compounds such as 3TC-triphosphate, PMEA-triphosphate or PCV-triphosphate. Polymerase assays can be performed as described in Example 20 part (2), except that various concentrations of an antiviral agent can be added to each reaction to compete with the incorporation of labelled dCTP or another radiolabelled deoxynucleotide triphosphate. In separate reactions, various concentrations of the agents are added at the same time as labelled dCTP and the polymerase reactions are allowed to proceed. After an extraction of viral DNA and analysis by gel electrophoresis and autoradiography, the amount of labelled DNA from each reaction is quantified by densitometery of the audioradiogram. Densitometry data is fitted to logistic dose response curves using Tablecurve2D software.

EXAMPLE 17

1. Antiviral Testing of the Precore Mutant (G1869A) HBV Baculovirus

In this study, comparable HBV DNA production by wild-type (1.3×genomic length HBV) and the precore mutant HBV was found using the recombinant HBV-baculovirus system. The dose effect of lamivudine, adefovir, and penciclovir on the wild-type HBV/baculovirus virus and the precore mutant (G1896A) HBV are shown in FIGS. 11A to 11F, and the calculated IC50 is shown in Table 3. HBV with the specific mutation of GI896A seemed to be at least as sensitive for adefovir, and may be more sensitive to lamivudine and penciclovir compared with wild type HBV.

Figure 12:
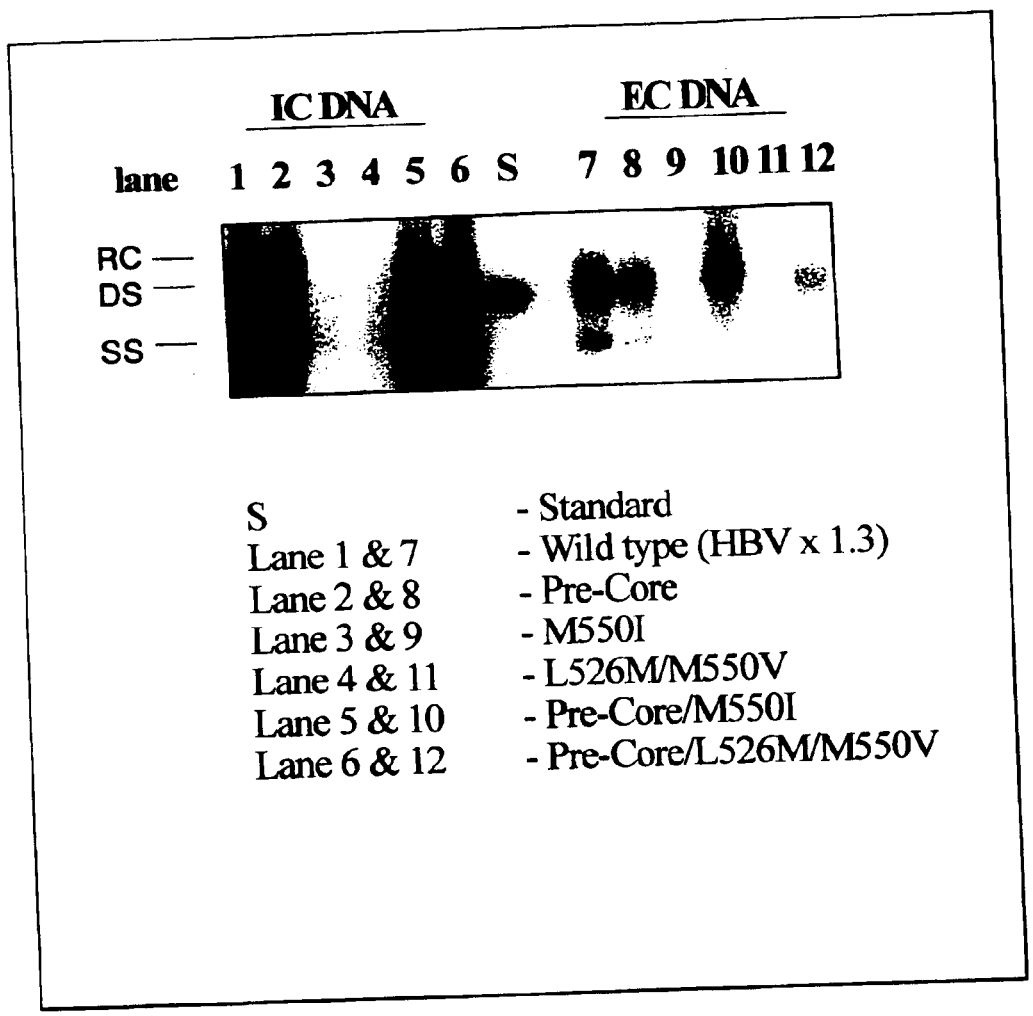
FIG. 12 is a photographic representation showing Southern blot of intracellular and extracellular HBV DNA production from HepG2 cells transduced with various recombinant HBV-baculovirus M550I, precore/M550I, L526/M550V and precore/L526M/M550V.
Figures 13E, 13F:
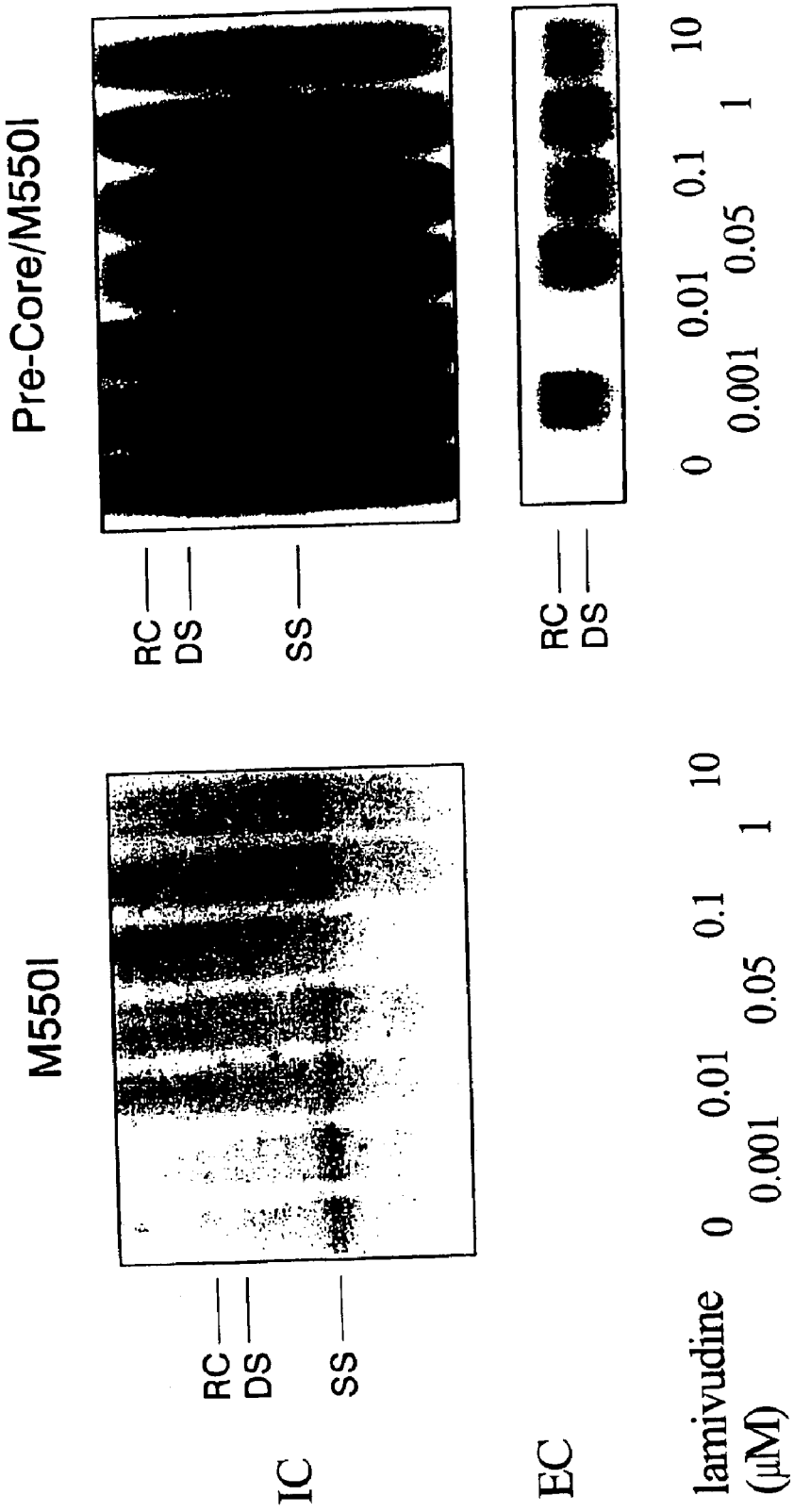
Figures 13G, 13H:
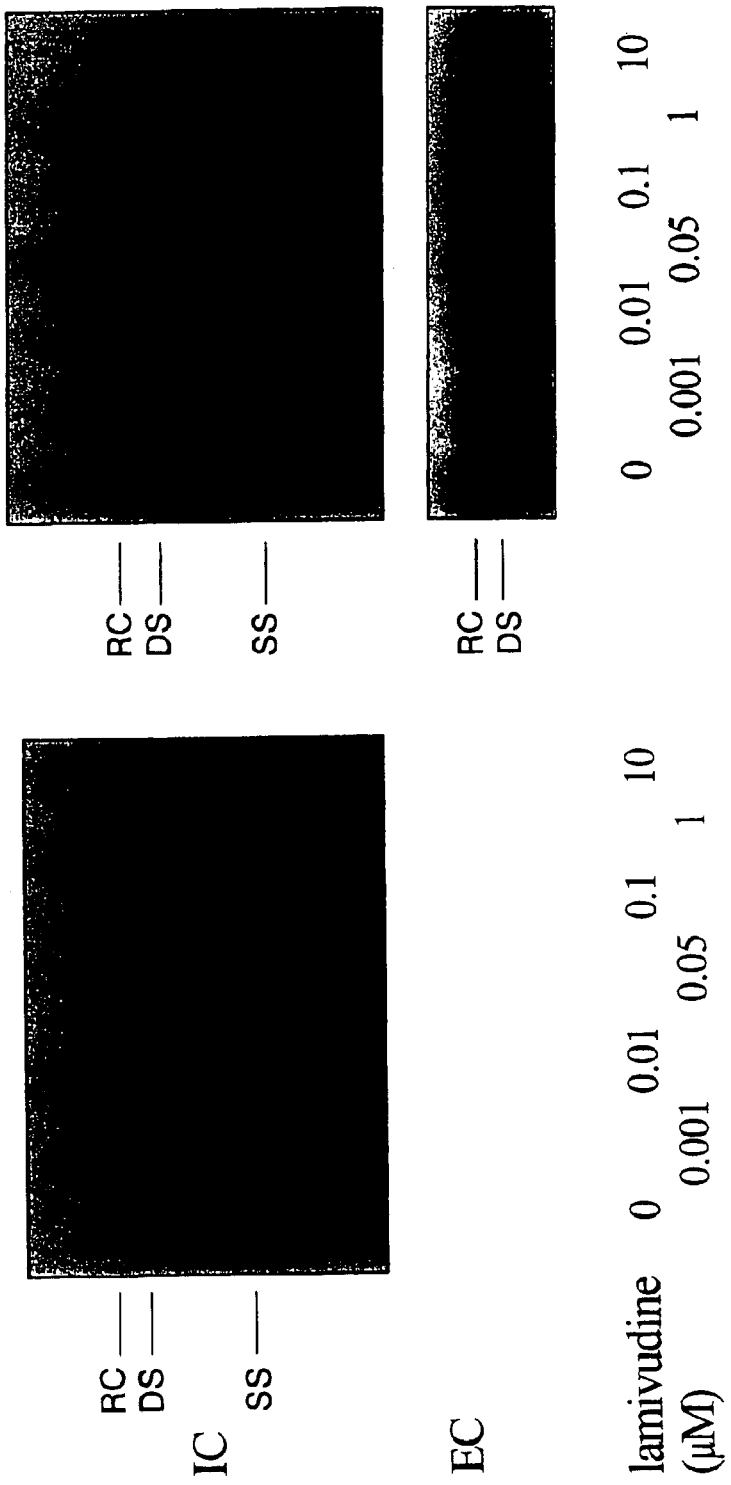
Figures 13I, 13J:
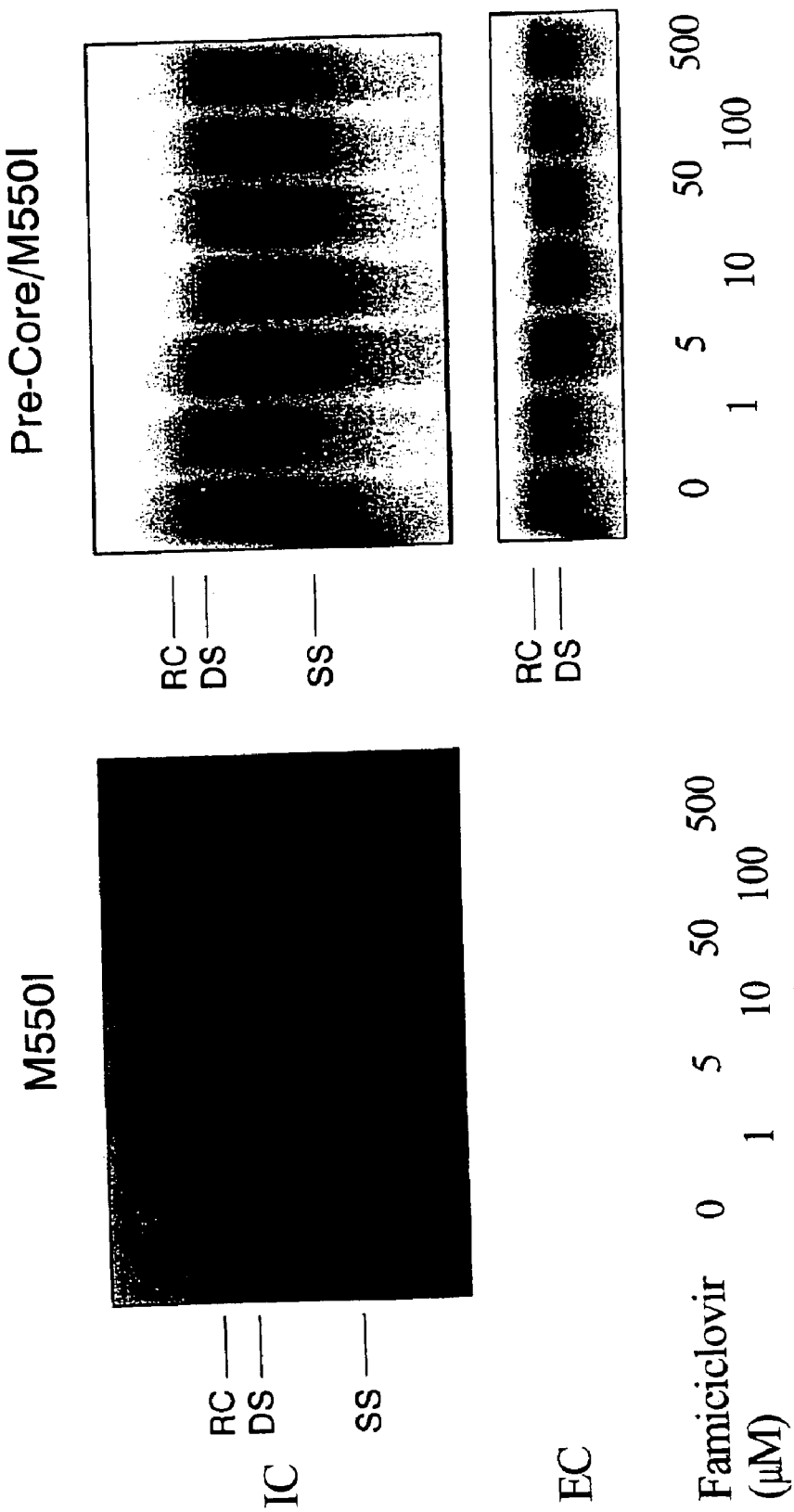
Figures 13K, 13L:
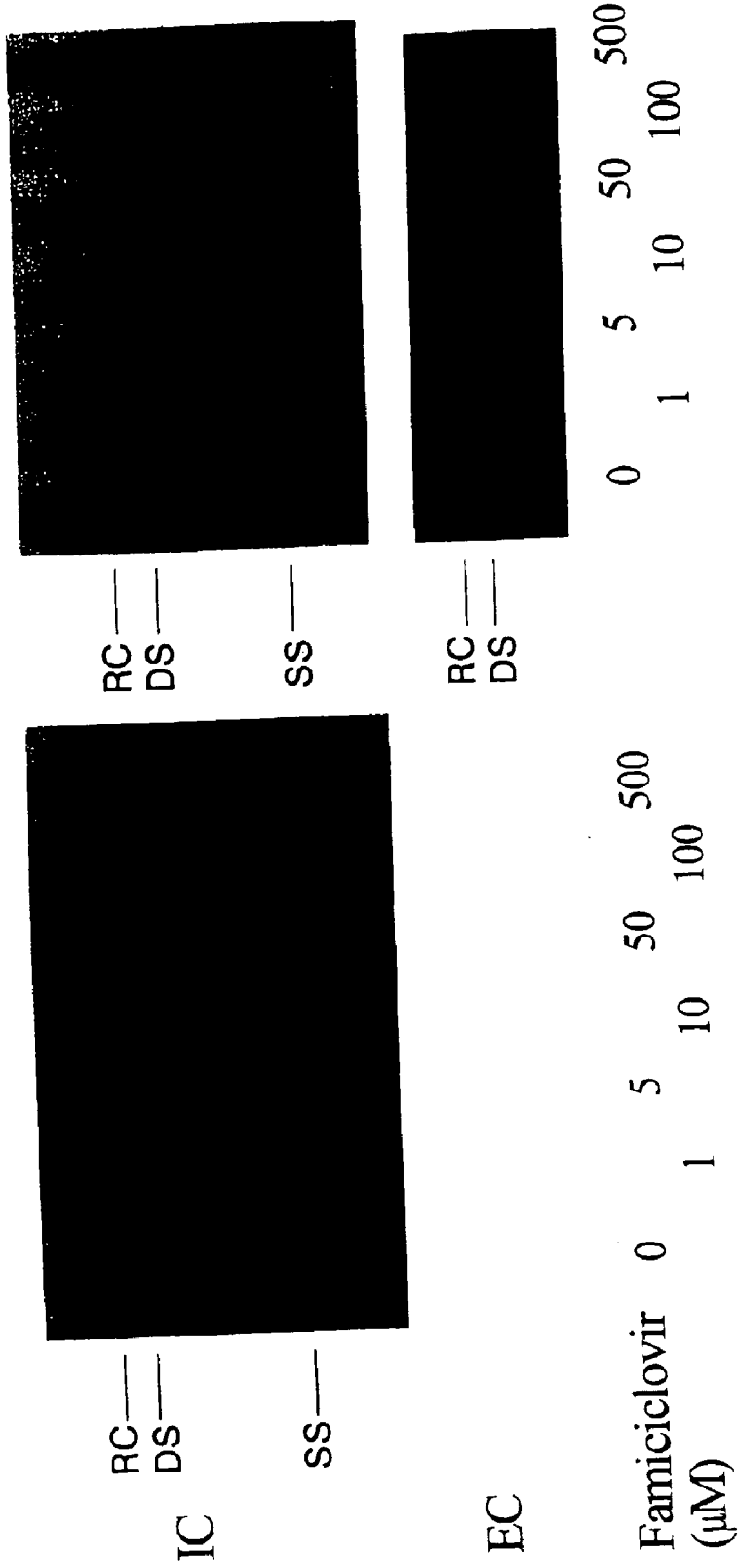

2. Antiviral Testing with the Precore Mutant (G1869A), and L526M/M550V or M550I HBV Baculovirus Intracellular HBV DNA and extracellular virus produced by HepG2 cells transduced with various recombinant HBV/baculovirus (including L526M/M550V, precore/L526M/L550V, M550I and precore/M550I) are shown in FIG. 12.

The HBV DNA yield from the various mutants showed that wild-type and precore mutant were comparable, the M550I and L526M/M550V mutants showed much lower HBV DNA production than wild-type, and the precore/M550I and precore/L526M/552V mutants had similar levels of DNA production (both intracellular and extracellular) as the precore mutant. The presence of M550I and L526M/M550V changes did not seem to diminish their replication fitness compared to the precore mutant.

Intracellular HBV DNA and extracellular virus produced by HepG2 cells transduced with various recombinant HBV-baculovirus (including M550I, precore/M550I L526M/M550V and precore/L526M/L550V) in the presence of adefovir, or lamivudine or penciclovir are shown in FIGS. 13A to 13L and the calculated IC50 for adevoir is shown in Table 4. The adefovir concentration required to inhibit HBV replication (intracellular single-stranded DNA) by 50% ($IC_{50}$) was 0.94 μM and 0.93 μM for the recombinant HBV-baculovirus mutants M550I and L526M/M550V respectively, and 0.28 μM and 0.47 μM for precore/M550I and precore/L526M/M550V respectively. The Southern blots of intracellular HBV replicative intermediates and extracellular virus produced by HepG2 cells transduced with respective recombinant HBV-baculovirus showed that for any HBV/baculovirus variant encoding the mutations at M550I or L526M/M550V changes conferred a high degree of resistance to lamivudine and penciclovir and no dose response could be plotted.

TABLE 3

$IC_{50}$ of adefovir, lamivudine and penciclovir for wild-type (WT) or precore (G1896A) recombinant HBV-baculovirus

| Drugs | | WT | Precore |
|---|---|---|---|
| adefovir | IC SS[i] | 0.235[a] | 0.195[b] |
| $IC_{50}$ (μM) | EC RC[j] | 0.0535[c] | 0.025[d] |
| lamivudine | IC SS | 0.0697[e] | 0.0207[f] |
| $IC_{50}$ (μM) | EC RC | 0.018[g] | 0.011[h] |
| penciclovir | IC SS | 226 | 85 |
| $IC_{50}$ (μM) | EC RC | 23 | 6 |

[a]average of 2 experiments (0.25 and 0.22 μM)
[b]average of 2 experiments (0.20 and 0.19 μM)
[c]average of 2 experiments (0.06 and 0.047 μM)
[d]average of 2 experiments (0.02 and 0.03 μM)
[e]average of 3 experiments (0.067, 0.085 and 0.0572 μM)
[f]average of 3 experiments (0.014, 0.014 and 0.032 μM)
[g]average of 3 experiments (0.022, 0.0293 and 0.0095 μM)
[h]average of 3 experiments (0.012, 0.01 and 0.01 μM)
[i]intracellular single-stranded HBV DNA
[j]extracellular relaxed circular HBV DNA

TABLE 4

$IC_{50}$ of adefovir, lamivudine and penciclovir for recombinant HBV-baculovirus encoding changes conferring lamivudine resistance with or without the precore (G1896A) mutation

| Recombinant HBV-baculovirus | | adefovir $IC_{50}$ (μM) | lamivudine $IC_{50}$ (μM) | penciclovir $IC_{50}$ (μM) |
|---|---|---|---|---|
| M550I | IC SS | 0.94 | NDR | NDR |
| | EC RC | * | * | * |
| L526M/M550V | IC SS | 0.93 | NDR | NDR |
| | EC RC | * | * | * |
| Precore/M550I | IC SS | 0.28 | NDR | NDR |
| | EC RC | 0.09 | NDR | NDR |
| Precore/L526M/M550V | IC SS | 0.47 | NDR | NDR |
| | EC RC | 1.0 | NDR | NDR |

NDR no dose response
*HBV DNA production to low to be measured.
IC SS intracellular single-stranded HBV DNA
EC RC extracellular relaxed circular HBV DNA Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

Bibliography

1. Norder et al. *J. Gen. Virol.* 74; 341–1348, 1993.

2. Stuyver et al., A new genotype of hepatitis B virus: complete genome and phylogenetic relatedness. *J Gen Virol.* 81: 67–74, 2000.

3. Ryder et al. *Lancet* ii(8400): 449–52, 1984.

4. Beasley et al. *Lancet ii;* 1159–63, 1981

5. Tiollais et al. *Nature* 317: 489–495, 1985.

6. Gerlich et al. *Viral Hepatitis and Liver Disease.* F. B. Hollinger et al. eds Williams-Wilkens, Baltimore, Md., pp121–134, 1991.

7. Carman et al. *Gastroenterology* 102: 711–719, 1992.

8. Carman et al. *Lancet* 336: 325–329, 1990.

9. Okamoto et al. *Paediatric Research* 32: 264–268, 1992.

10. McMahon et al. *Hepatology* 15: 757–766, 1992.

11. Fujii et al. *Biochem. Biophys. Res. Commun.* 184: 1152–1157, 1992.

12. Harrison et al. *J. Hepatol.* 13: 5105–5107, 1991.

13. Delaney and Isom HC, *Hepatology* 28: 1134–46, 1998

14. Delaney et al. *Antimicrob Agents Chemother* 43; 2017–26, 1999

15. Angus et al., *Hepatology* 21: 14–8, 1995

16. King et al., *Antimicrob Agents Chemother.* 42: 3179–86, 1998

What is claimed is:

1. A method for detecting a variant HBV which exhibits an altered sensitivity to an agent, said method comprising:
   generating a genetic construct comprising a replication competent amount of the genome from said variant HBV contained in or fused to an amount of a baculovirus genome capable of infecting hepatocyte cells and then infecting said cells with said construct;
   contacting said cells, before, during, or after infection, with the agent to be tested;
   optionally further infecting said cells with the same genetic construct or a genetic construct comprising the genome of HBV wild type or another HBV variant;
   culturing said cells for a time and under conditions sufficient for the variant HBV to to be detected to replicate, express genetic sequences or assemble or release virus or virus-like particles if resistant to said agent; and
   subjecting the cells, cell lysates or culture supernatant fluid to viral- or viral-component-detection means to determine whether or not the variant HBV has replicated, expressed genetic material, assembled, or been released in the presence of said agent.

2. A method according to claim 1 wherein the variant HBV is capable of replicating in the presence of an agent which inhibits or reduces infection, replication or assembly of a reference HBV.

3. A method according to claim 2 wherein the agent is a nucleoside analogue or a non-nucleoside analogue.

4. A method according to claim 2 wherein the agent is an immunointeractive molecule.

5. A method according to claim 3 wherein the agent is a non-nucleoside analogue reverse transcriptase inhibitor, a non-nucleoside analogue DNA dependent DNA polymerase inhibitor, or both a non-nucleoside analogue reverse transcriptase inhibitor and a non-nucleoside analogue DNA dependent DNA polymerase inhibitor.

6. A method according to claim 3 wherein the nucleoside analogue is 3TC, PMEA or PCV.

7. A method according to claim 4 wherein the immunointeractive molecule is an antibody.

8. A method according to any one of claims 1 to 7 wherein the variant HBV comprises an altered HBV DNA polymerase, and altered HBV precore promoter or basal core promoter, an altered HBsAg, or a combination thereof.

9. A method according to claim 8 wherein the altered HBV DNA polymerase is selected from the group consisting of L426I/V, L428I/VN480G, N485K, K495R, R499Q, G499E, W499Q, F512L, I515L, V519L, L526M, M550V, M550I, V553I, S565P.

10. A method according to claim 8 wherein the altered HBV precore promoter or basal core promoter is selected from the group consisting A1814T, C1856T, G1896A, G1897A, G1898A, G1899A, G1896A/G1899A, A1762T/G1764A, T1753C, G1757A and C1653T where the numbering is from the unique EcoRI site in HBV.

11. A method according to claim 8 wherein the altered HBsAg is selected from the group consisting of G112R, T123P Y/F134S, D144E, G145R, A157D, E164D, F170L, M195I, W196L, W196S, W196STOP, M198I, W199S, S204T, S210R.

12. A method according to claim 8 wherein the altered HBsAg is selected from the group consisting of D144E, G145R, A157D, E164D, M195I, W196L, W196S, W196STOP, M198I, W199S and S210R.

13. A method according to claim 8 wherein the cells are co-infected with multiple combinations of different variant HBVs comprising an altered HBV precore promoter or basal core promoter or an altered HBV HBsAg or an altered HBV DNA polymerase or combinations thereof.

14. A method according to claim 8 wherein the cells are superinfected with multiple combinations of different variant HBVs comprising an altered HBV precore promoter or basal core promoter or an altered HBV HBsAg or an altered HBV DNA polymerase or combinations thereof.

15. A method according to any one of claim 1 to 8 wherein the altered HBV is a multiple mutant selected from the group consisting of L526M/M5501, L526M/M550V, V519L/L526M/M550V and V519L/L526M/M5501.

16. A method for detecting a variant HBV comprising DNA polymerase which exhibits an altered sensitivity to an agent said method comprising:

generating a genetic construct comprising a replication competent amount of the genome from said variant HBV contained in or fused to an amount of a baculovirus genome capable infecting hepatocyte cells and then infecting said cells with said construct;

contacting said cells, before, during, or after infection, with the agent to be tested;

optionally further infecting said cells with the same genetic construct or a genetic construct comprising the genome of HBV wild type or another HBV variant;

culturing said cells for a time and under conditions sufficient for the variant HBV to be detected to replicate, express genetic sequences, or assemble, or release virus or virus-like particles if resistant to said agent; and subjecting the cells, cell lysates or culture supernatant fluid or virus purified therefrom to HBV DNA polymerase assay in the presence or absence of said agent to determine whether said variant HBV exhibits an altered sensitivity to said agent, wherein said agent comprises nucleoside triphosphate analogues or non-nucleoside analogues reverse transcriptase inhibitors or non-nucleoside analogues DNA dependent DNA polymerase inhibitors.

17. A method for detecting HBV DNA polymerase activity in the presence of an antiviral agent said method comprising:

generating a genetic construct comprising a replication competent amount of a genome from an HBV capable of producing said DNA polymerase, said genome contained in or fused to an amount of a baculovirus genome capable of infecting hepatocyte cells and then infecting said cells with said construct;

contacting said cells, before, during, or after infection, with the agent to be tested;

optionally further infecting said cells with the same genetic construct or a genetic construct comprising the genome of HBV wild type or another HBV strain;

culturing said cells for a time and under conditions sufficient for said variant HBV to replicate, express genetic sequences, assemble, or release virus or virus-like particles if resistant to said agent; and subjecting the cells, cell lysates or culture supernatant fluid or virus purified therefrom to HBV DNA polymerase assay in the presence or absence of said antiviral agent to determine whether said variant HBV exhibits an altered sensitivity to said agent, wherein said antiviral agent comprises nucleoside triphosphate analogues or non-nucleoside analogues reverse transcriptase inhibitors or non-nucleoside analogues DNA dependent DNA polymerase inhibitors.

* * * * *